(12) United States Patent
Öberg

(10) Patent No.: US 10,047,347 B2
(45) Date of Patent: Aug. 14, 2018

(54) ONCOLYTIC ADENOVIRUSES WITH INCREASED PROPORTION OF THE 156R SPLICING ISOFORM OF THE E1B PROTEIN

(71) Applicant: Ixogen Ltd., London (GB)

(72) Inventor: Hans Daniel Öberg, Uppsala (SE)

(73) Assignee: Ixogen Ltd., London (GB)

( * ) Notice: Subject to any disclaimer, the term of this patent is extended or adjusted under 35 U.S.C. 154(b) by 80 days.

(21) Appl. No.: 14/648,661

(22) PCT Filed: Nov. 29, 2013

(86) PCT No.: PCT/GB2013/053177
§ 371 (c)(1),
(2) Date: May 29, 2015

(87) PCT Pub. No.: WO2014/083362
PCT Pub. Date: Jun. 5, 2014

(65) Prior Publication Data
US 2015/0315547 A1    Nov. 5, 2015

(30) Foreign Application Priority Data

Nov. 30, 2012 (GB) .................................. 1221590.1

(51) Int. Cl.
C12N 7/04        (2006.01)
A61K 39/285    (2006.01)
A61K 39/00      (2006.01)
C12N 7/00        (2006.01)
A61K 35/761    (2015.01)

(52) U.S. Cl.
CPC .............. *C12N 7/00* (2013.01); *A61K 35/761* (2013.01); *C12N 2710/10321* (2013.01); *C12N 2710/10322* (2013.01); *C12N 2710/10332* (2013.01)

(58) Field of Classification Search
None
See application file for complete search history.

(56) References Cited

U.S. PATENT DOCUMENTS 6,764,674 B1 *  7/2004  Hermiston ............. C12N 15/86
                                                                       424/93.2
2005/0186178 A1   8/2005  Ennist et al.

FOREIGN PATENT DOCUMENTS

WO        9835028         8/1998
WO        2012132369   10/2012

OTHER PUBLICATIONS

Kim et al., "Evaluation of E1B gene-attenuated replicating adenoviruses for cancer gene therapy," Cancer Gene Therapy 9: 725-726 (2002).*

(Continued)

*Primary Examiner* — Janet L Andres
*Assistant Examiner* — M Franco G Salvoza
(74) *Attorney, Agent, or Firm* — Kilpatrick Townsend & Stockton LLP

(57) ABSTRACT

The invention relates to a recombinant adenovirus that has an oncolytic effect in a cancer cell. By modulating the level and type of splice isoforms of the E1B gene product, expressed from the E1B gene, the oncolytic activity of such viruses can be enhanced. The invention provides a recombinant adenovirus in which the proportion of the E1B-156R isoform is increased relative to wild-type levels. Such a recombinant adenovirus may selectivity replicate in cancer cells, thereby killing cancer cells while sparing normal cells.

12 Claims, 16 Drawing Sheets

(56) References Cited

OTHER PUBLICATIONS

Sharma et al., "Adenovirus vector-based strategies for cancer therapy," Curr Drug Ther 4(2): 117-138 (2009).*
Kaliberova et al., "CRAdRGDflt-IL24 virotherapy in combination with chemotherapy of experimental glioma," Cancer Gene Ther 16(10): 794-805 (2009).*
Ching et al., "The human adenovirus type 5 E1B 55-kilodalton protein is phosphorylated by protein kinase CK2", *Journal of Virology*, vol. 86(5), available online at http://jvi.asm.org/content/85/5/2400.full.pdf+html, pp. 2400-2415 (Mar. 2012).
Choi et al., "Evolution of oncolytic adenovirus for cancer treatment", *Advanced Drug Delivery Reviews*, vol. 64, Issue 8, pp. 720-729 (Jun. 1, 2012).
GB1221590.1 , "Search Report", dated Apr. 10, 2013, 4 pages.
Kindsmuller et al., "A 49-Kilodalton Isoform of the Adenovirus Type 5 Early Region 1B 55-Kilodalton Protein is Sufficient to Support Virus Replication", *Journal of Virology*, 83(18), available online at http://europepmc.org/articles/PMC2738261/, pp. 9045-9056 (Sep. 2009).
PCT/GB2013/053177 , "International Search Report and Written Opinion", dated Mar. 6, 2014, 10 pages.
Sieber , "Untersuchung des funktionellen Potenzials der Adenovirus Typ 5 E1BN-Proteine", Naturwissenschaftliche Fakultat III, Universitat Regensburg, retrieved from the Internet: http://epub.uni-regensburg.de/12134/1/Diss.T.Sieber2.1_interaktiv.pdf, Summary, Sections 5 and 6, 188 pages (May 2008).

\* cited by examiner

*FIGURE 9*

| NHBE cells | Ad5wt | Onyx-015 | Ixo-ctrl | Ixovex |
|---|---|---|---|---|
| EC50 (pfu/cell) | 0,042 | 0,63 | 0,031 | 23 |
| Relative EC50 | 535 | 36 | 735 | 1,0 |

FIGURE 12

| Experiment<br>virus / AdX-156R / cancer cell used / normal cell used | Replication capacity / pfu/cell | | | | OI |
|---|---|---|---|---|---|
| | a | b | c | d | (a/b)/(c/d) |
| Ad5 / Ad5-156R / Hela / NHBE | 3710 | 5.13 | 5989 | 31.0 | 3.7 |
| Ad5 / Ad5-156R / H460 / NHBE | 32662 | 5.13 | 4447 | 31.0 | 44 |
| Ad5 / Ad2-156R / Hela / NHBE | 3366 | 6.26 | 5989 | 31.0 | 2.8 |
| ONYX015 / Ad5-156R / Hela / NHBE | 805 | 242 | 1715 | 2835 | 5.5 |
| Ad2 / Ad5-156R / Hela / NHBE | 39037 | 3731 | 50945 | 73170 | 15 | where:

a = cancer cells (Hela or H460) + AdX-156R b = normal cells (NHBE) + AdX-156R c = cancer cells (Hela or H460) AdX– 156R d = normal cells – AdX-156R and oncolytic index (OI) = (OV$_{cancer\ cell}$(a) /OV$_{normal\ cell}$ (b) )/(WT OV$_{cancer\ cell}$ (c) /WT$_{normal\ cell}$ (d)) where OV is oncolytic virus replication capacity and WT is wild type virus replication capacity.

SEQUENCE LISTING

```
<160> NUMBER OF SEQ ID NOS: 46

<210> SEQ ID NO 1
<211> LENGTH: 2330
<212> TYPE: DNA
<213> ORGANISM: Adenovirus

<400> SEQUENCE: 1
atggaggctt gggagtgttt ggaagatttt tctgctgtgc gtaacttgct ggaacagagc      60
tctaacagta cctcttggtt ttggaggttt ctgtggggct catcccaggc aaagttagtc     120
tgcagaatta aggaggatta caagtgggaa tttgaagagc ttttgaaatc ctgtggtgag     180
ctgtttgatt ctttgaatct gggtcaccag gcgcttttcc aagagaaggt catcaagact     240
ttggattttt ccacaccggg gcgcgctgcg gctgctgttg cttttttgag ttttataaag     300
gataaatgga gcgaagaaac ccatctgagc gggggtacc tgctggattt tctggccatg     360
catctgtgga gagcggttgt gagacacaag aatcgcctgc tactgttgtc ttccgtccgc     420
ccggcgataa taccgacgga ggagcagcag cagcagcagg aggaagccag gcggcggcgg     480
caggagcaga gcccatggaa cccgagagcc ggcctggacc ctcgggaatg aatgttgtac     540
aggtggctga actgtatcca gaactgagac gcattttgac aattacagag gatgggcagg     600
ggctaaaggg ggtaaagagg gagcgggggg cttgtgaggc tacagaggag gctaggaatc     660 tagctttag cttaatgacc agacaccgtc ctgagtgtat tactttcaa cagatcaagg     720
```

| | | |
|---|---|---|
| ataattgcgc taatgagctt gatctgctgg cgcagaagta ttccatagag cagctgacca | 780 |
| cttactggct gcagccaggg gatgattttg aggaggctat tagggtatat gcaaaggtgg | 840 |
| cacttaggcc agattgcaag tacaagatca gcaaacttgt aaatatcagg aattgttgct | 900 |
| acatttctgg gaacgggggcc gaggtggaga tagatacgga ggataggggtg gcctttagat | 960 |
| gtagcatgat aaatatgtgg ccggggggtgc ttggcatgga cggggtggtt attatgaatg | 1020 |
| taaggtttac tggccccaat tttagcggta cggttttcct ggccaatacc aaccttatcc | 1080 |
| tacacggtgt aagcttctat gggtttaaca atacctgtgt ggaagcctgg accgatgtaa | 1140 |
| gggttcgggg ctgtgccttt tactgctgct ggaaggggggg ggtgtgtcgc cccaaaagca | 1200 |
| gggcttcaat taagaaatgc ctctttgaaa ggtgtacctt gggtatcctg tctgagggta | 1260 |
| actccagggt gcgccacaat gtggcctccg actgtggttg cttcatgcta gtgaaaagcg | 1320 |
| tggctgtgat taagcataac atggtatgtg gcaactgcga ggacagggcc tctcagatgc | 1380 |
| tgacctgctc ggacggcaac tgtcacctgc tgaagaccat tcacgtagcc agccactctc | 1440 |
| gcaaggcctg gccagtgttt gagcataaca tactgacccg ctgttccttg catttgggta | 1500 |
| acaggagggg ggtgttccta ccttaccaat gcaatttgag tcacactaag atattgcttg | 1560 |
| agcccgagag catgtccaag gtgaacctga acggggtgtt tgacatgacc atgaagatct | 1620 |
| ggaaggtgct gaggtacgat gagacccgca ccaggtgcag accctgcgag tgtggcggta | 1680 |
| aacatattag gaaccagcct gtgatgctgg atgtgaccga ggagctgagg cccgatcact | 1740 |
| tggtgctggc ctgcacccgc gctgagtttg gctctagcga tgaagataca gattgaggta | 1800 |
| ctgaaatgtg tgggcgtggc ttaagggtgg gaaagaatat ataaggtggg ggtcttatgt | 1860 |
| agttttgtat ctgttttgca gcagccgccg ccgccatgag caccaactcg tttgatggaa | 1920 |
| gcattgtgag ctcatatttg acaacgcgca tgcccccatg ggccggggtg cgtcagaatg | 1980 |
| tgatgggctc cagcattgat ggtcgccccg tcctgcccgc aaactctact acccttgacct | 2040 |
| acgagaccgt gtctggaacg ccgttggaga ctgcagcctc cgccgccgct tcagccgctg | 2100 |
| cagccaccgc ccgcgggatt gtgactgact ttgctttcct gagcccgctt gcaagcagtg | 2160 |
| cagcttcccg ttcatccgcc cgcgatgaca agttgacggc tcttttggca caattggatt | 2220 |
| ctttgacccg ggaacttaat gtcgtttctc agcagctgtt ggatctgcgc cagcaggttt | 2280 |
| ctgccctgaa ggcttcctcc cctcccaatg cggtttaaaa cataaataaa | 2330 |

<210> SEQ ID NO 2
<211> LENGTH: 471
<212> TYPE: DNA
<213> ORGANISM: Adenovirus

<400> SEQUENCE: 2

| | | |
|---|---|---|
| atggagcgaa gaaacccatc tgagcggggg gtacctgctg gattttctgg ccatgcatct | 60 |
| gtggagagcg gttgtgagac acaagaatcg cctgctactg ttgtcttccg tccgcccggc | 120 |
| gataataccg acggaggagc agcagcagca gcaggaggaa gccaggcggc ggcggcagga | 180 |
| gcagagccca tggaacccga gagccggcct ggaccctcgg gaatgaatgt tgtacagccc | 240 |
| gagagcatgt ccaaggtgaa cctgaacggg gtgtttgaca tgaccatgaa gatctggaag | 300 |
| gtgctgaggt acgatgagac ccgcaccagg tgcagaccct gcgagtgtgg cggtaaacat | 360 |
| attaggaacc agcctgtgat gctggatgtg accgaggagc tgaggcccga tcacttggtg | 420 |
| ctggcctgca cccgcgctga gtttggctct agcgatgaag atacagattg a | 471 |

<210> SEQ ID NO 3
<211> LENGTH: 156
<212> TYPE: PRT
<213> ORGANISM: Adenovirus

<400> SEQUENCE: 3

Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
            20                  25                  30

Thr Val Val Phe Arg Pro Pro Gly Asp Asn Thr Asp Gly Gly Ala Ala
        35                  40                  45

Ala Ala Ala Gly Gly Ser Gln Ala Ala Ala Gly Ala Glu Pro Met
    50                  55                  60

Glu Pro Glu Ser Arg Pro Gly Pro Ser Gly Met Asn Val Val Gln Pro
65                  70                  75                  80

Glu Ser Met Ser Lys Val Asn Leu Asn Gly Val Phe Asp Met Thr Met
                85                  90                  95

Lys Ile Trp Lys Val Leu Arg Tyr Asp Glu Thr Arg Thr Arg Cys Arg
            100                 105                 110

Pro Cys Glu Cys Gly Gly Lys His Ile Arg Asn Gln Pro Val Met Leu
        115                 120                 125

Asp Val Thr Glu Glu Leu Arg Pro Asp His Leu Val Leu Ala Cys Thr
    130                 135                 140

Arg Ala Glu Phe Gly Ser Ser Asp Glu Asp Thr Asp
145                 150                 155

<210> SEQ ID NO 4
<211> LENGTH: 1491
<212> TYPE: DNA
<213> ORGANISM: Adenovirus

<400> SEQUENCE: 4
atggagcgaa gaaacccatc tgagcggggg gtacctgctg gattttctgg ccatgcatct      60
gtggagagcg gttgtgagac acaagaatcg cctgctactg ttgtcttccg tccgcccggc     120
gataataccg acggaggagc agcagcagca gcaggaggaa gccaggcggc ggcggcagga     180
gcagagccca tggaacccga gagccggcct ggaccctcgg gaatgaatgt tgtacaggtg     240
gctgaactgt atccagaact gagacgcatt ttgacaatta cagaggatgg gcaggggcta     300
aaggggtaa agagggagcg gggggcttgt gaggctacag aggaggctag gaatctagct     360
tttagcttaa tgaccagaca ccgtcctgag tgtattactt tcaacagat caaggataat     420
tgcgctaatg agcttgatct gctggcgcag aagtattcca tagagcagct gaccacttac     480
tggctgcagc caggggatga ttttgaggag gctattaggg tatatgcaaa ggtggcactt     540
aggccagatt gcaagtacaa gatcagcaaa cttgtaaata tcaggaattg ttgctacatt     600
tctgggaacg gggccgaggt ggagatagat acggaggata gggtggcctt tagatgtagc     660
atgataaata tgtggccggg ggtgcttggc atggacgggg tggttattat gaatgtaagg     720
tttactggcc ccaattttag cggtacggtt tccctgccca ataccaacct tatcctacac     780
ggtgtaagct tctatgggtt taacaatacc tgtgtggaag cctggaccga tgtaagggtt     840
cggggctgtg cctttactg ctgctggaag ggggtggtgt gtcgcccaa aagcagggct     900
tcaattaaga aatgcctctt tgaaaggtgt accttggta tcctgtctga gggtaactcc     960
agggtgcgcc acaatgtggc ctccgactgt ggttgcttca tgctagtgaa aagcgtggct    1020

-continued

```
gtgattaagc ataacatggt atgtggcaac tgcgaggaca gggcctctca gatgctgacc    1080
tgctcggacg gcaactgtca cctgctgaag accattcacg tagccagcca ctctcgcaag    1140
gcctggccag tgtttgagca taacatactg acccgctgtt ccttgcattt gggtaacagg    1200 agggggtgt tcctacctta ccaatgcaat ttgagtcaca ctaagatatt gcttgagccc     1260
gagagcatgt ccaaggtgaa cctgaacggg gtgtttgaca tgaccatgaa gatctggaag    1320
gtgctgaggt acgatgagac ccgcaccagg tgcagaccct gcgagtgtgg cggtaaacat    1380
attaggaacc agcctgtgat gctggatgtg accgaggagc tgaggcccga tcacttggtg    1440
ctggcctgca cccgcgctga gtttggctct agcgatgaag atacagattg a             1491
```

<210> SEQ ID NO 5
<211> LENGTH: 496
<212> TYPE: PRT
<213> ORGANISM: Adenovirus

<400> SEQUENCE: 5

```
Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
            20                  25                  30

Thr Val Val Phe Arg Pro Pro Gly Asp Asn Thr Asp Gly Gly Ala Ala
        35                  40                  45

Ala Ala Ala Gly Gly Ser Gln Ala Ala Ala Gly Ala Glu Pro Met
    50                  55                  60

Glu Pro Glu Ser Arg Pro Gly Pro Ser Gly Met Asn Val Val Gln Val
65                  70                  75                  80

Ala Glu Leu Tyr Pro Glu Leu Arg Arg Ile Leu Thr Ile Thr Glu Asp
                85                  90                  95

Gly Gln Gly Leu Lys Gly Val Lys Arg Glu Arg Gly Ala Cys Glu Ala
            100                 105                 110

Thr Glu Glu Ala Arg Asn Leu Ala Phe Ser Leu Met Thr Arg His Arg
        115                 120                 125

Pro Glu Cys Ile Thr Phe Gln Gln Ile Lys Asp Asn Cys Ala Asn Glu
    130                 135                 140

Leu Asp Leu Leu Ala Gln Lys Tyr Ser Ile Glu Gln Leu Thr Thr Tyr
145                 150                 155                 160

Trp Leu Gln Pro Gly Asp Asp Phe Glu Glu Ala Ile Arg Val Tyr Ala
                165                 170                 175

Lys Val Ala Leu Arg Pro Asp Cys Lys Tyr Lys Ile Ser Lys Leu Val
            180                 185                 190

Asn Ile Arg Asn Cys Cys Tyr Ile Ser Gly Asn Gly Ala Glu Val Glu
        195                 200                 205

Ile Asp Thr Glu Asp Arg Val Ala Phe Arg Cys Ser Met Ile Asn Met
    210                 215                 220

Trp Pro Gly Val Leu Gly Met Asp Gly Val Val Ile Met Asn Val Arg
225                 230                 235                 240

Phe Thr Gly Pro Asn Phe Ser Gly Thr Val Phe Leu Ala Asn Thr Asn
                245                 250                 255

Leu Ile Leu His Gly Val Ser Phe Tyr Gly Phe Asn Asn Thr Cys Val
            260                 265                 270

Glu Ala Trp Thr Asp Val Arg Val Arg Gly Cys Ala Phe Tyr Cys Cys
        275                 280                 285
```

Trp Lys Gly Val Val Cys Arg Pro Lys Ser Arg Ala Ser Ile Lys Lys
            290                 295                 300

Cys Leu Phe Glu Arg Cys Thr Leu Gly Ile Leu Ser Glu Gly Asn Ser
305                 310                 315                 320

Arg Val Arg His Asn Val Ala Ser Asp Cys Gly Cys Phe Met Leu Val
                325                 330                 335

Lys Ser Val Ala Val Ile Lys His Asn Met Val Cys Gly Asn Cys Glu
            340                 345                 350

Asp Arg Ala Ser Gln Met Leu Thr Cys Ser Asp Gly Asn Cys His Leu
                355                 360                 365

Leu Lys Thr Ile His Val Ala Ser His Ser Arg Lys Ala Trp Pro Val
370                 375                 380

Phe Glu His Asn Ile Leu Thr Arg Cys Ser Leu His Leu Gly Asn Arg
385                 390                 395                 400

Arg Gly Val Phe Leu Pro Tyr Gln Cys Asn Leu Ser His Thr Lys Ile
                405                 410                 415

Leu Leu Glu Pro Glu Ser Met Ser Lys Val Asn Leu Asn Gly Val Phe
            420                 425                 430

Asp Met Thr Met Lys Ile Trp Lys Val Leu Arg Tyr Asp Glu Thr Arg
                435                 440                 445

Thr Arg Cys Arg Pro Cys Glu Cys Gly Gly Lys His Ile Arg Asn Gln
            450                 455                 460

Pro Val Met Leu Asp Val Thr Glu Glu Leu Arg Pro Asp His Leu Val
465                 470                 475                 480

Leu Ala Cys Thr Arg Ala Glu Phe Gly Ser Ser Asp Glu Asp Thr Asp
                485                 490                 495

<210> SEQ ID NO 6
<211> LENGTH: 282
<212> TYPE: DNA
<213> ORGANISM: Adenovirus

<400> SEQUENCE: 6
atggagcgaa gaaacccatc tgagcggggg gtacctgctg gattttctgg ccatgcatct      60
gtggagagcg gttgtgagac acaagaatcg cctgctactg ttgtcttccg tccgcccggc     120
gataataccg acggaggagc agcagcagca gcaggaggaa gccaggcggc ggcggcagga     180
gcagagccca tggaacccga gagccggcct ggaccctcgg gaatgaatgt tgtacaggag     240
gggggtgttc ctaccttacc aatgcaattt gagtcacact aa                        282

<210> SEQ ID NO 7
<211> LENGTH: 93
<212> TYPE: PRT
<213> ORGANISM: Adenovirus

<400> SEQUENCE: 7

Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
            20                  25                  30

Thr Val Val Phe Arg Pro Gly Asp Asn Thr Asp Gly Gly Ala Ala
                35                  40                  45

Ala Ala Ala Gly Gly Ser Gln Ala Ala Ala Gly Ala Glu Pro Met
            50                  55                  60

Glu Pro Glu Ser Arg Pro Gly Pro Ser Gly Met Asn Val Val Gln Glu
65                  70                  75                  80

Gly Gly Val Pro Thr Leu Pro Met Gln Phe Glu Ser His
                85                  90

<210> SEQ ID NO 8
<211> LENGTH: 255
<212> TYPE: DNA
<213> ORGANISM: Adenovirus

<400> SEQUENCE: 8
atggagcgaa gaaacccatc tgagcggggg gtacctgctg gattttctgg ccatgcatct      60
gtggagagcg gttgtgagac acaagaatcg cctgctactg ttgtcttccg tccgcccggc     120
gataataccg acggaggagc agcagcagca gcaggaggaa gccaggcggc ggcggcagga     180
gcagagccca tggaacccga gagccggcct ggaccctcgg gaatgaatgt tgtacagcag     240
ccgccgccgc catga                                                     255

<210> SEQ ID NO 9
<211> LENGTH: 84
<212> TYPE: PRT
<213> ORGANISM: Adenovirus

<400> SEQUENCE: 9

Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
            20                  25                  30

Thr Val Val Phe Arg Pro Pro Gly Asp Asn Thr Asp Gly Gly Ala Ala
        35                  40                  45

Ala Ala Ala Gly Gly Ser Gln Ala Ala Ala Gly Ala Glu Pro Met
    50                  55                  60

Glu Pro Glu Ser Arg Pro Gly Pro Ser Gly Met Asn Val Val Gln Gln
65                  70                  75                  80

Pro Pro Pro Pro

<210> SEQ ID NO 10
<211> LENGTH: 13
<212> TYPE: DNA
<213> ORGANISM: Adenovirus

<400> SEQUENCE: 10
caggtggctg aac                                                       13

<210> SEQ ID NO 11
<211> LENGTH: 23
<212> TYPE: DNA
<213> ORGANISM: Adenovirus

<400> SEQUENCE: 11
tccttgcatt tgggtaacag gag                                            23

<210> SEQ ID NO 12
<211> LENGTH: 23
<212> TYPE: DNA
<213> ORGANISM: Adenovirus

<400> SEQUENCE: 12
acactaagat attgcttgag ccc                                            23

<210> SEQ ID NO 13

```
<211> LENGTH: 33
<212> TYPE: DNA
<213> ORGANISM: Adenovirus

<400> SEQUENCE: 13
gtcttatgta gttttgtatc tgttttgcag cag                               33

<210> SEQ ID NO 14
<211> LENGTH: 13
<212> TYPE: DNA
<213> ORGANISM: Adenovirus

<400> SEQUENCE: 14
gaggtactga aat                                                    13

<210> SEQ ID NO 15
<211> LENGTH: 44
<212> TYPE: DNA
<213> ORGANISM: Artificial Sequence
<220> FEATURE:
<223> OTHER INFORMATION: Primer

<400> SEQUENCE: 15
ccacctcgag ttaattaaca tcatcaataa tataccttat tttg                   44

<210> SEQ ID NO 16
<211> LENGTH: 34
<212> TYPE: DNA
<213> ORGANISM: Artificial Sequence
<220> FEATURE:
<223> OTHER INFORMATION: Primer

<400> SEQUENCE: 16
gtgggtttaa acggatttgg tcagggaaaa catg                              34

<210> SEQ ID NO 17
<211> LENGTH: 46
<212> TYPE: DNA
<213> ORGANISM: Artificial Sequence
<220> FEATURE:
<223> OTHER INFORMATION: Primer

<400> SEQUENCE: 17
ccttgcattt gggtaataga agaggagtgt tcctacctta ccaatg                 46

<210> SEQ ID NO 18
<211> LENGTH: 46
<212> TYPE: DNA
<213> ORGANISM: Artificial Sequence
<220> FEATURE:
<223> OTHER INFORMATION: Primer

<400> SEQUENCE: 18
cattggtaag gtaggaacac tcctcttcta ttacccaaat gcaagg                 46

<210> SEQ ID NO 19
<211> LENGTH: 36
<212> TYPE: DNA
<213> ORGANISM: Artificial Sequence
<220> FEATURE:
<223> OTHER INFORMATION: Primer

<400> SEQUENCE: 19
cttgcatttg ggtaacagga gggggtgtt cctacc                             36
```

```
<210> SEQ ID NO 20
<211> LENGTH: 36
<212> TYPE: DNA
<213> ORGANISM: Artificial Sequence
<220> FEATURE:
<223> OTHER INFORMATION: Primer

<400> SEQUENCE: 20
ggtaggaaca cccccctcct gttacccaaa tgcaag                              36

<210> SEQ ID NO 21
<211> LENGTH: 32
<212> TYPE: DNA
<213> ORGANISM: Artificial Sequence
<220> FEATURE:
<223> OTHER INFORMATION: Primer

<400> SEQUENCE: 21
ctaagatatt gctggaaccc gagagcatgt cc                                  32

<210> SEQ ID NO 22
<211> LENGTH: 32
<212> TYPE: DNA
<213> ORGANISM: Artificial Sequence
<220> FEATURE:
<223> OTHER INFORMATION: Primer

<400> SEQUENCE: 22
ggacatgctc tcgggttcca gcaatatctt ag                                  32

<210> SEQ ID NO 23
<211> LENGTH: 28
<212> TYPE: DNA
<213> ORGANISM: Artificial Sequence
<220> FEATURE:
<223> OTHER INFORMATION: Primer

<400> SEQUENCE: 23
catttgggta acagaagagg ggtgttcc                                       28

<210> SEQ ID NO 24
<211> LENGTH: 28
<212> TYPE: DNA
<213> ORGANISM: Artificial Sequence
<220> FEATURE:
<223> OTHER INFORMATION: Primer

<400> SEQUENCE: 24
ggaacacccc tcttctgtta cccaaatg                                       28

<210> SEQ ID NO 25
<211> LENGTH: 33
<212> TYPE: DNA
<213> ORGANISM: Artificial Sequence
<220> FEATURE:
<223> OTHER INFORMATION: Primer

<400> SEQUENCE: 25
gaatgaatgt tgtacaagtc gctgaactgt atc                                 33

<210> SEQ ID NO 26
<211> LENGTH: 33
<212> TYPE: DNA
<213> ORGANISM: Artificial Sequence
<220> FEATURE:
<223> OTHER INFORMATION: Primer
```

-continued

<400> SEQUENCE: 26
gatacagttc agcgacttgt acaacattca ttc                          33

<210> SEQ ID NO 27
<211> LENGTH: 36
<212> TYPE: DNA
<213> ORGANISM: Artificial Sequence
<220> FEATURE:
<223> OTHER INFORMATION: Primer

<400> SEQUENCE: 27
gtggctgaac tgtatccata actgagacgc attttg                       36

<210> SEQ ID NO 28
<211> LENGTH: 36
<212> TYPE: DNA
<213> ORGANISM: Artificial Sequence
<220> FEATURE:
<223> OTHER INFORMATION: Primer

<400> SEQUENCE: 28
caaaatgcgt ctcagttatg gatacagttc agccac                       36

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
gcctgctact gttgtcttcc g                                       21

<210> SEQ ID NO 30
<211> LENGTH: 19
<212> TYPE: DNA
<213> ORGANISM: Artificial Sequence
<220> FEATURE:
<223> OTHER INFORMATION: Primer

<400> SEQUENCE: 30 caccccctc ctgtacaac                                           19

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
gacatgctct cgggctgtac aac                                     23

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
caaacgagtt ggtgctcatg                                         20

<210> SEQ ID NO 33
<211> LENGTH: 38

```
<212> TYPE: DNA
<213> ORGANISM: Artificial Sequence
<220> FEATURE:
<223> OTHER INFORMATION: Primer

<400> SEQUENCE: 33
ctcgaggaat tcgccaccat ggagcgaaga aacccatc                              38

<210> SEQ ID NO 34
<211> LENGTH: 33
<212> TYPE: DNA
<213> ORGANISM: Artificial Sequence
<220> FEATURE:
<223> OTHER INFORMATION: Primer

<400> SEQUENCE: 34
cacttctaga tcaatctgta tcttcatcgc tag                                   33

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ggagatttgg acggtcttgg                                                  20

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
ggatcccatc acattttgac g                                                21

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37
catccatgga ggtttgggc                                                   19

<210> SEQ ID NO 38
<211> LENGTH: 21
<212> TYPE: DNA
<213> ORGANISM: Artificial Sequence
<220> FEATURE:
<223> OTHER INFORMATION: Primer

<400> SEQUENCE: 38
ccttaaaaga agcgtttcca c                                                21

<210> SEQ ID NO 39
<211> LENGTH: 28
<212> TYPE: DNA
<213> ORGANISM: Artificial Sequence
<220> FEATURE:
<223> OTHER INFORMATION: Primer

<400> SEQUENCE: 39
```

```
catttgggta acgggagggg ggtgttcc                                          28
```

<210> SEQ ID NO 40
<211> LENGTH: 28
<212> TYPE: DNA
<213> ORGANISM: Artificial Sequence
<220> FEATURE:
<223> OTHER INFORMATION: Primer

<400> SEQUENCE: 40

```
ggaacacccc cctcccgtta cccaaatg                                          28
```

<210> SEQ ID NO 41
<211> LENGTH: 35938
<212> TYPE: DNA
<213> ORGANISM: Adenovirus

<400> SEQUENCE: 41

```
catcatcaat aatataccttt attttggatt gaagccaata tgataatgag ggggtggagt      60
ttgtgacgtg gcgcgggcg tgggaacggg gcgggtgacg tagtagtgtg gcggaagtgt       120
gatgttgcaa gtgtggcgga acacatgtaa gcgacggatg tggcaaaagt gacgttttg       180
gtgtgcgccg tgtacacag gaagtgacaa ttttcgcgcg gttttaggcg gatgttgtag       240
taaatttggg cgtaaccgag taagatttgg ccattttcgc gggaaaactg aataagagga     300
agtgaaatct gaataatttt gtgttactca tagcgcgtaa tatttgtcta gggccgcggg      360
gactttgacc gtttacgtgg agactcgccc aggtgttttt ctcaggtgtt ttccgcgttc      420
cgggtcaaag ttggcgtttt attattatag tcagctgacg tgtagtgtat ttatacccgg      480
tgagttcctc aagaggccac tcttgagtgc cagcgagtag agttttctcc tccgagccgc      540
tccgacaccg ggactgaaaa tgagacatat tatctgccac ggaggtgtta ttaccgaaga      600
aatggccgcc agtcttttgg accagctgat cgaagaggta ctggctgata atcttccacc      660
tcctagccat tttgaaccac ctacccttca cgaactgtat gatttagacg tgacggcccc      720
cgaagatccc aacgaggagg cggtttcgca gatttttccc gactctgtaa tgttggcggt      780
gcaggaaggg attgacttac tcactttttcc gccggcgccc ggttctccgg agccgcctca      840
ccttttcccgg cagcccgagc agccggagca gagagccttg ggtccggttt ctatgccaaa     900
ccttgtaccg gaggtgatcg atcttacctg ccacgaggct ggcttccac ccagtgacga      960
cgaggatgaa gagggtgagg agtttgtgtt agattatgtg gagcaccccg ggcacggttg     1020
caggtcttgt cattatcacc ggaggaatac gggggaccca gatattatgt gttcgctttg     1080
ctatatgagg acctgtggca tgtttgtcta cagtaagtga aaattatggg cagtgggtga     1140
tagagtggtg ggtttggtgt ggtaattttt tttttaattt ttacagtttt gtggtttaaa     1200
gaattttgta ttgtgatttt tttaaaaggt cctgtgtctg aacctgagcc tgagcccgag     1260
ccagaaccgg agcctgcaag acctaccgc cgtcctaaaa tggcgcctgc tatcctgaga     1320
cgcccgacat cacctgtgtc tagagaatgc aatagtagta cggatagctg tgactccggt     1380
ccttctaaca cacctcctga gatacacccg gtggtcccgc tgtgccccat taaaccagtt     1440
gccgtgagag ttggtgggcg tcgccaggct gtggaatgta tcgaggactt gcttaacgag     1500
cctgggcaac ctttggactt gagctgtaaa cgccccaggc cataaggtgt aaacctgtga     1560
ttgcgtgtgt ggttaacgcc tttgtttgct gaatgagttg atgtaagttt aataaagggt     1620
gagataatgt ttaacttgca tggcgtgtta aatgggcgg ggcttaaagg gtatataatg      1680
cgccgtgggc taatcttggt tacatctgac ctcatggagg cttgggagtg tttggaagat     1740
```

```
tttctgctg tgcgtaactt gctggaacag agctctaaca gtacctcttg gttttggagg      1800
tttctgtggg gctcatccca ggcaaagtta gtctgcagaa ttaaggagga ttacaagtgg      1860
gaatttgaag agcttttgaa atcctgtggt gagctgtttg attctttgaa tctgggtcac      1920
caggcgcttt tccaagagaa ggtcatcaag actttggatt tttccacacc ggggcgcgct      1980
gcggctgctg ttgctttttt gagttttata aaggataaat ggagcgaaga aacccatctg      2040 agcgggggt acctgctgga ttttctggcc atgcatctgt ggagagcggt tgtgagacac      2100
aagaatcgcc tgctactgtt gtcttccgtc cgcccggcga taataccgac ggaggagcag      2160
cagcagcagc aggaggaagc caggcggcgg cggcaggagc agagcccatg gaacccgaga      2220
gccggcctgg accctcggga atgaatgttg tacaggtggc tgaactgtat ccagaactga      2280
gacgcatttt gacaattaca gaggatgggc agggctaaa gggggtaaag agggagcggg       2340
gggcttgtga ggctacagag gaggctagga atctagcttt tagcttaatg accagacacc      2400
gtcctgagtg tattactttt caacagatca aggataattg cgctaatgag cttgatctgc      2460
tggcgcagaa gtattccata gagcagctga ccacttactg gctgcagcca ggggatgatt      2520
ttgaggaggc tattagggta tatgcaaagg tggcacttag gccagattgc aagtacaaga      2580
tcagcaaact tgtaaatatc aggaattgtt gctacatttc tgggaacggg gccgaggtgg      2640
agatagatac ggaggatagg gtggccttta gatgtagcat gataaatatg tggccggggg      2700
tgcttggcat ggacgggtg gttattatga atgtaaggtt tactggcccc aattttagcg        2760
gtacggtttt cctggccaat accaaccta tcctacacgg tgtaagcttc tatgggttta       2820
acaatacctg tgtggaagcc tggaccgatg taagggttcg gggctgtgcc ttttactgct      2880
gctggaaggg ggtggtgtgt cgccccaaaa gcagggcttc aattaagaaa tgcctctttg      2940
aaaggtgtac cttgggtatc ctgtctgagg gtaactccag ggtgcgccac aatgtggcct     3000
ccgactgtgg ttgcttcatg ctagtgaaaa gcgtggctgt gattaagcat aacatggtat     3060
gtggcaactg cgaggacagg gcctctcaga tgctgacctg ctcggacggc aactgtcacc     3120
tgctgaagac cattcacgta gccagccact ctcgcaaggc ctggccagtg tttgagcata     3180
acatactgac ccgctgttcc ttgcatttgg gtaacaggag ggggtgttc ctaccttacc      3240 aatgcaattt gagtcacact aagatattgc ttgagcccga gagcatgtcc aaggtgaacc     3300
tgaacggggt gtttgacatg accatgaaga tctggaaggt gctgaggtac gatgagaccc     3360
gcaccaggtg cagaccctgc gagtgtggcg gtaaacatat taggaaccag cctgtgatgc     3420
tggatgtgac cgaggagctg aggcccgatc acttggtgct ggcctgcacc cgcgctgagt     3480
ttggctctag cgatgaagat acagattgag gtactgaaat gtgtgggcgt ggcttaaggg     3540
tgggaaagaa tatataaggt gggggtctta tgtagttttg tatctgtttt gcagcagccg     3600
ccgccgccat gagcaccaac tcgtttgatg gaagcattgt gagctcatat ttgacaacgc     3660
gcatgccccc atgggccggg gtgcgtcaga atgtgatggg ctccagcatt gatggtcgcc     3720
ccgtcctgcc cgcaaactct actaccttga cctacgagac cgtgtctgga acgccgttgg     3780
agactgcagc ctccgccgcc gcttcagccg ctgcagccac cgcccgcggg attgtgactg     3840
actttgcttt cctgagcccg cttgcaagca gtgcagcttc ccgttcatcc gcccgcgatg     3900
acaagttgac ggctctttttg gcacaattgg attctttgac ccgggaactt aatgtcgttt     3960
ctcagcagct gttggatctg cgccagcagg tttctgccct gaaggcttcc tcccctccca     4020
atgcggttta aacataaat aaaaaaccag actctgtttg gatttggatc aagcaagtgt      4080
```

-continued

```
cttgctgtct ttatttaggg gttttgcgcg cgcggtaggc ccgggaccag cggtctcggt    4140
cgttgagggt cctgtgtatt ttttccagga cgtggtaaag gtgactctgg atgttcagat    4200
acatgggcat aagcccgtct ctggggtgga ggtagcacca ctgcagagct tcatgctgcg    4260
gggtggtgtt gtagatgatc cagtcgtagc aggagcgctg ggcgtggtgc ctaaaaatgt    4320
ctttcagtag caagctgatt gccaggggca ggcccttggt gtaagtgttt acaaagcggt    4380
taagctggga tgggtgcata cgtggggata tgagatgcat cttggactgt attttttaggt   4440 tggctatgtt cccagccata tccctccggg gattcatgtt gtgcagaacc accagcacag    4500
tgtatccggt gcacttggga aatttgtcat gtagcttaga aggaaatgcg tggaagaact    4560
tggagacgcc cttgtgacct ccaagatttt ccatgcattc gtccataatg atggcaatgg    4620
gcccacgggc ggcggcctgg gcgaagatat ttctgggatc actaacgtca tagttgtgtt    4680
ccaggatgag atcgtcatag gccatttttta caaagcgcgg gcggagggtg ccagactgcg    4740
gtataatggt tccatccggc ccaggggcgt agttaccctc acagatttgc atttcccacg    4800
ctttgagttc agatgggggg atcatgtcta cctgcggggc gatgaagaaa acggtttccg    4860
gggtagggga gatcagctgg gaagaaagca ggttcctgag cagctgcgac ttaccgcagc    4920
cggtgggccc gtaaatcaca cctattaccg ggtgcaactg gtagttaaga gagctgcagc    4980
tgccgtcatc cctgagcagg ggggccactt cgttaagcat gtccctgact cgcatgtttt    5040
ccctgaccaa atccgccaga aggcgctcgc cgcccagcga tagcagttct tgcaaggaag    5100
caaagttttt caacggtttg agaccgtccg ccgtaggcat gcttttgagc gtttgaccaa    5160
gcagttccag gcggtcccac agctcggtca cctgctctac ggcatctcga tccagcatat    5220
ctcctcgttt cgcgggttgg ggcggctttc gctgtacggc agtagtcggt gctcgtccag    5280
acgggccagg gtcatgtctt tccacgggcg cagggtcctc gtcagcgtag tctgggtcac    5340
ggtgaagggg tgcgctccgg gctgcgcgct ggccagggtg cgcttgaggc tggtcctgct    5400
ggtgctgaag cgctgccggt cttcgccctg cgcgtcggcc aggtagcatt tgaccatggt    5460
gtcatagtcc agcccctccg cggcgtggcc cttggcgcgc agcttgccct tggaggaggc    5520
gccgcacgag gggcagtgca gacttttgag ggcgtagagc ttgggcgcga gaaataccga    5580
ttccggggag taggcatccg cgccgcaggc cccgcagacg gtctcgcatt ccacgagcca    5640
ggtgagctct ggccgttcgg ggtcaaaaac caggtttccc ccatgctttt tgatgcgttt    5700
cttacctctg gtttccatga gccggtgtcc acgctcggtg acgaaaaggc tgtccgtgtc    5760
cccgtataca gacttgagag gcctgtcctc gagcggtgtt ccgcggtcct cctcgtatag    5820
aaactcggac cactctgaga caaaggctcg cgtccaggcc agcacgaagg aggctaagtg    5880
ggaggggtag cggtcgttgt ccactagggg gtccactcgc tccagggtgt gaagacacat    5940
gtcgccctct tcggcatcaa ggaaggtgat tggtttgtag gtgtaggcca cgtgaccggg    6000
tgttcctgaa gggggctat aaaagggggt ggggcgcgt tcgtcctcac tctcttccgc    6060
atcgctgtct gcgagggcca gctgttgggg tgagtactcc ctctgaaaag cgggcatgac    6120
ttctgcgcta agattgtcag tttccaaaaa cgaggaggat ttgatattca cctggcccgc    6180
ggtgatgcct ttgagggtgg ccgcatccat ctggtcagaa aagacaatct ttttgttgtc    6240
aagcttggtg gcaaacgacc cgtagagggc gttggacagc aacttggcga tggagcgcag    6300
ggtttggttt ttgtcgcgat cggcgcgctc cttggccgcg atgtttagct gcacgtattc    6360
gcgcgcaacg caccgccatt cgggaaagac ggtggtgcgc tcgtcgggca ccaggtgcac    6420
gcgccaaccg cggttgtgca gggtgacaag gtcaacgctg gtggctacct ctccgcgtag    6480
```

```
gcgctcgttg gtccagcaga ggcggccgcc cttgcgcgag cagaatggcg gtaggggtc    6540
tagctgcgtc tcgtccgggg ggtctgcgtc cacggtaaag accccgggca gcaggcgcgc    6600
gtcgaagtag tctatcttgc atccttgcaa gtctagcgcc tgctgccatg cgcgggcggc    6660
aagcgcgcgc tcgtatgggt tgagtggggg accccatggc atgggtggg tgagcgcgga    6720
ggcgtacatg ccgcaaatgt cgtaaacgta gaggggctct ctgagtattc caagatatgt    6780
agggtagcat cttccaccgc ggatgctggc gcgcacgtaa tcgtatagtt cgtgcgaggg    6840
agcgaggagg tcgggaccga ggttgctacg ggcgggctgc tctgctcgga agactatctg    6900
cctgaagatg gcatgtgagt tggatgatat ggttggacgc tggaagacgt tgaagctggc    6960
gtctgtgaga cctaccgcgt cacgcacgaa ggaggcgtag gagtcgcgca gcttgttgac    7020
cagctcggcg gtgacctgca cgtctagggc gcagtagtcc agggtttcct tgatgatgtc    7080
atacttatcc tgtcccttt tttccacag ctcgcggttg aggacaaact cttcgcggtc     7140
tttccagtac tcttggatcg gaaacccgtc ggcctccgaa cggtaagagc ctagcatgta    7200
gaactggttg acggcctggt aggcgcagca tcccttttct acgggtagcg cgtatgcctg    7260
cgcggccttc cggagcgagg tgtgggtgag cgcaaaggtg tccctgacca tgactttgag    7320
gtactggtat ttgaagtcag tgtcgtcgca tccgccctgc tcccagagca aaaagtccgt    7380
gcgcttttg gaacgcggat ttggcaggc gaaggtgaca tcgttgaaga gtatctttcc     7440
cgcgcgaggc ataaagttgc gtgtgatgcg gaagggtccc ggcacctcgg aacggttgtt    7500
aattacctgg gcggcgagca cgatctcgtc aaagccgttg atgttgtggc ccacaatgta    7560
aagttccaag aagcgcggga tgcccttgat ggaaggcaat ttttaagtt cctcgtaggt    7620
gagctcttca ggggagctga gcccgtgctc tgaaagggcc cagtctgcaa gatgagggtt    7680
ggaagcgacg aatgagctcc acaggtcacg ggccattagc atttgcaggt ggtcgcgaaa    7740
ggtcctaaac tggcgaccta tggccatttt ttctggggtg atgcagtaga aggtaagcgg    7800
gtcttgttcc cagcggtccc atccaaggtt cgcggctagg tctcgcgcgg cagtcactag    7860
aggctcatct ccgccgaact tcatgaccag catgaagggc acgagctgct tcccaaaggc    7920
ccccatccaa gtataggtct ctacatcgta ggtgacaaag agacgctcgg tgcgaggatg    7980
cgagccgatc gggaagaact ggatctcccg ccaccaattg gaggagtggc tattgatgtg    8040
gtgaaagtag aagtccctgc gacgggccga acactcgtgc tggcttttgt aaaaacgtgc    8100
gcagtactgg cagcggtgca cgggctgtac atcctgcacg aggttgacct gacgaccgcg    8160
cacaaggaag cagagtggga atttgagccc ctcgcctggc gggtttggct ggtggtcttc    8220
tacttcggct gcttgtcctt gaccgtctgg ctgctcgagg ggagttacgg tggatcggac    8280
caccacgccg cgcgagccca agtccagat gtccgcgcgc ggcggtcgga gcttgatgac     8340
aacatcgcgc agatgggagc tgtccatggt ctggagctcc cgcggcgtca ggtcaggcgg    8400
gagctcctgc aggtttacct cgcatagacg ggtcagggcg cgggctagat ccaggtgata    8460
cctaatttcc aggggctggt tggtggcggc gtcgatggct tgcaagaggc cgcatccccg    8520
cggcgcgact acggtaccgc gcggcgggcg gtgggccgcg ggggtgtcct tggatgatgc    8580
atctaaaagc ggtgacgcgg gcgagccccc ggaggtaggg ggggctccgg acccgccggg    8640
agaggggggca ggggcacgtc ggcgccgcgc gcgggcagga gctggtgctg cgcgcgtagg    8700
ttgctggcga acgcgacgac gcggcggttg atctcctgaa tctggcgcct ctgcgtgaag    8760
acgacgggcc cggtgagctt gagcctgaaa gagagttcga cagaatcaat ttcggtgtcg    8820
```

```
ttgacggcgg cctggcgcaa aatctcctgc acgtctcctg agttgtcttg ataggcgatc   8880
tcggccatga actgctcgat ctcttcctcc tggagatctc cgcgtccggc tcgctccacg   8940
gtggcggcga ggtcgttgga aatgcgggcc atgagctgcg agaaggcgtt gaggcctccc   9000
tcgttccaga cgcggctgta gaccacgccc ccttcggcat cgcggcgcg catgaccacc    9060 tgcgcgagat tgagctccac gtgccgggcg aagacggcgt agtttcgcag cgcgctgaaag  9120 aggtagttga gggtggtggc ggtgtgttct gccacgaaga agtacataac ccagcgtcgc   9180
aacgtggatt cgttgatatc ccccaaggcc tcaaggcgct ccatggcctc gtagaagtcc   9240
acggcgaagt tgaaaaactg ggagttgcgc gccgacacgg ttaactcctc ctccagaaga   9300
cggatgagct cggcgacagt gtcgcgcacc tcgcgctcaa aggctacagg ggcctcttct   9360
tcttcttcaa tctcctcttc cataaggggcc tccccttctt cttcttctgg cggcggtggg   9420
ggagggggga cacggcggcg acgacggcgc accgggaggc ggtcgacaaa gcgctcgatc   9480
atctccccgc ggcgacggcg catggtctcg gtgacggcgc ggccgttctc gcgggggcgc   9540
agttggaaga cgccgcccgt catgtcccgg ttatgggttg gcgggggct gccatgcggc    9600 agggatacgg cgctaacgat gcatctcaac aattgttgtg taggtactcc gccgccgagg   9660
gacctgagcg agtccgcatc gaccggatcg gaaaacctct cgagaaaggc gtctaaccag   9720
tcacagtcgc aaggtaggct gagcaccgtg gcgggcggca gcgggcggcg gtcggggttg   9780
tttctggcgg aggtgctgct gatgatgtaa ttaaagtagg cggtcttgag acggcggatg   9840
gtcgacagaa gcaccatgtc cttgggtccg gcctgctgaa tgcgcaggcg gtcggccatg   9900
ccccaggctt cgttttgaca tcggcgcagg tctttgtagt agtcttgcat gagcctttct   9960
accggcactt cttcttctcc ttcctcttgt cctgcatctc ttgcatctat cgctgcggcg  10020
gcggcggagt ttggccgtag gtggcgccct cttcctccca tgcgtgtgac cccgaagccc  10080
ctcatcggct gaagcagggc taggtcggcg acaacgcgct cggctaatat ggcctgctgc  10140
acctgcgtga gggtagactg gaagtcatcc atgtccacaa agcggtggta tgcgcccgtg  10200
ttgatggtgt aagtgcagtt ggccataacg gaccagttaa cggtctggtg acccggctgc  10260
gagagctcgg tgtacctgag acgcgagtaa gccctcgagt caaatacgta gtcgttgcaa  10320
gtccgcacca ggtactggta tcccaccaaa aagtgcggcg gcggctggcg gtagaggggc  10380
cagcgtaggg tggccggggc tccggggggcg agatcttcca acataaggcg atgatatccg  10440
tagatgtacc tggacatcca ggtgatgccg gcggcggtgg tggaggcgcg cggaaagtcg  10500
cggacgcggt tccagatgtt gcgcagcggc aaaaagtgct ccatggtcgg gacgctctgg  10560
ccggtcaggc gcgcgcaatc gttgacgctc tagaccgtgc aaaaggagag cctgtaagcg  10620
ggcactcttc cgtggtctgg tggataaatt cgcaagggta tcatggcgga cgaccggggt  10680
tcgagccccg tatccggccg tccgccgtga tccatgcggt taccgccgc gtgtcgaacc   10740 caggtgtgcg acgtcagaca acgggggagt gctccttttg gcttccttcc aggcgcggcg  10800
gctgctgcgc tagctttttt ggccactggc cgcgcgcagc gtaagcggtt aggctggaaa  10860
gcgaaagcat taagtggctc gctccctgta gccggagggt tatttccaa gggttgagtc    10920 gcgggacccc cggttcgagt ctcggaccgg cggactgcg cgaacgggg gtttgcctcc     10980 ccgtcatgca agacccgct tgcaaattcc tccggaaaca gggacgagcc ctttttttgc    11040
ttttcccaga tgcatccggt gctgcggcag atgcgccccc ctcctcagca gcggcaagag  11100
caagagcagc ggcagacatg cagggcaccc tcccctcctc ctaccgcgtc aggaggggcg  11160
acatccgcgg ttgacgcggc agcagatggt gattacgaac ccccgcggcg ccgggcccgg  11220
```

```
cactacctgg acttggagga gggcgagggc ctggcgcggc taggagcgcc ctctcctgag    11280
cggtacccaa gggtgcagct gaagcgtgat acgcgtgagg cgtacgtgcc gcggcagaac    11340
ctgtttcgcg accgcgaggg agaggagccc gaggagatgc gggatcgaaa gttccacgca    11400
gggcgcgagc tgcggcatgg cctgaatcgc gagcggttgc tgcgcgagga ggactttgag    11460
cccgacgcgc gaaccgggat tagtcccgcg cgcgcacacg tggcggccgc cgacctggta    11520
accgcatacg agcagacggt gaaccaggag attaactttc aaaaaagctt taacaaccac    11580
gtgcgtacgc ttgtggcgcg cgaggaggtg gctataggac tgatgcatct gtgggacttt    11640
gtaagcgcgc tggagcaaaa cccaaatagc aagccgctca tggcgcagct gttccttata    11700
gtgcagcaca gcagggacaa cgaggcattc agggatgcgc tgctaaacat agtagagccc    11760
gagggccgct ggctgctcga tttgataaac atcctgcaga gcatagtggt gcaggagcgc    11820
agcttgagcc tggctgacaa ggtggccgcc atcaactatt ccatgcttag cctgggcaag    11880
ttttacgccc gcaagatata ccataccccct tacgttccca tagacaagga ggtaaagatc    11940
gaggggttct acatgcgcat ggcgctgaag gtgcttacct tgagcgacga cctgggcgtt    12000
tatcgcaacg agcgcatcca caaggccgtg agcgtgagcc ggcggcgcga gctcagcgac    12060
cgcgagctga tgcacagcct gcaaagggcc ctggctggca cgggcagcgg cgatagagag    12120
gccgagtcct actttgacgc gggcgctgac ctgcgctggg ccccaagccg acgcgccctg    12180
gaggcagctg gggccggacc tgggctggcg gtggcacccg cgcgcgctgg caacgtcggc    12240
ggcgtggagg aatatgacga ggacgatgag tacgagccag aggacggcga gtactaagcg    12300
gtgatgtttc tgatcagatg atgcaagacg caacggaccc ggcggtgcgg gcggcgctgc    12360
agagccagcc gtccggcctt aactccacgg acgactggcg ccaggtcatg gaccgcatca    12420
tgtcgctgac tgcgcgcaat cctgacgcgt tccggcagca gccgcaggcc aaccggctct    12480
ccgcaattct ggaagcggtg gtcccggcgc gcgcaaaccc cacgcacgag aaggtgctgg    12540
cgatcgtaaa cgcgctggcc gaaaacaggg ccatccggcc cgacgaggcc ggcctggtct    12600
acgacgcgct gcttcagcgc gtggctcgtt acaacagcgg caacgtgcag accaacctgg    12660
accggctggt gggggatgtg cgcgaggccg tggcgcagcg tgagcgcgcg cagcagcagg    12720
gcaacctggg ctccatggtt gcactaaacg ccttcctgag tacacagccc gccaacgtgc    12780
cgcggggaca ggaggactac accaactttg tgagcgcact gcggctaatg gtgactgaga    12840
caccgcaaag tgaggtgtac cagtctgggc cagactattt tttccagacc agtagacaag    12900
gcctgcagac cgtaaacctg agccaggctt tcaaaaactt gcaggggctg tggggggtgc    12960
gggctcccac aggcgaccgc gcgaccgtgt ctagcttgct gacgcccaac tcgcgcctgt    13020
tgctgctgct aatagcgccc ttcacggaca gtggcagcgt gtcccgggac acatacctag    13080
gtcacttgct gacactgtac cgcgaggcca taggtcaggc gcatgtggac gagcatactt    13140
tccaggagat tacaagtgtc agccgcgcgc tgggcagga ggacacgggc agcctggagg    13200
caaccctaaa ctacctgctg accaaccggc ggcagaagat cccctcgttg cacagtttaa    13260
acagcgagga ggagcgcatt ttgcgctacg tgcagcagag cgtgagcctt aacctgatgc    13320
gcgacgggt aacgcccagc gtggcgctgg acatgaccgc gcgcaacatg gaaccgggca    13380
tgtatgcctc aaaccggccg tttatcaacc gcctaatgga ctacttgcat cgcgcggccg    13440
ccgtgaaccc cgagtatttc accaatgcca tcttgaaccc gcactggcta ccgcccctg    13500
gtttctacac cggggattc gaggtgcccg agggtaacga tggattcctc tgggacgaca    13560
```

```
tagacgacag cgtgttttcc ccgcaaccgc agaccctgct agagttgcaa cagcgcgagc    13620
aggcagaggc ggcgctgcga aaggaaagct tccgcaggcc aagcagcttg tccgatctag    13680
gcgctgcggc cccgcggtca gatgctagta gcccatttcc aagcttgata gggtctctta    13740
ccagcactcg caccacccgc ccgcgcctgc tgggcgagga ggagtaccta acaactcgc     13800 tgctgcagcc gcagcgcgaa aaaaacctgc ctccggcatt tcccaacaac gggatagaga    13860
gcctagtgga caagatgagt agatggaaga cgtacgcgca ggagcacagg gacgtgccag    13920
gcccgcgccc gcccacccgt cgtcaaaggc acgaccgtca gcggggtctg gtgtgggagg    13980
acgatgactc ggcagacgac agcagcgtcc tggatttggg agggagtggc aacccgtttg    14040
cgcaccttcg ccccaggctg gggagaatgt tttaaaaaaa aaaagcatg  atgcaaaata    14100 aaaaactcac caaggccatg gcaccgagcg ttggttttct tgtattcccc ttagtatgcg    14160
gcgcgcggcg atgtatgagg aaggtcctcc tccctcctac gagagtgtgg tgagcgcggc    14220
gccagtggcg gcggcgctgg gttctcccctt cgatgctccc ctggaccgc  cgtttgtgcc    14280 tccgcggtac ctgcggccta ccgggggggag aaacagcatc cgttactctg agttggcacc    14340
cctattcgac accacccgtg tgtacctggt ggacaacaag tcaacggatg tggcatccct    14400
gaactaccag aacgaccaca gcaactttct gaccacggtc attcaaaaca atgactacag    14460 cccggggggag gcaagcacac agaccatcaa tcttgacgac cggtcgcact ggggcggcga    14520
cctgaaaacc atcctgcata ccaacatgcc aaatgtgaac gagttcatgt ttaccaataa    14580
gtttaaggcg cgggtgatgg tgtcgcgctt gcctactaag gacaatcagg tggagctgaa    14640
atacgagtgg gtggagttca cgctgcccga gggcaactac tccgagacca tgaccataga    14700
ccttatgaac aacgcgatcg tggagcacta cttgaaagtg ggcagacaga acggggttct    14760
ggaaagcgac atcggggtaa agtttgacac ccgcaacttc agactggggt ttgacccccgt    14820 cactggtctt gtcatgcctg ggtatatac  aaacgaagcc ttccatccag acatcatttt    14880
gctgccagga tgcggggtgg acttcaccca gcccgcctg  agcaacttgt tgggcatccg    14940
caagcggcaa cccttccagg agggctttag gatcacctac gatgatctgg agggtggtaa    15000
cattcccgca ctgttggatg tggacgccta ccaggcgagc ttgaaagatg acaccgaaca    15060 gggcggggggt ggcgcaggcg gcagcaacag cagtggcagc ggcgcggaag agaactccaa    15120
cgcggcagcc gcggcaatgc agccggtgga ggacatgaac gatcatgcca ttcgcggcga    15180 caccttgcc  acacgggctg aggagaagcg cgctgaggcc gaagcagcgg ccgaagctgc    15240
cgcccccgct gcgcaacccg aggtcgagaa gcctcagaag aaaccggtga tcaaacccct    15300
gacagaggac agcaagaaac gcagttacaa cctaataagc aatgacagca ccttcacccca    15360 gtaccgcagc tggtaccttg catacaacta cggcgaccct cagaccggaa tccgctcatg    15420
gaccctgctt tgcactcctg acgtaacctg cggctcggag caggtctact ggtcgttgcc    15480
agacatgatg caagacccg  tgaccttccg ctccacgcgc cagatcagca actttccggt    15540
ggtgggcgcc gagctgttgc ccgtgcactc caagagcttc tacaacgacc aggccgtcta    15600
ctcccaactc atccgccagt ttacctctct gacccacgtg ttcaatcgct ttcccgagaa    15660
ccagatttgg gcgcgcccgc cagccccac  catcaccacc gtcagtgaaa cgttcctgc     15720 tctcacagat cacgggacgc taccgctgcg caacagcatc ggaggagtcc agcgagtgac    15780
cattactgac gccagacgcc gcacctgccc ctacgtttac aaggccctgg gcatagtctc    15840
gccgcgcgtc ctatcgagcc gcacttttg  agcaagcatg tccatcctta tatcgcccag    15900
caataacaca ggctggggcc tgcgcttccc aagcaagatg tttggcgggg ccaagaagcg    15960
```

```
ctccgaccaa cacccagtgc gcgtgcgcgg gcactaccgc gcgccctggg gcgcgcacaa    16020
acgcggccgc actgggcgca ccaccgtcga tgacgccatc gacgcggtgg tggaggaggc    16080
gcgcaactac acgcccacgc cgccaccagt gtccacagtg gacgcggcca ttcagaccgt    16140
ggtgcgcgga gcccggcgct atgctaaaat gaagagacgg cggaggcgcg tagcacgtcg    16200
ccaccgccgc cgacccggca ctgccgccca acgcgcggcg gcggccctgc ttaaccgcgc    16260
acgtcgcacc ggccgacggg cggccatgcg ggccgctcga aggctggccg cgggtattgt    16320
cactgtgccc cccaggtcca ggcgacgagc ggccgccgca gcagccgcgg ccattagtgc    16380
tatgactcag ggtcgcaggg gcaacgtgta ttgggtgcgc gactcggtta gcggcctgcg    16440
cgtgcccgtg cgcacccgcc ccccgcgcaa ctagattgca agaaaaaact acttagactc    16500
gtactgttgt atgtatccag cggcggcggc gcgcaacgaa gctatgtcca agcgcaaaat    16560
caaagaagag atgctccagg tcatcgcgcc ggagatctat ggccccccga agaaggaaga    16620
gcaggattac aagccccgaa agctaaagcg ggtcaaaaag aaaaagaaag atgatgatga    16680
tgaacttgac gacgaggtgg aactgctgca cgctaccgcg cccaggcgac gggtacagtg    16740
gaaaggtcga cgcgtaaaac gtgttttgcg accggcacc accgtagtct ttacgcccgg    16800
tgagcgctcc acccgcacct acaagcgcgt gtatgatgag gtgtacggcg acgaggacct    16860
gcttgagcag gccaacgagc gcctcgggga gtttgcctac ggaaagcggc ataaggacat    16920
gctggcgttg ccgctggacg agggcaaccc aacacctagc ctaaagcccg taacactgca    16980
gcaggtgctg cccgcgcttg caccgtccga agaaaagcgc ggcctaaagc gcgagtctgg    17040
tgacttggca cccaccgtgc agctgatggt acccaagcgc cagcgactgg aagatgtctt    17100
ggaaaaaatg accgtggaac ctgggctgga gcccgaggtc cgcgtgcggc caatcaagca    17160
ggtggcgccg gactgggcg tgcagaccgt ggacgttcag atacccacta ccagtagcac    17220
cagtattgcc accgccacag agggcatgga gacacaaacg tccccggttg cctcagcggt    17280
ggcggatgcc gcggtgcagg cggtcgctgc ggccgcgtcc aagacctcta cggaggtgca    17340
aacggacccg tggatgtttc gcgtttcagc ccccgggcgc ccgcgcggtt cgaggaagta    17400
cggcgccgcc agcgcgctac tgcccgaata tgccctacat ccttccattg cgcctacccc    17460
cggctatcgt ggctacacct accgccccag aagacgagca actacccgac gccgaaccac    17520
cactggaacc cgccgccgcc gtcgccgtcg ccagcccgtg ctggcccga tttccgtgcg    17580 cagggtggct cgcgaaggag gcaggaccct ggtgctgcca acagcgcgct accaccccag    17640
catcgtttaa aagccggtct ttgtggttct tgcagatatg gccctcacct gccgcctccg    17700
tttcccggtg ccgggattcc gaggaagaat gcaccgtagg aggggcatgg ccggccacgg    17760
cctgacgggc ggcatgcgtc gtgcgcacca ccggcggcgg cgcgcgtcgc accgtcgcat    17820
gcgcggcggt atcctgcccc tccttattcc actgatcgcc gcggcgattg cgccgtgcc    17880 cggaattgca tccgtggcct tgcaggcgca gagacactga ttaaaaacaa gttgcatgtg    17940
gaaaaatcaa aataaaaagt ctggactctc acgctcgctt ggtcctgtaa ctattttgta    18000
gaatggaaga catcaacttt gcgtctctgg ccccgcgaca cggctcgcgc cgttcatgg    18060 gaaactggca agatatcggc accagcaata tgagcggtgg cgccttcagc tggggctcgc    18120
tgtggagcgg cattaaaaat ttcggttcca ccgttaagaa ctatggcagc aaggcctgga    18180
acagcagcac aggccagatg ctgagggata agttgaaaga gcaaaatttc caacaaaagg    18240
tggtagatgg cctggcctct ggcattagcg gggtggtgga cctggccaac caggcagtgc    18300
```

```
aaaataagat taacagtaag cttgatcccc gccctcccgt agaggagcct ccaccggccg   18360
tggagacagt gtctccagag gggcgtggcg aaaagcgtcc gcgccccgac agggaagaaa   18420
ctctggtgac gcaaatagac gagcctccct cgtacgagga ggcactaaag caaggcctgc   18480
ccaccacccg tcccatcgcg cccatggcta ccggagtgct gggccagcac acacccgtaa   18540
cgctggacct gcctcccccc gccgacaccc agcagaaacc tgtgctgcca ggcccgaccg   18600
ccgttgttgt aacccgtcct agccgcgcgt ccctgcgccg cgccgccagc ggtccgcgat   18660
cgttgcggcc cgtagccagt ggcaactggc aaagcacact gaacagcatc gtgggtctgg   18720
gggtgcaatc cctgaagcgc cgacgatgct tctgaatagc taacgtgtcg tatgtgtgtc   18780
atgtatgcgt ccatgtcgcc gccagaggag ctgctgagcc gccgcgcgcc cgcttttccaa  18840 gatggctacc ccttcgatga tgccgcagtg gtcttacatg cacatctcgg gccaggacgc   18900
ctcggagtac ctgagccccg ggctggtgca gtttgcccgc gccaccgaga cgtacttcag   18960
cctgaataac aagtttagaa accccacggt ggcgcctacg cacgacgtga ccacagaccg   19020
gtcccagcgt ttgacgctgc ggttcatccc tgtggaccgt gaggatactg cgtactcgta   19080
caaggcgcgg ttcaccctag ctgtgggtga taaccgtgtg ctggacatgg cttccacgta   19140 cttgacatc cgcggcgtgc tggacagggg ccctactttt aagccctact ctggcactgc    19200
ctacaacgcc ctggctccca agggtgcccc aaatccttgc gaatgggatg aagctgctac   19260
tgctcttgaa ataaacctag aagaagagga cgatgacaac gaagacgaag tagacgagca   19320
agctgagcag caaaaaactc acgtatttgg gcaggcgcct tattctggta taaatattac    19380
aaaggagggt attcaaatag gtgtcgaagg tcaaacacct aaatatgccg ataaaacatt    19440
tcaacctgaa cctcaaatag gagaatctca gtggtacgaa actgaaatta atcatgcagc   19500
tgggagagtc cttaaaaaga ctaccccaat gaaaccatgt tacggttcat atgcaaaacc   19560
cacaaatgaa aatggagggc aaggcattct tgtaaagcaa caaaatggaa agctagaaag   19620
tcaagtggaa atgcaatttt tctcaactac tgaggcgacc gcaggcaatg gtgataactt   19680
gactcctaaa gtggtattgt acagtgaaga tgtagatata gaaaccccag acactcatat   19740
ttcttacatg cccactatta aggaaggtaa ctcacgagaa ctaatgggcc aacaatctat   19800
gcccaacagg cctaattaca ttgcttttag ggacaatttt attggtctaa tgtattacaa   19860
cagcacgggg aatatgggtg ttctggcggg ccaagcatcg cagttgaatg ctgttgtaga   19920
tttgcaagac agaaacacag agctttcata ccagcttttg cttgattcca ttggtgatag   19980
aaccaggtac ttttctatgt ggaatcaggc tgttgacagc tatgatccag atgttagaat   20040
tattgaaaat catggaactg aagatgaact tccaaattac tgctttccac tgggaggtgt   20100
gattaataca gagactctta ccaaggtaaa acctaaaaca ggtcaggaaa atggatggga   20160
aaaagatgct acagaatttt cagataaaaa tgaaataaga gttggaaata ttttgccat    20220 ggaaatcaat ctaaatgcca acctgtggag aaatttcctg tactccaaca tagcgctgta   20280
tttgcccgac aagctaaagt acagtccttc caacgtaaaa atttctgata acccaaacac   20340
ctacgactac atgaacaagc gagtggtggc tcccgggtta gtggactgct acattaacct   20400
tggagcacgc tggtccccttg actatatgga caacgtcaac ccatttaacc accaccgcaa   20460
tgctggcctg cgctaccgct caatgttgct gggcaatggt cgctatgtgc ccttccacat   20520
ccaggtgcct cagaagttct ttgccattaa aaacctcctt ctcctgccgg gctcatacac   20580
ctacgagtgg aacttcagga aggatgttaa catggttctg cagagctccc taggaaatga   20640
cctaagggtt gacggagcca gcattaagtt tgatagcatt tgcctttacg ccaccttctt   20700
```

```
ccccatggcc cacaacaccg cctccacgct tgaggccatg cttagaaacg acaccaacga   20760
ccagtccttt aacgactatc tctccgccgc caacatgctc taccctatac ccgccaacgc   20820
taccaacgtg cccatatcca tcccctcccg caactgggcg gctttccgcg gctgggcctt   20880
cacgcgcctt aagactaagg aaaccccatc actgggctcg ggctacgacc cttattacac   20940
ctactctggc tctataccct acctagatgg aaccttttac ctcaaccaca cctttaagaa   21000
ggtggccatt acctttgact cttctgtcag ctggcctggc aatgaccgcc tgcttacccc   21060
caacgagttt gaaattaagc gctcagttga cggggagggt tacaacgttg cccagtgtaa   21120
catgaccaaa gactggttcc tggtacaaat gctagctaac tacaacattg gctaccaggg   21180
cttctatatc ccagagagct acaaggaccg catgtactcc ttctttagaa acttccagcc   21240
catgagccgt caggtggtgg atgatactaa atacaaggac taccaacagg tgggcatcct   21300
acaccaacac aacaactctg gatttgttgg ctaccttgcc cccaccatgc gcgaaggaca   21360
ggcctaccct gctaacttcc cctatccgct tataggcaag accgcagttg acagcattac   21420
ccagaaaaag tttctttgcg atcgcaccct ttggcgcatc ccattctcca gtaactttat   21480
gtccatgggc gcactcacag acctgggcca aaaccttctc tacgccaact ccgcccacgc   21540
gctagacatg acttttgagg tggatcccat ggacgagccc acccttcttt atgttttgtt   21600
tgaagtcttt gacgtggtcc gtgtgcaccg gccgcaccgc ggcgtcatcg aaaccgtgta   21660
cctgcgcacg cccttctcgg ccggcaacgc cacaacataa agaagcaagc aacatcaaca   21720
acagctgccg ccatgggctc cagtgagcag gaactgaaag ccattgtcaa agatcttggt   21780
tgtgggccat atttttttggg cacctatgac aagcgctttc caggctttgt ttctccacac   21840
aagctcgcct gcgccatagt caatacggcc ggtcgcgaga ctgggggcgt acactggatg   21900
gcctttgcct ggaacccgca ctcaaaaaca tgctacctct ttgagcgctt tggcttttct   21960
gaccagcgac tcaagcaggt ttaccagttt gagtacgagt cactcctgcg ccgtagcgcc   22020
attgcttctt cccccgaccg ctgtataacg ctggaaaagt ccacccaaag cgtacagggg   22080
cccaactcgg ccgcctgtgg actattctgc tgcatgtttc tccacgcctt tgccaactgg   22140
ccccaaactc ccatggatca aaccccccacc atgaaccttta ttaccggggt acccaactcc   22200
atgctcaaca gtccccaggt acagcccacc ctgcgtcgca accaggaaca gctctacagc   22260
ttcctggagc gccactcgcc ctacttccgc agccacagtg cgcagattag gagcgccact   22320 tcttttttgtc acttgaaaaa catgtaaaaa taatgtacta gagacacttt caataaaggc   22380 aaaatgctttt atttgtacac tctcgggtga ttatttaccc ccacccttgc cgtctgcgcc   22440
gtttaaaaat caaaggggtt ctgccgcgca tcgctatgcg ccactggcag ggacacgttg   22500
cgatactggt gtttagtgct ccacttaaac tcaggcacaa ccatccgcgg cagctcggtg   22560
aagttttcac tccacaggct gcgcaccatc accaacgcgt ttagcaggtc gggcgccgat   22620
atcttgaagt cgcagttggg gcctccgccc tgcgcgcgcg agttgcgata cagggttg   22680 cagcactgga acactatcag cgccgggtgg tgcacgctgg ccagcacgct cttgtcggag   22740
atcagatccg cgtccaggtc ctccgcgttg ctcagggcga acggagtcaa ctttggtagc   22800
tgccttccca aaagggcgc gtgcccaggc tttgagttgc actcgcaccg tagtggcatc   22860
aaaaggtgac cgtgcccggt ctgggcgtta ggatacagcg cctgcataaa agccttgatc   22920
tgcttaaaag ccacctgagc cttttgcgcct tcagagaaga acatgccgca agacttgccg   22980
gaaaactgat tggccggaca ggccgcgtcg tgcacgcagc accttgcgtc ggtgttggag   23040
```

```
atctgcacca catttcggcc ccaccggttc ttcacgatct tggccttgct agactgctcc    23100
ttcagcgcgc gctgcccgtt ttcgctcgtc acatccattt caatcacgtg ctccttattt    23160
atcataatgc ttccgtgtag acacttaagc tcgccttcga tctcagcgca gcggtgcagc    23220
cacaacgcgc agcccgtggg ctcgtgatgc ttgtaggtca cctctgcaaa cgactgcagg    23280
tacgcctgca ggaatcgccc catcatcgtc acaaaggtct tgttgctggt gaaggtcagc    23340
tgcaacccgc ggtgctcctc gttcagccag gtcttgcata cggccgccag agcttccact    23400
tggtcaggca gtagtttgaa gttcgccttt agatcgttat ccacgtggta cttgtccatc    23460
agcgcgcgcg cagcctccat gcccttctcc cacgcagaca cgatcggcac actcagcggg    23520
ttcatcaccg taatttcact ttccgcttcg ctgggctctt cctcttcctc ttgcgtccgc    23580
ataccacgcg ccactgggtc gtcttcattc agccgccgca ctgtgcgctt acctcctttg    23640
ccatgcttga ttagcaccgg tgggttgctg aaacccacca tttgtagcgc cacatcttct    23700
ctttcttcct cgctgtccac gattacctct ggtgatggcg ggcgctcggg cttgggagaa    23760
gggcgcttct ttttcttctt gggcgcaatg gccaaatccg ccgccgaggt cgatggccgc    23820
gggctgggtg tgcgcggcac cagcgcgtct tgtgatgagt cttcctcgtc ctcggactcg    23880
atacgccgcc tcatccgctt ttttggggcc gcccggggag gcggcggcga cggggacggg    23940
gacgacacgt cctccatggt tggggacgt cgcgccgcac cgcgtccgcg ctcggggtg     24000 gtttcgcgct gctcctcttc ccgactggcc atttccttct cctataggca gaaaagatc    24060 atggagtcag tcgagaagaa ggacagccta accgcccct ctgagttcgc caccaccgcc    24120
tccaccgatg ccgccaacgc gcctaccacc ttccccgtcg aggcacccc gcttgaggag    24180 gaggaagtga ttatcgagca ggacccaggt tttgtaagcg aagacgacga ggaccgctca    24240
gtaccaacag aggataaaaa gcaagaccag gacaacgcag aggcaaacga ggaacaagtc    24300 gggcggggg acgaaaggca tggcgactac ctagatgtgg gagacgacgt gctgttgaag    24360
catctgcagc gccagtgcgc cattatctgc gacgcgttgc aagagcgcag cgatgtgccc    24420
ctcgccatag cggatgtcag ccttgcctac gaacgccacc tattctcacc gcgcgtaccc    24480
cccaaacgcc aagaaaacgg cacatgcgag cccaacccgc gcctcaactt ctaccccgta    24540
tttgccgtgc cagaggtgct tgccacctat cacatctttt tccaaaactg caagataccc    24600
ctatcctgcc gtgccaaccg cagccgagcg gacaagcagc tggccttgcg gcagggcgct    24660
gtcataccgt atatcgcctc gctcaacgaa gtgccaaaaa tctttgaggg tcttggacgc    24720
gacgagaagc gcgcggcaaa cgctctgcaa caggaaaaca gcgaaaatga aagtcactct    24780
ggagtgttgg tggaactcga gggtgacaac gcgcgcctag ccgtactaaa acgcagcatc    24840
gaggtcaccc acttttgccta cccggcactt aacctacccc ccaaggtcat gagcacagtc    24900
atgagtgagc tgatcgtgcg ccgtgcgcag cccctggaga gggatgcaaa tttgcaagaa    24960
caaacagagg agggcctacc cgcagttggc gacgagcagc tagcgcgctg gcttcaaacg    25020
cgcgagcctg ccgacttgga ggagcgacgc aaactaatga tggccgcagt gctcgttacc    25080
gtggagcttg agtgcatgca gcggttcttt gctgacccgg agatgcagcg caagctagag    25140
gaaacattgc actacacctt tcgacagggc tacgtacgcc aggcctgcaa gatctccaac    25200
gtggagctct gcaacctggt ctcctacctt ggaattttgc acgaaaaccg ccttgggcaa    25260
aacgtgcttc attccacgct caagggcgag gcgcgccgcg actacgtccg cgactgcgtt    25320
tacttatttc tatgctacac ctggcagacg gccatgggcg tttggcagca gtgcttggag    25380
gagtgcaacc tcaaggagct gcagaaactg ctaaagcaaa acttgaagga cctatggacg    25440
```

```
gccttcaacg agcgctccgt ggccgcgcac ctggcggaca tcattttccc cgaacgcctg   25500
cttaaaaccc tgcaacaggg tctgccagac ttcaccagtc aaagcatgtt gcagaacttt   25560
aggaacttta tcctagagcg ctcaggaatc ttgcccgcca cctgctgtgc acttcctagc   25620
gactttgtgc ccattaagta ccgcgaatgc cctccgccgc tttggggcca ctgctacctt   25680
ctgcagctag ccaactacct tgcctaccac tctgacataa tggaagacgt gagcggtgac   25740
ggtctactgg agtgtcactg tcgctgcaac ctatgcaccc cgcaccgctc cctggtttgc   25800
aattcgcagc tgcttaacga aagtcaaatt atcggtacct ttgagctgca gggtccctcg   25860
cctgacgaaa agtccgcggc tccggggttg aaactcactc cggggctgtg gacgtcggct   25920
taccttcgca aatttgtacc tgaggactac cacgcccacg agattaggtt ctacgaagac   25980
caatcccgcc cgccaaatgc ggagcttacc gcctgcgtca ttacccaggg ccacattctt   26040
ggccaattgc aagccatcaa caaagcccgc caagagtttc tgctacgaaa gggacggggg   26100
gtttacttgg accccagtc cggcgaggag ctcaacccaa tcccccgcc gccgcagccc   26160 tatcagcagc agccgcgggc ccttgcttcc caggatggca cccaaaaaga agctgcagct   26220
gccgccgcca cccacggacg aggaggaata ctgggacagt caggcagagg aggttttgga   26280
cgaggaggag gaggacatga tggaagactg ggagagccta gacgaggaag cttccgaggt   26340
cgaagaggtg tcagacgaaa caccgtcacc ctcggtcgca ttcccctcgc cggcgcccca   26400
gaaatcggca accggttcca gcatggctac aacctccgct cctcaggcgc cgccggcact   26460
gcccgttcgc cgacccaacc gtagatggga caccactgga accagggccg gtaagtccaa   26520
gcagccgccg ccgttagccc aagagcaaca acagcgccaa ggctaccgct catggcgcgg   26580
gcacaagaac gccatagttg cttgcttgca agactgtggg ggcaacatct ccttcgcccg   26640 ccgcttctt ctctaccatc acggcgtggc cttcccccgt aacatcctgc attactaccg   26700
tcatctctac agcccatact gcaccggcgg cagcggcagc ggcagcaaca gcagcggcca   26760
cacagaagca aaggcgaccg gatagcaaga ctctgacaaa gcccaagaaa tccacagcgg   26820
cggcagcagc aggaggagga gcgctgcgtc tggcgcccaa cgaacccgta tcgacccgcg   26880
agcttagaaa caggattttt cccactctgt atgctatatt tcaacagagc aggggccaag   26940
aacaagagct gaaaataaaa aacaggtctc tgcgatccct cacccgcagc tgcctgtatc   27000 acaaagcga agatcagctt cggcgcacgc tggaagacgc ggaggctctc ttcagtaaat   27060
actgcgcgct gactcttaag gactagtttc gcgccctttc tcaaatttaa gcgcgaaaac   27120
tacgtcatct ccagcggcca cacccggcgc cagcacctgt cgtcagcgcc attatgagca   27180
aggaaattcc cacgccctac atgtggagtt accagccaca aatgggactt gcggctggag   27240
ctgcccaaga ctactcaacc cgaataaact acatgagcgc gggaccccac atgatatccc   27300
gggtcaacgg aatccgcgcc caccgaaacc gaattctctt ggaacaggcg gctattacca   27360
ccacacctcg taataacctt aatccccgta gttggcccgc tgccctggtg taccaggaaa   27420
gtcccgctcc caccactgtg gtacttccca gagacgccca ggccgaagtt cagatgacta   27480
actcaggggc gcagcttgcg ggcggctttc gtcacagggt gcggtcgccc ggcagggta   27540 taactcacct gacaatcaga gggcgaggta ttcagctcaa cgacgagtcg gtgagctcct   27600
cgcttggtct ccgtccggac gggacatttc agatcggcgg cgccggccgt ccttcattca   27660
cgcctcgtca gcaatcctta actctgcaga cctcgtcctc tgagccgcgc tctgaggca   27720 ttggaactct gcaattttat gaggagtttg tgccatcggt ctactttaac cccttctcgg   27780
```

```
gacctcccgg ccactatccg gatcaattta ttcctaactt tgacgcggta aaggactcgg    27840
cggacggcta cgactgaatg ttaagtggag aggcagagca actgcgcctg aaacacctgg    27900
tccactgtcg ccgccacaag tgctttgccc gcgactccgg tgagttttgc tactttgaat    27960
tgcccgagga tcatatcgag ggcccggcgc acggcgtccg gcttaccgcc cagggagagc    28020
ttgcccgtag cctgattcgg gagtttaccc agcgccccct gctagttgag cgggacaggg    28080
gaccctgtgt tctcactgtg atttgcaact gtcctaacct tggattacat caagatcttt    28140
gttgccatct ctgtgctgag tataataaat acagaaatta aaatatactg gggctcctat    28200
cgccatcctg taaacgccac cgtcttcacc cgcccaagca aaccaaggcg aaccttacct    28260 ggtacttta acatctctcc ctctgtgatt tacaacagtt tcaacccaga cggagtgagt    28320
ctacgagaga acctctccga gctcagctac tccatcagaa aaacaccac cctccttacc    28380 tgccgggaac gtacgagtgc gtcaccggcc gctgcaccac acctaccgcc tgaccgtaaa    28440
ccagactttt tccggacaga cctcaataac tctgtttacc agaacaggag gtgagcttag    28500 aaaacccta gggtattagg ccaaaggcgc agctactgtg gggtttatga acaattcaag    28560
caactctacg ggctattcta attcaggttt ctctagaatc ggggttgggg ttattctctg    28620
tcttgtgatt ctctttattc ttatactaac gcttctctgc ctaaggctcg ccgcctgctg    28680
tgtgcacatt tgcatttatt gtcagctttt taaacgctgg ggtcgccacc caagatgatt    28740
aggtacataa tcctaggttt actcaccctt gcgtcagccc acggtaccac ccaaaaggtg    28800
gattttaagg agccagcctg taatgttaca ttcgcagctg aagctaatga gtgcaccact    28860 cttataaat gcaccacaga acatgaaaag ctgcttattc gccacaaaaa caaaattggc    28920
aagtatgctg tttatgctat ttggcagcca ggtgacacta cagagtataa tgttacagtt    28980
ttccagggta aaagtcataa aacttttatg tatactttc catttatga aatgtgcgac    29040 attaccatgt acatgagcaa acagtataag ttgtggcccc cacaaaattg tgtggaaaac    29100
actggcactt tctgctgcac tgctatgcta attacagtgc tcgctttggt ctgtaccta    29160 ctctatatta aatacaaaag cagacgcagc tttattgagg aaaagaaaat gccttaattt    29220
actaagttac aaagctaatg tcaccactaa ctgctttact cgctgcttgc aaaacaaatt    29280
caaaaagtta gcattataat tagaatagga tttaacccc ccggtcattt cctgctcaat    29340
accattcccc tgaacaattg actctatgtg ggatatgctc cagcgctaca accttgaagt    29400
caggcttcct ggatgtcagc atctgacttt ggccagcacc tgtcccgcgg atttgttcca    29460
gtccaactac agcgacccac cctaacgaga tgaccaaca caaccaacgc ggccgccgct    29520
accggactta catctaccac aaatacacc caagtttctg cctttgtcaa taactgggat    29580
aacttgggca tgtggtggtt ctccatagcg cttatgtttg tatgccttat tattatgtgg    29640
ctcatctgct gcctaaagcg caaacgcgcc cgaccaccca tctatagtcc catcattgtg    29700
ctacacccaa acaatgatgg aatccataga ttggacggac tgaaacacat gttcttttct    29760
cttacagtat gattaaatga gacatgattc ctcgagtttt tatattactg acccttgttg    29820 cgctttttg tgcgtgctcc acattggctg cggtttctca catcgaagta gactgcattc    29880
cagccttcac agtctatttg ctttacggat ttgtcaccct cacgctcatc tgcagcctca    29940
tcactgtggt catcgccttt atccagtgca ttgactgggt ctgtgtgcgc tttgcatatc    30000
tcagacacca tccccagtac agggacagga ctatagctga gcttcttaga attctttaat    30060
tatgaaattt actgtgactt ttctgctgat tatttgcacc ctatctgcgt tttgttcccc    30120
gacctccaag cctcaaagac atatatcatg cagattcact cgtatatgga atattccaag    30180
```

```
ttgctacaat gaaaaaagcg atctttccga agcctggtta tatgcaatca tctctgttat    30240
ggtgttctgc agtaccatct tagccctagc tatatatccc taccttgaca ttggctggaa    30300
acgaatagat gccatgaacc acccaacttt ccccgcgccc gctatgcttc cactgcaaca    30360
agttgttgcc ggcggctttg tcccagccaa tcagcctcgc cccacttctc caccccccac    30420
tgaaatcagc tactttaatc taacaggagg agatgactga caccctagat ctagaaatgg    30480
acggaattat tacagagcag cgcctgctag aaagacgcag ggcagcggcc gagcaacagc    30540
gcatgaatca agagctccaa gacatggtta acttgcacca gtgcaaaagg ggtatctttt    30600
gtctggtaaa gcaggccaaa gtcacctacg acagtaatac caccggacac cgccttagct    30660
acaagttgcc aaccaagcgt cagaaattgg tggtcatggt gggagaaaag cccattacca    30720
taactcagca ctcggtagaa accgaaggct gcattcactc accttgtcaa ggacctgagg    30780
atctctgcac ccttattaag accctgtgcg gtctcaaaga tcttattccc tttaactaat    30840
aaaaaaaaat aataaagcat cacttactta aaatcagtta gcaaatttct gtccagttta    30900
ttcagcagca cctccttgcc ctcctcccag ctctggtatt gcagcttcct cctggctgca    30960
aactttctcc acaatctaaa tggaatgtca gtttcctcct gttcctgtcc atccgcaccc    31020
actatcttca tgttgttgca gatgaagcgc gcaagaccgt ctgaagatac cttcaacccc    31080
gtgtatccat atgacacgga aaccggtcct ccaactgtgc cttttcttac tcctcccttt    31140
gtatcccccca atgggtttca agagagtccc cctggggtac tctctttgcg cctatccgaa    31200
cctctagtta cctccaatgg catgcttgcg ctcaaaatgg gcaacggcct ctctctggac    31260
gaggccggca accttacctc ccaaaatgta accactgtga gcccacctct caaaaaaacc    31320
aagtcaaaca taaacctgga aatatctgca cccctcacag ttacctcaga gccctaact    31380
gtggctgccg ccgcacctct aatggtcgcg ggcaacacac tcaccatgca atcacaggcc    31440
ccgctaaccg tgcacgactc caaacttagc attgccaccc aaggacccct cacagtgtca    31500
gaaggaaagc tagccctgca acatcaggc ccccctcacca ccaccgatag cagtacccctt    31560
actatcactg cctcaccccc tctaactact gccactggta gcttgggcat tgacttgaaa    31620
gagcccattt atacacaaaa tggaaaacta ggactaaagt acggggctcc tttgcatgta    31680
acagacgacc taaacacttt gaccgtagca actggtccag gtgtgactat taataatact    31740
tccttgcaaa ctaaagttac tggagccttg ggttttgatt cacaaggcaa tatgcaactt    31800
aatgtagcag gaggactaag gattgattct caaaacagac gccttatact tgatgttagt    31860
tatccgtttg atgctcaaaa ccaactaaat ctaagactag gacagggccc tctttttata    31920
aactcagccc acaacttgga tattaactac aacaaaggcc tttacttgtt tacagcttca    31980
aacaattcca aaagcttga ggttaaccta agcactgcca aggggttgat gtttgacgct    32040
acagccatag ccattaatgc aggagatggg cttgaatttg gttcacctaa tgcaccaaac    32100
acaaatcccc tcaaaacaaa aattggccat ggcctagaat tgattcaaa caaggctatg    32160
gttcctaaac taggaactgg ccttagtttt gacagcacag gtgccattac agtaggaaac    32220
aaaaataatg ataagctaac tttgtggacc acaccagctc catctcctaa ctgtagacta    32280
aatgcagaga aagatgctaa actcactttg gtcttaacaa aatgtggcag tcaaatactt    32340
gctacagttt cagttttggc tgttaaaggc agtttggctc caatatctgg aacagttcaa    32400
agtgctcatc ttattataag atttgacgaa aatggagtgc tactaaacaa ttccttcctg    32460
gacccagaat attggaactt tagaaatgga gatcttactg aaggcacagc ctatacaaac    32520
```

```
gctgttggat ttatgcctaa cctatcagct tatccaaaat ctcacggtaa aactgccaaa    32580
agtaacattg tcagtcaagt ttacttaaac ggagacaaaa ctaaacctgt aacactaacc    32640
attacactaa acggtacaca ggaaacagga gacacaactc caagtgcata ctctatgtca    32700
ttttcatggg actggtctgg ccacaactac attaatgaaa tatttgccac atcctcttac    32760 acttttcat acattgccca agaataaaga atcgtttgtg ttatgtttca acgtgtttat    32820
ttttcaattg cagaaaattt caagtcattt ttcattcagt agtatagccc caccaccaca    32880
tagcttatac agatcaccgt accttaatca aactcacaga accctagtat tcaacctgcc    32940
acctccctcc caacacacag agtacacagt cctttctccc cggctggcct taaaaagcat    33000
catatcatgg gtaacagaca tattcttagg tgttatattc cacacggttt cctgtcgagc    33060
caaacgctca tcagtgatat taataaactc cccgggcagc tcacttaagt tcatgtcgct    33120
gtccagctgc tgagccacag gctgctgtcc aacttgcggt tgcttaacgg gcggcgaagg    33180
agaagtccac gcctacatgg gggtagagtc ataatcgtgc atcaggatag ggcggtggtg    33240
ctgcagcagc gcgcgaataa actgctgccg ccgccgctcc gtcctgcagg aatacaacat    33300
ggcagtggtc tcctcagcga tgattcgcac cgcccgcagc ataaggcgcc ttgtcctccg    33360
ggcacagcag cgcaccctga tctcacttaa atcagcacag taactgcagc acagcaccac    33420
aatattgttc aaaatcccac agtgcaaggc gctgtatcca aagctcatgg cggggaccac    33480
agaacccacg tggccatcat accacaagcg caggtagatt aagtggcgac ccctcataaa    33540
cacgctggac ataaacatta cctcttttgg catgttgtaa ttcaccacct cccggtacca    33600
tataaacctc tgattaaaca tggcgccatc caccaccatc ctaaaccagc tggccaaaac    33660
ctgcccgccg gctatacact gcagggaacc gggactggaa caatgacagt ggagagccca    33720
ggactcgtaa ccatggatca tcatgctcgt catgatatca atgttggcac aacacaggca    33780
cacgtgcata cacttcctca ggattacaag ctcctcccgc gttagaacca tatcccaggg    33840
aacaacccat tcctgaatca gcgtaaatcc cacactgcag ggaagacctc gcacgtaact    33900
cacgttgtgc attgtcaaag tgttacattc gggcagcagc ggatgatcct ccagtatggt    33960
agcgcgggtt tctgtctcaa aaggaggtag acgatcccta ctgtacggag tgcgccgaga    34020
caaccgagat cgtgttggtc gtagtgtcat gccaaatgga acgccggacg tagtcatatt    34080
tcctgaagca aaaccaggtg cgggcgtgac aaacagatct gcgtctccgg tctcgccgct    34140
tagatcgctc tgtgtagtag ttgtagtata tccactctct caaagcatcc aggcgccccc    34200
tggcttcggg ttctatgtaa actccttcat gcgccgctgc cctgataaca tccaccaccg    34260
cagaataagc cacacccagc caacctacac attcgttctg cgagtcacac acgggaggag    34320
cgggaagagc tggaagaacc atgtttttt tttattcca aaagattatc caaaaccctca    34380 aaatgaagat ctattaagtg aacgcgctcc cctccggtgg cgtggtcaaa ctctacagcc    34440
aaagaacaga taatggcatt tgtaagatgt tgcacaatgg cttccaaaag gcaaacggcc    34500
ctcacgtcca agtggacgta aaggctaaac ccttcagggt gaatctcctc tataaacatt    34560
ccagcacctt caaccatgcc caaataattc tcatctcgcc accttctcaa tatatctcta    34620
agcaaatccc gaatattaag tccggccatt gtaaaaatct gctccagagc gccctccacc    34680
ttcagcctca agcagcgaat catgattgca aaaattcagg ttcctcacag acctgtataa    34740
gattcaaaag cggaacatta acaaaaatac cgcgatcccg taggtcccett cgcagggcca    34800 gctgaacata atcgtgcagg tctgcacgga ccagcgcggc cacttccccg ccaggaacca    34860
tgacaaaaga acccacactg attatgacac gcatactcgg agctatgcta accagcgtag    34920
```

```
cccgatgta  agcttgttgc  atgggcggcg  atataaaatg  caaggtgctg  ctcaaaaaat   34980
caggcaaagc  ctcgcgcaaa  aagaaagca   catcgtagtc  atgctcatgc  agataaaggc   35040
aggtaagctc  cggaaccacc  acagaaaaag  acaccatttt  tctctcaaac  atgtctgcgg   35100
gtttctgcat  aaacacaaaa  taaataaca   aaaaaacatt  taaacattag  aagcctgtct   35160
tacaacagga  aaacaaccc   ttataagcat  aagacggact  acggccatgc  cggcgtgacc   35220
gtaaaaaaac  tggtcaccgt  gattaaaaag  caccaccgac  agctcctcgg  tcatgtccgg   35280
agtcataatg  taagactcgg  taaacacatc  aggttgattc  acatcggtca  gtgctaaaaa   35340
gcgaccgaaa  tagcccgggg  gaatacatac  ccgcaggcgt  agagacaaca  ttacagcccc   35400
cataggaggt  ataacaaaat  taataggaga  gaaaaacaca  taaacacctg  aaaaaccctc   35460
ctgcctaggc  aaaatagcac  cctcccgctc  cagaacaaca  tacagcgctt  ccacagcggc   35520
agccataaca  gtcagcctta  ccagtaaaaa  agaaaaccta  ttaaaaaaac  accactcgac   35580
acggcaccag  ctcaatcagt  cacagtgtaa  aaaagggcca  agtgcagagc  gagtatatat   35640
aggactaaaa  aatgacgtaa  cggttaaagt  ccacaaaaaa  cacccagaaa  accgcacgcg   35700
aacctacgcc  cagaaacgaa  agccaaaaaa  cccacaactt  cctcaaatcg  tcacttccgt   35760
tttcccacgt  tacgtaactt  cccattttaa  gaaaactaca  attcccaaca  catacaagtt   35820
actccgccct  aaaacctacg  tcacccgccc  cgttcccacg  ccccgcgcca  cgtcacaaac   35880
tccaccccct  cattatcata  ttggcttcaa  tccaaaataa  ggtatattat  tgatgatg     35938
```

<210> SEQ ID NO 42
<211> LENGTH: 160
<212> TYPE: PRT
<213> ORGANISM: Adenovirus

<400> SEQUENCE: 42

Met Glu Arg Arg Asn Pro Ser Glu Arg Gly Val Pro Ala Gly Phe Ser
1               5                   10                  15

Gly His Ala Phe Val Glu Ser Gly Gly Glu Thr Gln Glu Ser Pro Thr
            20                  25                  30

Thr Val Val Phe Arg Pro Gly Asn Asn Thr Asp Gly Gly Ala Ala
        35                  40                  45

Ala Ala Thr Ala Ala Ala Gly Gly Ser Gln Ala Ala Ala Ala Gly
    50                  55                  60

Ala Glu Pro Met Glu Pro Glu Ser Arg Pro Gly Pro Ser Gly Met Asn
65                  70                  75                  80

Val Val Gln Pro Glu Ser Met Ser Lys Val Asn Leu Asn Gly Val Phe
                85                  90                  95

Asp Met Thr Met Lys Ile Trp Lys Val Leu Arg Tyr Asp Glu Thr Arg
            100                 105                 110

Thr Arg Cys Arg Pro Cys Glu Cys Gly Gly Lys His Ile Arg Asn Gln
        115                 120                 125

Pro Val Met Leu Asp Val Thr Glu Glu Leu Arg Pro Asp His Leu Val
    130                 135                 140

Leu Ala Cys Thr Arg Ala Glu Phe Gly Ser Ser Asp Glu Asp Thr Asp
145                 150                 155                 160

<210> SEQ ID NO 43
<211> LENGTH: 155
<212> TYPE: PRT
<213> ORGANISM: Adenovirus

<400> SEQUENCE: 43

| | | | | | | | | | | | | | | |
|---|---|---|---|---|---|---|---|---|---|---|---|---|---|---|
| Met | Glu | Arg | Arg | Asn | Pro | Ser | Glu | Arg | Gly | Val | Pro | Ala | Gly | Phe | Ser |
| 1 | | | | 5 | | | | | 10 | | | | | 15 | |
| Gly | His | Ala | Ser | Val | Glu | Ser | Gly | Gly | Glu | Thr | Gln | Glu | Ser | Pro | Ala |
| | | | 20 | | | | | 25 | | | | | 30 | | |
| Thr | Val | Val | Phe | Arg | Pro | Pro | Gly | Asn | Asn | Thr | Asp | Gly | Gly | Ala | Thr |
| | | | 35 | | | | | 40 | | | | | 45 | | |
| Ala | Gly | Gly | Ser | Gln | Ala | Ala | Ala | Ala | Gly | Ala | Glu | Pro | Met | Glu | |
| | 50 | | | | | 55 | | | | | 60 | | | | |
| Pro | Glu | Ser | Arg | Pro | Gly | Pro | Ser | Gly | Met | Asn | Val | Val | Gln | Pro | Glu |
| 65 | | | | | 70 | | | | | 75 | | | | | 80 |
| Ser | Met | Ser | Lys | Val | Asn | Leu | Asn | Gly | Val | Phe | Asp | Met | Thr | Met | Lys |
| | | | | 85 | | | | | 90 | | | | | 95 | |
| Ile | Trp | Lys | Val | Leu | Arg | Tyr | Asp | Glu | Thr | Arg | Thr | Arg | Cys | Arg | Pro |
| | | | | 100 | | | | | 105 | | | | | 110 | |
| Cys | Glu | Cys | Gly | Gly | Lys | His | Ile | Arg | Asn | Gln | Pro | Val | Met | Leu | Asp |
| | | | | 115 | | | | | 120 | | | | | 125 | |
| Val | Thr | Glu | Glu | Leu | Arg | Pro | Asp | His | Leu | Val | Leu | Ala | Cys | Thr | Arg |
| | 130 | | | | | 135 | | | | | 140 | | | | |
| Ala | Glu | Phe | Gly | Ser | Ser | Asp | Glu | Asp | Thr | Asp | | | | | |
| 145 | | | | | 150 | | | | | 155 | | | | | |

<210> SEQ ID NO 44
<211> LENGTH: 155
<212> TYPE: PRT
<213> ORGANISM: Adenovirus

<400> SEQUENCE: 44

| | | | | | | | | | | | | | | |
|---|---|---|---|---|---|---|---|---|---|---|---|---|---|---|
| Met | Glu | Arg | Arg | Asn | Pro | Ser | Glu | Arg | Gly | Val | Pro | Ala | Gly | Phe | Ser |
| 1 | | | | 5 | | | | | 10 | | | | | 15 | |
| Gly | His | Ala | Ser | Val | Glu | Ser | Gly | Gly | Glu | Thr | Gln | Glu | Ser | Pro | Ala |
| | | | 20 | | | | | 25 | | | | | 30 | | |
| Thr | Val | Val | Phe | Arg | Pro | Pro | Gly | Asn | Asn | Thr | Asp | Gly | Gly | Ala | Thr |
| | | | 35 | | | | | 40 | | | | | 45 | | |
| Ala | Gly | Gly | Ser | Gln | Ala | Ala | Ala | Ala | Gly | Ala | Glu | Pro | Met | Glu | |
| | 50 | | | | | 55 | | | | | 60 | | | | |
| Pro | Glu | Ser | Arg | Pro | Gly | Pro | Ser | Gly | Met | Asn | Val | Val | Gln | Pro | Glu |
| 65 | | | | | 70 | | | | | 75 | | | | | 80 |
| Ser | Met | Ser | Lys | Val | Asn | Leu | Asn | Gly | Val | Phe | Asp | Met | Thr | Met | Lys |
| | | | | 85 | | | | | 90 | | | | | 95 | |
| Ile | Trp | Lys | Val | Leu | Arg | Tyr | Asp | Glu | Thr | Arg | Thr | Arg | Cys | Arg | Pro |
| | | | | 100 | | | | | 105 | | | | | 110 | |
| Cys | Glu | Cys | Gly | Gly | Lys | His | Ile | Arg | Asn | Gln | Pro | Val | Met | Leu | Asp |
| | | | | 115 | | | | | 120 | | | | | 125 | |
| Val | Thr | Glu | Glu | Leu | Arg | Pro | Asp | His | Leu | Val | Leu | Ala | Cys | Thr | Arg |
| | 130 | | | | | 135 | | | | | 140 | | | | |
| Ala | Glu | Phe | Gly | Ser | Ser | Asp | Glu | Asp | Thr | Asp | | | | | |
| 145 | | | | | 150 | | | | | 155 | | | | | |

<210> SEQ ID NO 45
<211> LENGTH: 127
<212> TYPE: PRT
<213> ORGANISM: Adenovirus

<400> SEQUENCE: 45

Met Glu Ser Arg Asn Pro Phe Gln Gln Gly Leu Pro Ala Gly Phe Leu

```
1               5                   10                  15
Ser Ser Ser Phe Val Glu Asn Met Glu Val Pro Ala Pro Glu Cys Asn
                20                  25                  30

Leu Arg Leu Leu Ala Gly Thr Ala Ala Arg His Ser Glu Asp Pro Glu
            35                  40                  45

Ser Pro Ala Ala Gly Gly Ser Arg Arg Glu Ser Glu Ser Arg Pro Gly
        50                  55                  60

Pro Ser Gly Gly Gly Val Ala Asp Leu Phe Pro Glu Leu His Arg Thr
65                      70                  75                  80

Arg Cys Arg Ala Cys Glu Cys Gly Gly Lys His Ala Arg Phe Gln Pro
                85                  90                  95

Val Cys Val Asp Val Thr Glu Asp Leu Arg Pro Asp His Leu Val Leu
                100                 105                 110

Ser Cys Thr Gly Thr Glu Phe Gly Ser Ser Gly Glu Glu Ser Asp
                115                 120                 125

<210> SEQ ID NO 46
<211> LENGTH: 144
<212> TYPE: PRT
<213> ORGANISM: Adenovirus

<400> SEQUENCE: 46

Met Asp Pro Ala Asp Ser Phe Gln Gln Gly Ile Arg Phe Gly Phe His
1               5                   10                  15

Ser His Ser Ile Val Glu Asn Met Glu Gly Ser Gln Asp Glu Asp Asn
                20                  25                  30

Leu Arg Leu Leu Ala Ser Ala Ala Phe Gly Cys Ser Gly Asn Pro Glu
            35                  40                  45

Ala Ser Thr Gly His Ala Ser Gly Ser Gly Gly Thr Ala Arg Gly
        50                  55                  60

Gln Pro Glu Ser Arg Pro Gly Pro Ser Ser Gly Gly Gly Val Ala
65                      70                  75                  80

Asp Leu Ser Pro Glu Leu Gln Arg Ile Leu Arg Tyr Asp Asp Thr Arg
                85                  90                  95

Ser Arg Val Arg Ala Cys Glu Cys Gly Gly Lys His Ala Arg Phe Gln
                100                 105                 110

Pro Val Cys Val Asp Val Thr Glu Asp Leu Arg Pro Asp His Leu Val
                115                 120                 125

Ile Ala Arg Thr Gly Ala Glu Phe Gly Ser Ser Gly Glu Glu Thr Asp
            130                 135                 140
```

US 10,047,347 B2

ONCOLYTIC ADENOVIRUSES WITH INCREASED PROPORTION OF THE 156R SPLICING ISOFORM OF THE E1B PROTEIN

TECHNICAL FIELD

This invention relates to oncolytic adenoviruses and their use in treating neoplastic disease. More particularly, the invention relates to mutations of the E1B gene that modulate the levels of splicing isoforms of this gene, thereby improving the therapeutic index of the oncolytic adenovirus.

BACKGROUND TO THE INVENTION

Oncolytic Viruses

Oncolytic virotherapy is an emerging treatment platform for cancer therapy. Oncolytic viruses are viruses that selectively replicate in cancer cells that possess specific oncogenic phenotypes, thereby killing cancer cells whilst sparing normal cells. Initial research focussed on naturally-occurring non-pathogenic viruses, however, these studies were of limited success. Although tumour growth was observed to slow down and normal tissue was not damaged, there was no alteration in the course of the disease.

Recent studies have therefore focussed on engineering recombinant viruses that selectively target cancer cells. One example of this class of engineered viruses is adenoviruses that are mutated in the E1B region of the viral genome.

Adenoviral E1B and p53

One function of the mammalian tumour suppressor protein p53 is to mediate cell-cycle arrest and/or apoptosis in response to DNA damage or foreign DNA synthesis. Consequently, some viruses, such as adenovirus, encode proteins that inactivate p53 in infected cells to allow efficient viral replication. One of these proteins, the 55 kiloDalton protein from the E1B region of adenovirus (E1B-55K or E1B-496R), binds to p53 so causing a substantial loss of p53. This consequently prevents p53-mediated apoptosis of the infected cell. E1B-496R is therefore essential for adenoviral replication in cells containing functional p53.

Human tumour cells are frequently homozygous or heterozygous for mutated (e.g. substitution, deletion, frameshift mutated) p53 alleles, and lack p53 function necessary for normal control of the cell cycle (Hollstein et. al (1991) Science 253:49; Levine et al. (1991) Nature; 351(6326):453-6). Many neoplastic cells are therefore p53$^{(-)}$ either because they lack sufficient levels of p53 and/or because they express mutant forms of p53 which are incapable of substantial p53 function.

E1B Mutated Adenoviruses

Oncolytic adenoviruses have been engineered that take advantage of the difference in p53 functionality between neoplastic and normal cells. By mutating the E1B-496R protein to remove binding interactions with p53 or by making various deletions within the E1B locus (see, for example, U.S. Pat. No. 5,677,178), the resulting adenoviruses can replicate and ultimately lyse cancer cells that substantially lack p53 function, but not in cells that possess normal p53 function.

One example is ONYX-015 (originally named dl1520 and also referred to as H101), a mutant adenovirus that does not express the E1B-496R protein (Heise et al. (1997) Nat. Med. 3 (6): 639-645). The virus contains a stop codon immediately following the translation start codon and also has a large deletion of the E1B-496R coding sequence. As a result this virus lacks the ability to bind and inactivate p53, and thus can only replicate efficiently in cells defective in p53 function, such as neoplastic cells and tumours. Unfortunately, E1B-496R carries out other functions in addition to binding and inactivating p53 (Eager et al. (2001) Cancer Gene Ther. 18 (5): 305-317). Consequently, the ONYX-015 virus is defective in cytoplasmic accumulation of the viral late mRNAs, host cell shut-off and translation of late mRNAs. Thus, the mutation in ONYX-015 compromises the ability of the mutant virus to reproduce itself in tumour cells. An additional problem is that large deletions destabilise the viral genome.

Additional examples are ONYX-051 and ONYX-053, mutant adenoviruses that contain point mutations (R240A and H260A, respectively) in the E1B-496R protein that prevent its binding to p53. These mutations enable the virus to replicate selectively in cells that are deficient in p53 function, without compromising the ability of the virus to replicate in these cells (Shen et al. (2001) J. Virol. 75 (9): 4297-4307 and U.S. Pat. No. 7,785,887).

However, there remains a great need for improved mutant viruses whose oncolytic ability has been enhanced and which are useful in the therapy of cancer.

DISCLOSURE OF INVENTION

It has now been found by the present inventor that by modulating the level and type of splice isoforms of the E1B gene product, expressed from the E1B gene, the oncolytic activity of such viruses can be enhanced. Accordingly, a first aspect of the present invention provides a recombinant adenovirus in which the proportion of the E1B-156R isoform is increased relative to wild-type levels, wherein the adenovirus has an oncolytic effect in a cancer cell. The recombinant adenovirus may carry a mutation such that the proportion of the E1B-156R isoform is increased relative to wild-type levels, so that the adenovirus has an oncolytic effect in a cancer cell. The mutation may be in the sequence of the E1B gene of the adenovirus. A virus according to the invention is therefore replication-inhibited in non-neoplastic cells but is capable of expressing a replication phenotype in neoplastic cells, including neoplastic cells that substantially lack functional p53.

In the specific examples of adenoviruses described herein, over-expression of E1B-156R is thought to be an imbalance caused by a mutated 93R splice site in the E1B gene of the adenovirus. 156R is able to complement some of the 496R function, but not the ones essential to oncoselectivity. In contrast to prior art viruses of similar type, viruses according to the present invention include a functional E3B region for better in vivo efficacy. For example, Onyx-015 lacks E3B. Indeed, Onyx-015 virus and its selectivity is by far outperformed by viruses according to the invention, in all respects. Furthermore, the inventor has tested viruses prepared in accordance with the invention in normal cells and the results show that the viruses have an outstanding safety profile, especially in comparison to the known virus Onyx-015.

Herein, the term "replication-inhibited virus" or "replication-defective" refers to a virus that preferentially inhibits cell proliferation or induces apoptosis in a predetermined cell population that is transformed into a cancerous or neoplastic state. Such a virus is substantially unable to inhibit cell proliferation, induce apoptosis, or express a replication phenotype in cells comprising normal p53 function levels that are characteristic of non-replicating, non-transformed cells. Such transformed cells may substantially lack p53 function, which supports expression of a virus replication phenotype. However, selectivity of viruses according to the invention for neoplastic tissue might well be more general than just for p53 status; the transformed state as such might be the basis for selection. For example, it has been suggested that oncolytic selectivity observed with the ONYX-015 virus may be due to the capacity of some cancer cell lines to support late viral RNA export from the nucleus, a function which is lost in ONYX-015 in normal cells due to the E1B-496R deletion. A similar mechanism may operate in the recombinant adenoviruses of the present invention, which have reduced levels of E1B-496R protein. It is not as yet clear exactly how an increase in the levels of E1B-156R in the recombinant adenoviruses of the present invention results in oncolytic selectivity.

Typically, a replication-inhibited virus according to the invention exhibits a substantial decrease in plaquing efficiency on cells comprising normal p53 function (for a suitable assay, see Wang, Y., G. Hallden, et al. (2003). "E3 gene manipulations affect oncolytic adenovirus activity in immunocompetent tumor models." Nature biotechnology 21(11): 1328-1335). Another example of a suitable assay that may be used is a cytotoxicity assay to measure loss of viable cells, using for example a tetrazolium dye such as MTT, XTT, MTS or a WST (see Berridge et al., Biotechnology Annual Review, 11: 127-152 (2005).

As used herein, the term "replication phenotype" refers to one or more of the following phenotypic characteristics of cells infected with a virus such as a replication-inhibited adenovirus: (1) substantial expression of late gene products, such as capsid proteins (e.g., adenoviral penton base polypeptide) or RNA transcripts initiated from viral late gene promoter(s); (2) replication of viral genomes or formation of replicative intermediates; (3) assembly of viral capsids or packaged virion particles; (4) appearance of cytopathic effect (CPE) in the infected cell; (5) completion of a viral lytic cycle; and (6) other phenotypic alterations which are typically contingent upon abrogation of p53 function in non-neoplastic cells infected with a wild-type replication-competent DNA virus encoding functional oncoprotein(s). A replication phenotype according to the present invention comprises at least one of the phenotypic characteristics listed above, preferably more than one of the phenotypic characteristics, such as 2, 3, 4, 5, 6 or more characteristics.

Techniques for the measurement of these phenotypes will be known to those of skill in the art. For example, methods to assess appearance of CPE are described in the examples herein, and evaluated using 50% tissue culture infective dose ($TCID_{50}$) and number of plaque-forming units (pfu)/cell (cell count on the day of infection).

The term "neoplastic cells" refers to cells which exhibit relatively autonomous growth, so that they exhibit an aberrant growth phenotype characterised by a significant loss of control of cell proliferation. Neoplastic cells comprise cells which may be actively replicating or in a temporary non-replicative resting state (G1 or G0); similarly, neoplastic cells may comprise cells that have a well-differentiated phenotype, a poorly differentiated phenotype, or a mixture of both types of cells. Thus, not all neoplastic cells are necessarily replicating cells at a given time point. The set of cells defined herein as neoplastic cells consists of cells in benign neoplasms and cells in malignant (or frank) neoplasms. Frankly neoplastic cells are frequently referred to as cancerous, typically carcinoma if originating from cells of endodermal or ectodermal histological origin, or sarcoma if originating from cells types derived from mesoderm. The terms neoplastic cell and cancer cell are used interchangeably herein.

Herein, the term "p53 function" refers to the property of having an essentially normal level of a polypeptide encoded by the p53 gene (i.e. relative to non-neoplastic cells of the same histological type), wherein the p53 polypeptide is capable of binding to wild-type adenovirus E1B-496R polypeptide. For example, p53 function may be lost by production of an inactive (i.e. mutant) form of p53 or by substantial decrease or total loss of expression of p53 polypeptide. p53 function may also be substantially absent in neoplastic cells that comprise p53 alleles that encode wild-type polypeptide; for example, a genetic alteration outside of the p53 locus, such as mutations that result in aberrant subcellular processing or localisation of p53 (e.g. a mutation resulting in localisation of p53 predominantly in the cytoplasm rather than the nucleus) can result in loss of p53 function. Many neoplastic cells are therefore p53$^{(-)}$ either because they lack sufficient levels of p53 and/or because they express mutant forms of p53 which are incapable of substantial p53 function. In the context to the present invention, the key function of p53 is the ability to mediate cell-cycle arrest and/or mediate apoptosis in response to DNA damage or foreign DNA synthesis. Neoplastic cells lack functional p53, if the said reduction in p53 function prevents normal control of the cell cycle and apoptosis. This may consist a decrease of 2-fold, 5-fold, 10-fold, 20-fold, 50-fold, 100-fold or more of correctly processed, localised and expressed p53 that can bind to E1B-496R, compared to the corresponding non-neoplastic cells of the same type. These cells are therefore termed "p53$^{(-)}$".

It is believed that replication-deficient adenovirus species which lack the capacity to complex p53 but substantially retain other essential viral replicative functions will exhibit a replication phenotype in cells which are deficient in p53 function (e.g., cells which are homozygous for substantially deleted p53 alleles, or cells which comprise mutant p53 proteins which are essentially non-functional) but will not substantially exhibit a replicative phenotype in non-replicating, non-neoplastic cells. Such replication inhibited adenovirus species are referred to herein for convenience as E1B-p53$^{(-)}$ replication-deficient adenoviruses.

An "oncolytic virus" is a virus that preferentially infects and lyses cancer cells. Oncolytic effect is seen when comparing efficacy in cancer cells versus normal cells. A virus is considered oncolytic if the ratio of lysed cancer cells to non-cancerous cells is 2:1, 4:1, 10:1, 20:1, 50:1, 100:1 or more. Preferably, a virus is identified as oncolytic by assessing the oncolytic index (see below). Herein, the oncolytic effect comprises a) viral infection of cells; b) selective replication of the viral genome in (p53 function-deficient) cancer cells leading to preferential virus-mediated cell lysis in cancer cells (which may be p53 deficient), and the release of viral particles for further infection events. The oncolytic effect can be measured using various assays. In these assays a control virus should be used, often the wild type/naturally occurring version. As such any of the following examples of assays can be used: MTS (cytotoxicity), $TCID_{50}$ (replication competency), LDH assays (lactate dehydrogenase (LDH) is a stable enzyme, present in all cell types, and is rapidly released into the cell culture medium upon damage of the plasma membrane), FACS (cell sorting), western blot, and QPCR (late gene expression or genome copy number). Other examples will be clear to those of skill in the art.

An advantage of a virus according to the present invention is that such a virus has minimal genetic aberrations. Preferably, a virus according to the invention will be mutated in its genetic sequence, such as in the form of point mutations (including insertions, deletions, additions, and substitutions); point mutations are better for the health of the virus.

Larger changes put an evolutionary strain on the virus. Additionally, genomic size and integrity can be important.

A virus according to the present invention has a cancer selection index or oncolytic index (the two terms are interchangeable) that is much improved in comparison to existing oncolytic viruses that are available, such as the H101 virus. This refers to the replication capacity in normal cells in comparison to cancer cells, which may be expressed according to the following equation:

$$(OVc/OVn)/(WTc/WTn)=\text{Cancer selection index}$$

wherein OV=Oncolytic virus replication capacity; WT is Control virus replication capacity; c is cancer cells; n is normal cells.

A virus according to the invention may have a cancer selection index of between 2 and 10,000, depending on the type of cell, preferably between 5 and 5000, 10 and 1000, or 50 and 500. In the case of a representative example of a virus according to the invention, Ixovex, this virus exhibits a cancer selection index versus control of 3.5 in HeLa cells; 14 in A549 cells; 2000 in H1299 cells and 450 in H460 cells. In the same cell types, the values for the Onyx-015 virus versus Ixo-ctrl are HeLa=0.1x; A549=0.1x; H1299=0.05x; and H460=0.004x.

As such, it is possible to apply a virus according to the invention to the majority of tumour types. One theory is that the oncolytic viruses of the invention are selective for p53 negative status and quickly-replicating cells.

In addition, a virus according to the invention will be met by the host immune defence and ultimately cleared, this before the complete tumour eradication. This does not only present itself as a way of removing the virus, so negating any possible liver toxicity as a result of a viral overload, but also provides the chance to induce an anticancer immune response in the host since the immune system will be alerted to the viral presence in the tumour.

Adenoviruses

A virus according to the invention is a recombinant adenovirus. At the time of writing, there are more than 65 described serotypes in humans (HAdV-1 to 65) distributed across seven species (Human adenovirus A to G) and as many from other mammals and birds (see Strauss, "Adenovirus infections in humans," in *The Adenoviruses* (1984) ed. Ginsberg, pp. 451-596 Plenum Press, New York. For a general description of adenovirus biology see *Virology*, Second Edition, eds. Fields and Knipe. Vol. 2, pp 1651-1740, Raven Press, New York). The term "adenovirus" as used herein, encompasses any one of these adenovirus species. Preferably, an adenovirus according to the invention is a human adenovirus of subfamily group C, namely one of serotypes 1, 2, 5, 6, or 57. More preferably, the term adenovirus applies to two human serotypes, Ad2 and Ad5.

In one preferred embodiment of the invention, the adenovirus is adenovirus serotype Ad5. The adenovirus may be adenovirus serotype Ad5 strain pTG3602. Strain pTG3602 has approximately 15 point mutations scattered throughout the 35,000 nucleotide adenovirus genome, however none of these mutations fall within the E1B gene. Herein, adenovirus type 5 provides a common reference point for the nucleotide numbering convention of viral polynucleotides and amino acid numbering of viral-encoded polypeptides the E1B viral gene region. Those skilled in the art will readily identify the corresponding positions in other adenoviral serotypes. Herein, the term "recombinant" indicates that a polynucleotide construct (e.g. and adenovirus genome) has been generated, in part, by intentional modification by man.

E1B Gene

A virus according to the invention preferably carries a mutation in the sequence of the E1B gene. All serotypes encode a gene that is referred to across serotypes as early region 1B (E1B), encoding gene products of the early phase of DNA replication. Herein, the "E1B gene" refers to the full length transcription unit of the E1B gene in any adenovirus, preferably human adenovirus. A representative example of an E1B gene is that from adenovirus type 5 (Ad5) which has the polynucleotide sequence according to SEQ ID NO: 1. Other examples will be known to the skilled reader and details can be found in commonly used databases, such as, for example Entrez Gene (www.ncbi.nlm.nih.gov/gene). In human adenovirus type 5, the E1B coding region starts at genomic nucleotide number 1714 and ends at the E1B polyA site at genomic nucleotide number 4043. Similar regions are present in all adenoviruses so far tested, for example, including species as diverse as sheep, snake and even bat adenovirus.

The E1B transcription unit of the human adenovirus encodes at least five different splicing isoforms (see FIG. 2) (Takayesu et al. (1994) *J. Gen. Vivol.* 75:789-798). Again, giving the example of Ad5, the major 2.28 kb E1B precursor mRNA encodes two overlapping reading frames, one for the 176 residue E1B-19K protein (E1B-176R) and the other for E1B-55K protein (496 residues; E1B-496R). The E1B-156R, E1B-93R, E1B-84R isoforms (named after the number of amino acids in the expressed product) are generated by alternative splicing of the precursor mRNA for E1B-496R, between a common splice donor (SD1) and one of three splice acceptor sites (SA1-3). The resulting mRNAs encode the 79 amino acids of the E1B-496R N-terminus, and whilst E1B-93R and E1B-84R have unique C-termini, E1B-156R is completed by the 77 C-terminal residues of E1B-496R. Alternative splicing is explained in Kelemen, O., P. Convertini, et al. (2012). "Function of alternative splicing." Gene. It will be apparent to the skilled person that the E1B isoforms in other adenovirus serotypes may have slightly different lengths to those discussed above for Ad5 (e.g. the equivalent of E1B-156R in Ad2 is 155 amino acids long and is therefore often referred to as 155R). Herein, the isoform names E1B-156R, E1B-93R, E1B-84R, E1B-176R and E1B-496R refer to the equivalent isoform of the same approximate size in all adenoviruses, regardless of the actual number of amino acids in the equivalent isoform.

It has been confirmed that the E1B-156R isoform exists in a wide cross-section of adenovirus variants, by using PCR to amplify the specific cDNAs for E1B-156R using start and stop primers specific for each respective E1B-55k gene (FIG. 14). Our experiments show similar splicing patterns in representative viruses from each of the different genera (A-Ad12, B1-Ad3, B2-Ad11, C-Ad5, D-Ad37, E-Ad4 and F-Ad40). Indeed, Ad1wt and Ad57wt have identical E1B-156R protein sequences; Ad2wt and Ad6wt also have identical sequences; and Ad5wt differs only slightly from them all. This makes only three different E1B-156R protein sequences in the entire subfamily C differing at a total of five single amino acid positions and in the length of an internal poly-alanine stretch. Thus it is fully expected that the results demonstrated herein in serotypes Ad2 and Ad5 will be mirrored across other adenovirus variants.

A number of complementation experiments have been performed to show that an increase in E1B-156R is responsible (at least in part) for the increase in Oncolytic Index (OI) that has been observed, such that overexpression of the Ad5-156R gives a potent increase in the OI of adenoviruses generally. In FIGS. 11A, B and C and FIG. 12 herein, it is shown that adenovirus type 5 E1B-156R is a potent enhancer of the OI in the subfamily group C. Furthermore, the E1B-156R equivalent from Ad2wt was shown to have a positive effect on the OI of Ad5wt, meaning that the effect appears not to be limited to one particular adenovirus serotype.

Herein, the E1B-156R isoform of human Ad5 has the polynucleotide sequence according to SEQ ID NO: 2 and the polypeptide sequence according to SEQ ID NO: 3. Herein, the 496R isoform has the polynucleotide sequence according to SEQ ID NO: 4 and a polypeptide sequence according to SEQ ID NO: 5. Herein, the E1B-93R isoform has the polynucleotide sequence according to SEQ ID NO: 6. and the polypeptide sequence according to SEQ ID NO: 7. Herein, the E1B-84R isoform has the polynucleotide sequence according to SEQ ID NO: 8 and the polypeptide sequence according to SEQ ID NO: 9. It will be appreciated by the skilled reader that a degree of variation in sequence exists in naturally-occurring viral variants; accordingly, the invention embraces isoform sequences that differ from the specific sequences set out in the reference sequences referred to about, but are 80%, 85%, 90%, 95%, 98%, 99% or more homologous or identical to those sequences, as calculated by common sequence alignment programs, for example, BLAST (http://blast.ncbi.nlm.nih.gov/Blast.cgi) which can be nucleotide BLAST (blastn) or protein BLAST (blastp). Two sequences are said to be "homologous", as the term is used herein, if one of the sequences has a high enough degree of identity or similarity to the other sequence. "Identity" indicates that at any particular position in the aligned sequences, the nucleotide is identical between the sequences. "Similarity" indicates that, at any particular position in aligned polypeptide sequences, the amino acid residue is of a similar type between the sequences. Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

Accordingly, embodiments of the invention include variant recombinant adenoviruses where the E1B-156R isoform has a polynucleotide sequence that has at least 80% sequence identity to SEQ ID NO: 2 and a polypeptide sequence that has at least 80% sequence identity to SEQ ID NO: 3; where the E1B-496R isoform has a polynucleotide sequence that has at least 80% sequence identity to SEQ ID NO: 4 and a polypeptide sequence that has at least 80% sequence identity to SEQ ID NO: 5; where the E1B-93R isoform has a polynucleotide sequence that has at least 80% sequence identity to SEQ ID NO: 6 and a polypeptide sequence that has at least 80% sequence identity to SEQ ID NO: 7; and where the E1B-84R isoform has a polynucleotide sequence that has at least 80% sequence identity to SEQ ID NO: 8 and a polypeptide sequence that has at least 80% sequence identity to SEQ ID NO: 9. Representative examples of variant E1B-156R isoform sequences are given herein (FIG. 13). Included equivalent sequences to Ad5 E1B-156R are those with 80%, 85%, 90%, 95%, 98%, 99% or more identity with those sequences provided in FIG. 13 (as described above for Ad5). Modulation of isoform levels by engineering.

According to the invention, the level and/or type of splice isoforms of the E1B gene product, expressed from the E1B gene, is modified, and as a result the viruses are rendered oncolytic. The levels and/or types of E1B isoforms may be modulated by any means, for example using ribozymes designed to specifically cleave the E1B isoform mRNAs at selected positions and thereby preventing translation of the mRNAs into functional polypeptide. Alternative methods will be apparent to those of skill in the art, and include insertion of multiple copies of the E1B gene sequence, or forms that encode E1B-156R; activation of regulation of E1B gene expression, or forms that encode E1B-156R, for example by modulation of promoter or enhancer sequences; insertion of regulatory sequences, and so on.

Herein, we provide as particular examples of variant adenoviruses according to the invention, adenoviruses that include one or more mutations in the splicing regions of E1B gene that achieve this effect. As splice site recognition by the spliceosome is known to be affected by mRNA secondary structure, mutations in the E1B gene that affect the secondary structure of its mRNA may also modulate the levels and types of E1B isoforms. For example, the mutation may remove a splice site by changing the polynucleotide and polypeptide sequence of the E1B gene; or may remove a splice site by changing the polynucleotide sequence of the E1B gene and retaining the original polypeptide sequence.

In one embodiment, this effect may be achieved when the E1B gene is mutated in one or more of the splicing recognition regions comprising: a) the splice donor site 1 (SD1); the E1B-93R splice acceptor (SA1); c) E1B-156R splice acceptor (SA2); d) E1B-84R splice acceptor (SA3); and/or e) splice donor site 2 (SD2).

In the example case of Ad5, these splice sites are at the following positions and have the following sequences: SD1 has the sequence GTGGC at position 2251-2255 of the Ad5 genome (position 2256-2260 of the Ad5 genome accession number AC_000008.1 (SEQ ID NO: 41) and position 543-547 in the E1B gene (SEQ ID NO: 1)). The E1B-93R splice acceptor (SA1) has the sequence AACAG at position 3218-3222 of the Ad5 genome (position 3213-3217 of the Ad5 genome accession number AC_000008.1 (SEQ ID NO: 41) and position 1500-1504 in the E1B gene (SEQ ID NO: 1)). The E1B-156R splice acceptor (SA2) has the sequence TTGAG at position 3276-3280 of the Ad5 genome (position 3271-3275 of the Ad5 genome accession number AC_000008.1 (SEQ ID NO: 41) and position 1558-1562 in the E1B gene (SEQ ID NO: 1)). The E1B-84R splice acceptor (SA3) has the sequence TGCAG at position 3595-3599 of the Ad5 genome (position 3590-3594 of the Ad5 genome accession number AC_000008.1 (SEQ ID NO: 41) and position 1877-1881 in the E1B gene (SEQ ID NO: 1)). The splice donor site 2 (SD2) has the sequence GTACT at position 3506-3510 of the Ad5 genome (position 3511-3515 of the Ad5 genome accession number AC_000008.1 (SEQ ID NO: 41) and position 1798-1802 in the E1B gene (SEQ ID NO: 1)). Equivalent sites at equivalent positions in other human serotypes will be easily apparent to those of skill in the art, imbued with the teaching of the present invention.

Accordingly, one aspect of the present invention is a recombinant adenovirus in which where the E1B gene splicing recognition regions are mutated at one or more of the following positions in the Ad5 genome: a) nucleotide 3216 of the adenovirus Ad5 genome (accession number AC_000008.1) (SEQ ID NO: 41) (position 1503 in the E1B gene (SEQ ID NO: 1); b) nucleotide 3218 of the adenovirus Ad5 genome (accession number AC_000008.1) (SEQ ID NO: 41) (position 1505 in the E1B gene (SEQ ID NO: 1); and/or c) nucleotide 3221 of the adenovirus Ad5 genome (accession number AC_000008.1) (SEQ ID NO: 41) (position 1508 in the E1B gene (SEQ ID NO: 1). The E1B gene may contain one or more of the following mutations: a) A3216G in the adenovirus Ad5 genome (position 1503 in the E1B gene (SEQ ID NO: 1)); b) G3218A in the adenovirus Ad5 genome (position 1505 in the E1B gene (SEQ ID NO: 1)); and/or c) G3221A in the adenovirus Ad5 genome (position 1508 in the E1B gene (SEQ ID NO: 1)). Herein, the positions of all point mutations are numbered according to Ad5 genome accession number AC_000008.1 (SEQ ID NO: 41).

The table below identifies the sequences and positions of the splicing recognition regions of the E1B gene in the Ad5 genome. "Ad 5 genome position" and "E1B gene position" correspond to the five residues immediately upstream of splice donor sites (SD1 and SD2), and immediately downstream of splice acceptor sites (SA1, SA2 and SA3).

| E1B splice sites | Ad5 genome position | E1B gene position | Sequence | SEQ ID NO: |
|---|---|---|---|---|
| splice donor 1 (SDI) | 2251-2255 | 538-542 | cag/GTGGCTGAAC | SEQ ID NO: 10 |
| E1B-93R splice acceptor (SA1) | 3218-3222 | 1505-1509 | TCCTTGCATTTGGG TAACAG/gag | SEQ ID NO: 11 |
| E1B-156R splice acceptor (SA2) | 3276-3280 | 1563-1567 | ACACTAAGATATTG CTTGAG/ccc | SEQ ID NO: 12 |
| E1B-84R splice acceptor (SA3) | 3595-3599 | 1882-1886 | GTCTTATGTAGTTTTGTAT CTGTTTTGCAG/cag | SEQ ID NO: 13 |
| splice donor 2 (SD2) | 3506-3510 | 1793-1797 | gag/GTACTGAAAT | SEQ ID NO: 14 |

The "forward slash" indicates the actual splice site.

Mutation of the viral sequence within the splicing recognition regions of the E1B gene can involve either a) removing a splice site by changing the polynucleotide and polypeptide sequence of the E1B gene; or b) removing a splice site by changing the polynucleotide sequence of the E1B gene and retaining the original polypeptide sequence. As the skilled person will appreciate, there is redundancy in the genetic code, i.e. some amino acids are encoded by multiple codons. The splice site sequences can be removed from the transcribed E1B mRNA by mutating the corresponding adenoviral DNA to use (an) alternative codon(s) for the amino acids the polynucleotide sequence is encoding at these sites. Thus, the resulting translated protein will preferably not contain any amino acid changes. The codon table below shows the redundancy in the genetic code.

| Amino Acids | | | Codons |
|---|---|---|---|
| Alanine | Ala | A | GCA GCC GCG GCU |
| Arginine | Arg | R | AGA AGG CGA CGC CGG CGU |
| Aspartic acid | Asp | D | GAC GAU |
| Asparagine | Asn | N | AAC AAU |
| Cysteine | Cys | C | UGC UGU |
| Glutamic acid | Glu | E | GAA GAG |
| Glutamine | Gln | Q | CAA CAG |
| Glycine | Gly | G | GGA GGC GGG GGU |
| Histidine | His | H | CAC CAU |
| Isoleucine | Ile | I | AUA AUC AUU |
| Leucine | Leu | L | CUA CUC CUG CUU UUA UUG |
| Lysine | Lys | K | AAA AAG |
| Methionine | Met | M | AUG |
| Phenylalanine | Phe | F | UUC UUU |
| Proline | Pro | P | CCA CCC CCG CCU |
| Serine | Ser | S | AGC AGU UCA UCC UCG UCU |
| Threonine | Thr | T | ACA ACC ACG ACU |
| Tryptophan | Trp | W | UGG |
| Tyrosine | Tyr | Y | UAC UAU |
| Valine | Val | V | GUA GUC GUG GUU |
| Stop | | | TAA TGA TAG |

In a preferred embodiment, increased levels of the E1B-156R isoform are achieved as a result of a mutated 93R splice site in the E1B gene.

In a preferred embodiment, the E1B gene splicing recognition regions are mutated at one or more of the following positions: a) nucleotide 3216 (e.g. cagGAGG→cggGAGG) of the adenovirus Ad5 genome (accession number AC_000008.1) (SEQ ID NO: 41); b) nucleotide 3218 of the adenovirus Ad5 genome (accession number AC_000008.1) (SEQ ID NO: 41); and/or c) nucleotide 3221 of the adenovirus Ad5 genome (accession number AC_000008.1) (SEQ ID NO: 41). Equivalent mutations in other adenovirus serotypes will be clear to the skilled reader.

In a more preferred embodiment, the E1B gene contains one or more of the following mutations: a) A3216G (cagGAGG→cggGAGG); b) G3218A; and/or c) G3221A, corresponding to positions 1503, 1505 and 1508 in the E1B gene (SEQ ID NO: 1) respectively. Equivalent mutations in other adenovirus serotypes will be clear to the skilled reader.

Levels of Isoforms

Any mutation that is introduced into the sequence of an adenovirus genome should have the effect that the proportion of at least one of the E1B splicing isoforms, E1B-156R, E1B-496R, E1B-93R, and E1B-84R, (and potentially two, three, or all four isoforms) varies with respect to levels that are present in the wild-type under similar conditions. Preferably, the proportion of the E1B-496R isoform is decreased relative to wild-type levels, or even totally shut down. Alternatively, the proportion of the E1B-156R isoform is increased relative to the E1B-496R isoform, the proportion of the E1B-156R isoform is increased relative to the E1B-93R isoform and/or the proportion of the E1B-156R isoform is increased relative to the E1B-84R isoform. These changes in levels of particular isoforms have the effect of enhancing oncolysis, which can also be expressed as enhancing the oncolytic index.

The level of the E1B-156R isoform may be increased relative to the E1B-156R in the equivalent wild type adenovirus sequence. Herein, "increased" means that the proportion of the E1B-156R isoform is increased at least 2-fold, 4-fold, 10-fold, 20-fold, 50-fold, 100-fold, 1,000-fold or 10,000-fold relative to wild type levels.

Herein, "decreased" means that the proportion of the E1B-496R isoform is decreased at least 2-fold, 4-fold, 10-fold, 20-fold, 50-fold, 100-fold, 1,000-fold or 10,000-fold relative to wild type levels.

Herein, "wild type levels" refers to the levels of E1B-156R, E1B-496R, E1B-93R, and E1B-84R isoforms that are evident by expression of these proteins from the wild-type adenovirus, with no mutations in the E1B gene reference sequence (i.e. SEQ ID NO: 1). For example, the proportion of the mutant Ad5 E1B-156R isoform may be increased relative to levels in wild-type Ad5 adenovirus, such that mutant adenovirus has an oncolytic effect in a cancer cell. Mutant Ad2 E1B-156R isoform may be increased relative to levels in wild-type Ad2 adenovirus.

Preferred viruses according to the invention may have diminished or inhibited expression of E1B-93R, and preferably do not express E1B-93R. By "does not express" is meant herein that the detectable level of the E1B-93R sequence is less than 50%, 10%, 1% of the level of the E1B-93R sequence in the wild type adenovirus under equivalent conditions, preferably less than 0.1%, less than 0.01% or even less. This has the effect of raising the expression of E1B-156R.

Preferably, an optimal ratio of the E1B-156R, E1B-496R, E1B-93R, and E1B-84R isoform protein levels would lie along the lines of about 67:0:0:33 as compared to about 5:70:10:15 for wild-type viruses. As the skilled reader will appreciate, however, it is difficult or impossible to be exact about relative levels of this type since they are dependent on the point in the infection cycle assessed, i.e. early/intermediate/late. The ratios changes for the benefit of the shorter spliceforms at the cost of 496R (which is the unspliced, full-length RNA). In particular, favoured ratios of the E1B-156R isoform to the E1B-496R isoform are 2:1, 5:1, 10:1, 20:1, 50:1, 100:1, 1000:1 or 10,000:1 or more. A ratio of 100:1 or more is preferred.

Herein reference to "the proportion" of the E1B-156R, E1B-496R, E1B-93R, or E1B-84R isoforms refers to: a) the level of the isoform protein that is expressed; and/or b) the level of the isoform mRNA that is produced.

Techniques for measuring mRNA levels will be known to those of skill in the art for the quantitation of polynucleotides, such as, for example, nucleic acid amplification, for instance PCR, RT-PCR, TaqMan-based methodologies, RNase protection, Northern blotting and in situ hybridization techniques, and quantitative versions of these methods. Changes in mRNA expression levels may be of a temporal, spatial or quantitative nature. The number of copies of each E1B isoform mRNA can be calculated and compared to a reference, for example a house keeping gene such as beta-actin or GAPDH or a plasmid carrying the specific "amplicon of interest".

If polypeptide levels are to be monitored, any assay technique can be used that can determine levels of a specific polypeptide, including radioimmunoassays (RIA), competitive-binding assays, Western Blot analysis, FACS and enzyme-linked immunosorbent (ELISA) assays. Antibodies which specifically bind to particular splice isoforms may be used, for example. The antibodies may be used with or without modification, and may be labelled by joining them, either covalently or non-covalently, with an analytically-detectable reagent such as a radioisotope, a fluorescent molecule or an enzyme or other reporter molecule. A wide variety of reporter molecules known in the art may be used.

E1B Isoforms

Very little is known about the E1B-156R, E1B-93R, E1B-84R isoforms. Production of different E1B mRNAs is regulated during the infection process. While mainly the 2.28 kb form is produced early in infection, the proportion of shorter spliced mRNAs increases over time and the E1B-84R transcript becomes predominant in the late phase of infection. The isoform protein expression closely follows the transcription pattern of the mRNAs (Chow et. al (1979) *J. Mol. Biol.* 134:265-303; Montell et. al (1984) *Mol. Cell. Biol.* 4:966-972; Spector et. al (1978) *J. Mol. Biol.* 126:395-414; Virtanen and Pettersson (1985) *J. Vivol.* 54:383-391; Wilson and Darnell (1981) *J. Mol. Biol.* 148:231-251).

It has been shown that different spliceotypes can interact both hetero- and homogeneously with each other through the N-terminus, and the C-terminus must carry specific functions that cannot be complemented for by alternative E1B spliceotypes. When infecting with viruses lacking the expression of a specific spliceotype the viability loss can be complemented by co-transfecting with an expression plasmid for corresponding spliceotype. The co-transfection with an alternative spliceotype does not complement the loss.

Mutant Adenoviruses

The table below summarises the details of some representative adenovirus mutants in provided as examples of the teaching of the invention, along with some experimental control viruses.

| Virus | Mutations[a] | Description |
|---|---|---|
| Ixovex | A3216G | E1B-93R splice site mutant |
| | | Does not express E1B-93R isoform |
| | | Destabilises E1B-496R due to sequence change |
| | | Increases in E1B-156R levels |
| Ixo-ctrl | | Control (wild-type) virus |
| Ixo-156 | T3272G/ G3275A | E1B-156R splice acceptor site mutant |
| | | Does not express E1B-156R isoform |
| | | E1B-496R sequence is not changed |
| | | Expresses other E1B gene products |
| | | 93R levels increase |
| Ixo-93 | G3218A/ G3221A | E1B-93R splice acceptor site mutant |
| | | Does not express E1B-93R isoform |
| | | E1B-496R sequence is not changed |
| | | Increases in E1B-156R levels |
| Ixo-SD | G2255A/ T2258C | E1B splice donor 1 site mutant |
| | | Does not express E1B-93R, -156R and -84R isoforms |
| | | E1B-496R sequence is not changed |
| Ixo-Stop | G2274T | Inserts a stop codon downstream of the E1B splice donor 1 site |
| | | Does not express E1B-496R protein |
| | | Expresses E1B-93R, -156R and -84R isoforms |

[a]Numbered according to position in the Ad5 genome accession number AC_000008.1 (SEQ ID NO: 41)

The adenovirus herein termed the Ixovex virus has diminished or inhibited expression of E1B-93R, and preferably does not express E1B-93R. By "does not express" is meant herein that the detectable level of the E1B-93R sequence is less than 50%, 10%, 1% of the level of the E1B-93R sequence in the wild type adenovirus under equivalent conditions, preferably less than 0.1%, less than 0.01% or even less. This has the effect of raising the expression of E1B-156R.

Additionally, in this virus the full length E1B protein E1B-496R is destabilized. By "destabilised" is meant that the protein becomes substantially undetectable due to the mutation. This leaves only E1B-156R and E1B-84R still expressed from the 496 reading frame. The unstable nature of E1B-55k is discussed in Gabler et al. 1998 J. Virol.; and Gonzalez 2002, J. Virol.

The efficacy of Ixovex as compared to H101 suggests that to some extent, E1B-496R and E1B-156R have overlapping functions (Sieber et. al. (2007) J. Virol. 81 (1): 95-105). E1B-496R and E1B-156R have been found to bind many similar factors. E1B-156R can bind to E4orf6, the binding partner with which E1B-496R utilises most of its important functions. Interestingly, E1B-156R has also been found to bind p53, although with less affinity. E1B-156R can substitute for E1B55k in cell transformation experiments. Also, E1B-156R induces tumours in in vivo models, when overexpressed together with E1A. Specifically, the E1B-156R spliceomer was found herein to have a cell transforming potential separate from the E1B-496R protein.

It is an advantage of the present invention that in order to achieve the described oncogenic effect, viruses according to the present invention do not require the deletion of the whole of the E1B gene.

Methods of Generating Recombinant Viruses

The invention provides polynucleotides encoding the recombinant adenoviruses, optionally encoded within a vector suitable for virus production in a host cell.

The invention provides host cells comprising polynucleotides encoding the recombinant adenovirus.

The invention also includes a method of rendering an adenovirus oncolytic. Such a method involves engineering a mutant adenovirus in which the sequence of the E1B gene has been modified so as to increase the level of the E1B-156R isoform relative to the level in the equivalent wild-type adenovirus. The adenovirus type can be any of those described above, and is preferably a human adenovirus of subfamily group C, namely one of serotypes 1, 2, 5, 6, or 57, even more preferably, the term adenovirus applies to two human serotypes, Ad2 and Ad5. Similarly, the mutation may be any one of those described or exemplified herein. In certain embodiments, a hybrid virus may be engineered, for example, in which an E1B-156R from one adenovirus variant is expressed in another adenovirus variant. For example, an Ad2 E1B-156R may be expressed in an Ad5 adenovirus; it has been shown herein that adding Ad2 E1B-156R to Ad5 increases oncolytic activity by 10-fold.

Suitable techniques to engineer mutations in alternative adenoviruses will be known to those of skill in the art. A preferred method could be to use the widely used pShuttle system (Agilent Technologies) or use the method developed by Dr. Oberg (the inventor of IXOvex and board member of IXOgen)) using the pSuperShuttle system (see Ingemarsdotter, C. K., S. K. Baird, C. M. Connell, D. Oberg, G. Hallden, and I. A. McNeish. 2010. Low-dose paclitaxel synergizes with oncolytic adenoviruses via mitotic slippage and apoptosis in ovarian cancer. Oncogene 29:6051-6063). This allows the insertion or mutation of any sequence anywhere in the adenovirus, which pShuttle cannot do, being limited to the end regions of the adenoviral genome. Shortly, the flanking sequences (left and right arm) of the region of interest may be cloned into the pSuperShuttle plasmid on each side of an antibiotic selection gene (ASG). If a mutation of any sort (substitution, deletion or addition) is desired it can be incorporated in either arm. For the insertion of a gene of interest or a whole expression cassette into the virus the extensive multiple cloning sites on each side of the ASG may be used. When the complete pSupershuttle construct is sequenced and ready it is fused with the virus by homologous recombination. The inserted ASG allows for positive selection. The ASG is digested away leaving a small scar in the form of a unique restriction enzyme site, which can be used in future modifications of the virus. Other suitable variations on this technique will be known to those of skill in the art.

Construction of Adenovirus E1B-55K Mutants

Methods for the construction of adenoviral mutants are generally known in the art. See, Mittal (1993) Virus Res., 28: 67-90 and Hermiston et al., Methods in Molecular Medicine: Adenovirus Methods and Protocols (1999) ed. Wold, Humana Press. Further, the adenovirus 5 genome is registered as NCBI Reference Sequence: AC_000008.1, and the virus is available from the American Type Culture Collection, Rockville, Md., U.S.A., under accession number: VR-1516.

Generally, adenovirus vector construction involves an initial deletion or modification of a desired region of the adenoviral genome, preferably the Ad5 genome, in a plasmid cassette using standard techniques.

Certain of the materials and methods used to construct adenovirus mutants are described by Hanke et. al. (1990) Virology, 177: 437-444 and Bett et. al., (1993) J. Virol. 67: 5911-5921, and in PCT/CA96/00375. Many of the materials used to construct adenovirus mutants are provided commercially. See also, Hermiston et al., Methods in Molecular Medicine: Adenovirus Methods and Protocols (1999) ed. Wold, Humana Press. Other details are provided herein.

Cell lines that were used to conduct the experiments described herein are readily available from recognised depositary institutions. For example, the following cell lines were used herein to assess cytotoxicity: H1299, FaDu, H460, A549, HeLa, Hek293, JH293 and NHBE.

A preferred procedure for constructing the adenoviral E1B gene mutants of the present invention is to make site-specific mutations in the adenoviral genome in a plasmid cassette using well established techniques of molecular biology, or modifications of these techniques, referred to herein. This can be realized using various materials and methods.

Methods of Treating Cancer

The invention provides recombinant adenoviruses that produce an oncolytic effect in a cancer cell. The cancer cell may be a neoplastic cell. The invention also provides novel methods of treating cancer, characterised by neoplastic cells. The neoplastic cells may preferably substantially lack p53 function ($p53^{(-)}$). Such a method may comprise:

a) administering a dose of the recombinant adenovirus according to the invention, that carries a mutation in the E1B gene, to a patient in need of treatment;

b) allowing sufficient time for the recombinant adenovirus to infect neoplastic cells of said cancer, wherein the mutant adenovirus has an oncolytic effect which is selective for the cancer cells relative to the non-neoplastic cells; and c) optionally administering further doses of the recombinant adenovirus.

The cancer cell or neoplastic cell may substantially lack p53 function.

The invention provides recombinant adenoviruses for use as a therapeutic agent in treating a patient with cancer. Preferably the cancer is characterised by neoplastic cells. Preferably, those neoplastic cells substantially lack p53 function.

The invention also provides compositions comprising recombinant adenoviruses of the invention.

The invention provides pharmaceutical compositions comprising a recombinant adenovirus of the invention.

The invention also provides processes for making a pharmaceutical composition involving combining a recombinant adenovirus of the invention with a pharmaceutically acceptable carrier.

The compositions may additionally comprise an agent for chemotherapy.

The present invention provides several novel methods and compositions for ablating neoplastic cells by infecting the neoplastic cells with a recombinant adenovirus which is substantially replication-deficient in non-neoplastic cells and which exhibits at least a partial replication phenotype in neoplastic cells. The difference in replication phenotype of the adenovirus constructs of the invention in neoplastic and non-neoplastic cells provides a biological basis for viral-based therapy of cancer.

A cell population (such as a mixed cell culture, human cancer patient or non-human mammalian subject) which comprises a subpopulation of neoplastic cells lacking p53 function and a subpopulation of non-neoplastic cells which express essentially normal p53 function can be contacted under infective conditions (i.e. conditions suitable for adenoviral infection of the cell population, typically physiological conditions) with a composition comprising an infectious dosage of a E1B-p53$^{(-)}$ replication inhibited adenovirus. Such a contacting step results in infection of the cell population with the E1B-p53$^{(-)}$ replication-deficient adenovirus. The infection produces preferential expression of a replication phenotype in a significant fraction of the cells comprising the subpopulation of neoplastic cells lacking p53 function, but does not produce a substantial expression of a replicative phenotype in the subpopulation of non-neoplastic cells having essentially normal p53 function. The expression of the replication phenotype in an infected p53$^{(-)}$ cell results in the death of the cell, such as by the cytopathic effect (CPE), cell lysis, apoptosis, or similar, resulting in a selective ablation of neoplastic p53$^{(-)}$ cells from the cell population.

It is desirable for the mutant virus to be replicable and to form infectious virions containing the mutant viral genome which may spread and infect other cells, thus amplifying the anti-neoplastic action of an initial dosage of mutant virus.

Herein, E1B-p53$^{(-)}$ replication inhibited adenovirus constructs suitable for selective killing of p53$^{(-)}$ neoplastic cells are those described above.

Candidate antineoplastic adenovirus mutants may be further evaluated by their capacity to reduce tumourigenesis or neoplastic cell burden in nu/nu mice harbouring a transplant of neoplastic cells lacking p53 function, as compared to untreated mice harbouring an equivalent transplant of the neoplastic cells.

Antineoplastic replication-deficient adenovirus mutants may be formulated for therapeutic, prophylactic and, potentially, diagnostic administration to a patient having a neoplastic disease. For therapeutic or prophylactic uses, a sterile composition containing a pharmacologically effective dosage of one or more species of antineoplastic replication inhibited adenovirus mutant is administered to a patient for treatment of a neoplastic condition. A pharmaceutically acceptable carrier or excipient is often employed in such sterile compositions. A variety of aqueous solutions can be used, e.g., water, buffered water, 0.4% saline, 0.3% glycine and the like. These solutions are sterile and generally free of particulate matter other than the desired adenoviral virions. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. Excipients which enhance infection of cells by adenovirus may be included.

Therapy of neoplastic disease may be afforded by administering to a patient or subject a composition comprising replication-defective adenoviruses of the invention. Various human and mammalian neoplasms comprising cells that lack p53 function may be treated with the replication inhibited adenoviral constructs. For example (but not limiting to), a human patient or non-human mammal having a bronchogenic carcinoma, nasopharyngeal carcinoma, laryngeal carcinoma, small cell and non-small cell lung carcinoma, lung adenocarcinoma, hepatocarcinoma, pancreatic carcinoma, bladder carcinoma, colon carcinoma, breast carcinoma, cervical carcinoma, ovarian carcinoma, or lymphocytic leukaemias may be treated by administering an effective antineoplastic dosage of an appropriate replication inhibited adenovirus.

Suspensions of infectious adenovirus particles may be applied to neoplastic tissue by various routes, including intravenous, intraperitoneal, intramuscular, subdermal, and topical. A adenovirus suspension, preferably an aqueous suspension, containing between about $10^3$ to $10^{15}$ or more virion particles per ml (such as between about $10^5$ to $10^{12}$ or more virion particles per ml, between about $10^7$ to $10^{10}$ or more virion particles per ml, or about $10^9$ virion particles per ml) may be inhaled as a mist (e.g. for pulmonary delivery to treat bronchogenic carcinoma, small-cell lung carcinoma, non-small cell lung carcinoma, lung adenocarcinoma, or laryngeal cancer). Alternatively, such a suspension may be swabbed directly on a tumour site for treating a tumour (e.g. bronchogenic carcinoma, nasopharyngeal carcinoma, laryngeal carcinoma, cervical carcinoma) or may be administered by infusion (e.g. into the peritoneal cavity for treating ovarian cancer, into the portal vein for treating hepatocarcinoma or liver metastases from other non-hepatic primary tumours) or other suitable route, including direct injection into a tumour mass (e.g. a breast tumour), enema (e.g. colon cancer), or catheter (e.g. bladder cancer).

Replication inhibited viruses may also be delivered to neoplastic cells by liposome or immunoliposome delivery; such delivery may be selectively targeted to neoplastic cells on the basis of a cell surface property present on the neoplastic cell population (e.g. the presence of a cell surface protein which binds an immunoglobulin in an immunoliposome). For example, a suspension of replication inhibited adenovirus virions can be encapsulated in micelles to form immunoliposomes by conventional methods (for example see U.S. Pat. No. 5,043,164, U.S. Pat. No. 4,957,735, U.S. Pat. No. 4,925,661; Connor and Huang (1985) *J. Cell Biol.* 101: 582; Lasic D D (1992) *Nature* 355: 279; *Novel Drug Delivery* (1989) eds. Prescott and Nimmo, Wiley, New York; and Reddy et al. (1992) *J. Immunol.* 148: 1585). Immunoliposomes comprising an antibody that binds specifically to a cancer cell antigen (e.g., CALLA, CEA) present on the cancer cells of the individual may be used to target virions to those cells.

The compositions containing the present antineoplastic replication-deficient adenoviruses or cocktails thereof can be administered for prophylactic and/or therapeutic treatments of neoplastic disease. In therapeutic application, compositions are administered to a patient already affected by the particular neoplastic disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration.

In prophylactic applications, compositions containing the antineoplastic replication inhibited adenoviruses or cocktails thereof are administered to a patient not presently in a neoplastic disease state to enhance the patient's resistance to recurrence of a neoplasm or to prolong remission time. Such an amount is defined to be a "prophylactically effective dose." In this use, the precise amounts again depend upon the patient's state of health and general level of immunity.

Single or multiple administrations of the compositions can be carried out with dose levels and pattern being selected by the treating physician. In any event, the pharmaceutical formulations should provide a quantity of the antineoplastic replication inhibited adenoviruses of this invention sufficient to effectively treat the patient.

Antineoplastic replication inhibited adenoviral therapy of the present invention may be combined with other antineoplastic protocols, such as conventional chemotherapy.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The practice of the present invention will employ, unless otherwise indicated, conventional techniques of molecular biology, microbiology, recombinant DNA technology and immunology, which are within the skill of those working in the art.

Most general molecular biology, microbiology recombinant DNA technology and immunological techniques can be found in Sambrook et al., *Molecular Cloning, A Laboratory Manual* (2001) Cold Harbor-Laboratory Press, Cold Spring Harbor, N.Y. or Ausubel et al., *Current protocols in molecular biology* (1990) John Wiley and Sons, N.Y.

Unless defined otherwise, all technical and scientific terms used herein have the same meaning as commonly understood by one of ordinary skill in the art to which this invention belongs.

BRIEF DESCRIPTION OF DRAWINGS

FIG. 9. Ixovex shows more than 500-fold less cytotoxicity to normal cells compared with the unmodified virus (Ad5wt). Presented is the fold inhibition of cytotoxicity in relation to Ad5wt (bottom row) and the raw $EC_{50}$ values (top row). The cytotoxicity was measured at 6 dpi using the MTS assay.

FIG. 12. Table showing the 48 hpi data points for FIGS. 11A-C (except for the H460 data points which were collect 72 hpi) and calculation of oncolytic indices, where OI=((a/b)/(c/d)). a=pfu/cellcancer cells+156R, b=pfu/cellnormal cells+156R, c=pfu/cellcancer cells−156R, d=pfu/cellnormal cells−156R.

EXAMPLES

Figure 1:
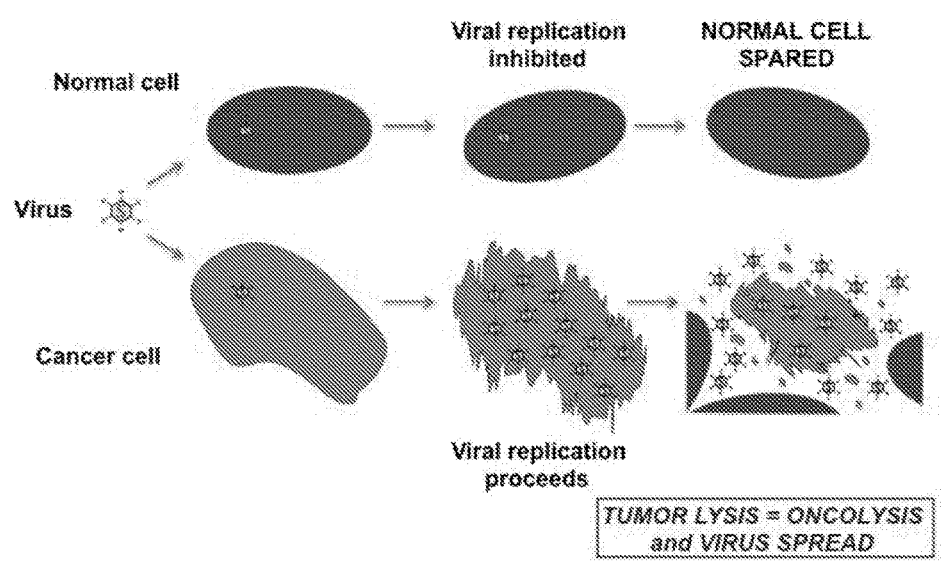
FIG. 1. Schematic description of an oncolytic virus.
Figure 2:
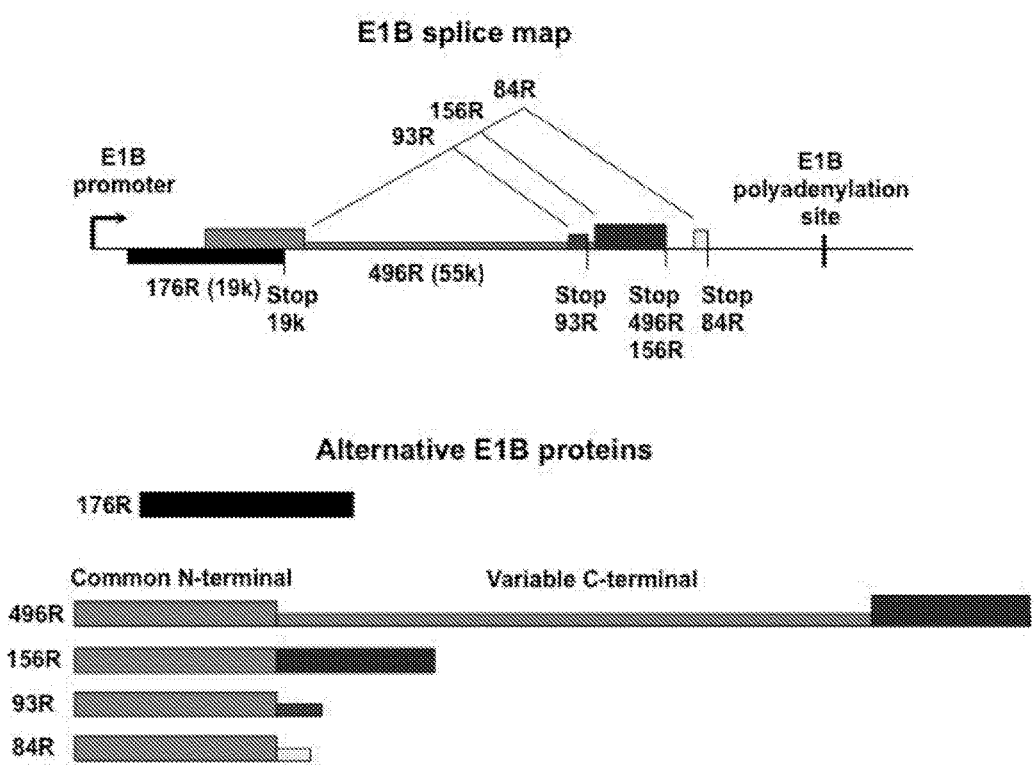
FIG. 2. E1B splice map showing alternative E1B gene products. The full-length E1B transcript carries the E1B-176R and E1B-496R open reading frame (ORF). Through alternative splicing in the E1B-496 ORF another three proteins, E1B-93R, E1B-156R and E1B-84R, are expressed. The lesser proteins have the 79 amino terminal amino acids in common with E1B-496R but differ in the carboxy terminal, except for E1B-156R, which splices in frame with E1B-496R.

Materials and Methods
Virus Construction

Nucleotides 1-5055 of adenovirus serotype 5 (Ad5) were PCR amplified with Phusion PFU polymerase using Ad5start (SEQ ID NO:15—ccacctcgagttaattaacatcat-caataatataccttattttg) and Ad5wt5055as (SEQ ID NO: 16—gtgggtttaaacggatttggtcagggaaaacatg) oligonucleotides. Viral genomic DNA extracted from a CsCl purified Ad5 batch was used as a template. The PCR product was cloned into pShuttle (Stratagene) using restriction enzymes NotI and PmeI (NEB). To produce E1B 93R splice site mutations in pShuttle-5055, the oligonucleotides Mut93Rs (SEQ ID NO: 17—ccttgcatttgggtaatagaagaggagtgttcctaccttaccaatg) and Mut93Ras (SEQ ID NO: 18—cattggtaaggtaggaacactc-ctcttctattacccaaatgcaagg) were used in a PCR Mutagenesis XL reaction (Stratagene), according to manufacturers' instructions. Clones were screened and sent for sequencing. Five μg of the correct clone were linearised using PmeI (NEB), phenol/chloroform-treated and ethanol precipitated. Two hundred ng were mixed together with 100 ng of the pTG3602 plasmid. The mixture was electroporated into BJ5183 cells (Stratagene) and plated onto kanamycin (25 μg/ml) containing agar-plates. Clones were screened by size exclusion on a cracking gel. Briefly, the pellet of 1 ml bacterial culture was resuspended in 50 μl water and treated with 50 μl phenol/chloroform. The mixture was spun for 1 min at 13,000 rpm and the water phase collected. The water phase containing all DNA and RNA from the bacteria was treated for 5 min with DNA loading dye containing RNaseH and then run on a 0.7% agarose gel. DNA was prepared from the selected clones (Qiagen Maxi Prep kit) and sequenced to ensure the correct mutation had been introduced. Five μg of correct pT3602 mutant were digested with PacI to excise the viral genome, phenol/chloroform treated and ethanol precipitated. Two μg of the digested plasmid were transfected into 10e5 Hek293 cells in a 6-well plate using Transfectene (Biorad). Five days later the cells were harvested, subjected to three rounds of freeze/thawing and applied to a T175 bottle 80% subconfluent with A549 cells for bulking up of infected cell lysate.

A CF-10 (Thermo Scientific) was seeded with Hek293 cells and infected at 80% confluency with a third of the cell lysate. Three days later the CF-10 was harvested. The cell pellet was freeze/thawed three times, centrifuged to clear the lysate and applied to a 1.25/1.4 g/ml CsCl gradient and spun at 25,000 rpm in an ultracentrifuge. The virus band was collected with a 21 G syringe and distributed into 1.35 g/ml CsCl columns. The columns were spun at 40,000 rpm overnight and the virus band was collected with a 21 G syringe. The extracted virus was injected into a Slide-A-Lyzer (Thermo Scientific) cassette and dialysed overnight at 4° C. into 50 mM TRIS pH 7.8, 150 mM NaCl, 1 mM MgCl$_2$, 10% glycerol. The virus activity, assessed by the 50% tissue culture infective dose (TCID$_{50}$) (pfu/ml), was then determined by using JH293 cells as described in the Viral Replication section below. Viral DNA was purified from a small aliquot and the number of viral genomes per μl (particles/μl) was determined using a spectrophotometer. The ratios between the particles and activities of all viruses used herein were less than 20. Ixo-ctrl virus is a wild-type clone from the adenoviral serotype 5 strain pTG3602.

In parallel, pShuttle plasmids were made in which all splice sites were individually mutated without changing the amino acid sequence of the E1B-496R protein, using the PCR Mutagenesis XL Kit (Stratagene) according to manufacturers' recommendations.

| Oligonucleotides for PCR Mutagenesis | Oligonucleotide sequences | SEQ ID NO: |
|---|---|---|
| Ixo-CtrlS (wt) | CTTGCATTTGGGTAACAGg aggggggtgttcctacc | SEQ ID NO: 19 |
| Ixo-CtrlAS (wt) | ggtaggaacacccccctc CTGTTACCCAAATGCAAG | SEQ ID NO: 20 |
| Ixo-156Rs | ctaaGATATTGCTgGA acccgagagcatgtcc | SEQ ID NO: 21 |
| Ixo-156Ras | ggacatgctctcgggtTCc AGCAATATCttag | SEQ ID NO: 22 |
| Ixo-93Rs | CATTTGGGTAACAG aagagggtgttcc | SEQ ID NO: 23 |
| Ixo-93Ras | ggaacacccctctt CTGTTACCCAAATG | SEQ ID NO: 24 |
| Ixo-SDs | gaatgaatgttgtacaaGTc GCTGAACTGTATC | SEQ ID NO: 25 |
| Ixo-SDas | GATACAGTTCAGCgACttgt acaacattcattc | SEQ ID NO: 26 |
| Ixo-StopS | gtggctgaactgtatccataac tgagacgcattttg | SEQ ID NO: 27 |
| Ixo-StopAS | caaaatgcgtctcagttatgg atacagttcagccac | SEQ ID NO: 28 |
| IxovexSense | CATTTGGGTAACGGG aggggggtgttcc | SEQ ID NO: 39 |
| IxovexAS | ggaacacccccct CCCGTTACCCAAATG | SEQ ID NO: 40 |

All these pShuttle plasmid were used in homologous recombination to generate a large set of viruses (see table 1).

TABLE 1

Adenovirus mutants provided by the invention.

| Virus | Mutations[a] | Description |
|---|---|---|
| Ixovex | A3216G | E1B-93R splice site mutant<br>Does not express E1B-93R isoform<br>Destabilises E1B-496R due to sequence change<br>Increases in E1B-156R levels |
| Ixo-ctrl | | Control (wild-type) virus |
| Ixo-156 | T3272G/<br>G3275A | E1B-156R splice acceptor site mutant<br>Does not express E1B-156R isoform<br>E1B-496R sequence is not changed<br>Expresses other E1B gene products<br>93R levels increase |
| Ixo-93 | G3218A/<br>G3221A | E1B-93R splice acceptor site mutant<br>Does not express E1B-93R isoform<br>E1B-496R sequence is not changed<br>Increases in E1B-156R levels |

TABLE 1-continued

Adenovirus mutants provided by the invention.

| Virus | Mutations[a] | Description |
|---|---|---|
| Ixo-SD | G2255A/ T2258C | E1B splice donor 1 site mutant<br>Does not express E1B-93R, -156R and -84R isoforms<br>E1B-496R sequence is not changed |
| Ixo-Stop | G2274T | Inserts a stop codon downstream of the E1B splice donor 1 site<br>Does not express E1B-496R protein<br>Expresses E1B-93R, -156R and -84R isoforms |

[a]Numbered according to position in the Ad5 genome accession number AC_000008.1 (SEQ ID NO: 41).

Tissue Culture

All cells were cultured at 37 C and 5% $CO_2$ and were tested regularly for mycoplasma contamination. The cell lines used in this study are listed below.

| Cell name | Type | Culture medium | Source |
|---|---|---|---|
| H1299 | Non-small cell lung carcinoma | DMEM + 10% FCS | BCI* |
| FaDu | Pharyngeal squamous cell carcinoma | DMEM + 10% FCS | BCI |
| H460 | Large cell lung carcinoma | DMEM + 10% FCS | BCI |
| A549 | Non-small cell lung carcinoma | DMEM + 10% FCS | Uppsala University |
| HeLa | Cervical Cancer | DMEM + 10% FCS | BCI |
| Hek293 | Human Embryonic Kidney cells | DMEM + 10% FCS | Uppsala University |
| JH293 | Human Embryonic Kidney cells | DMEM + 10% FCS | Uppsala University |
| NHBE | Normal Human Bronchial Epithelial | Bullet Kit (Lonza) | Lonza |

Cytotoxicity Assay

We used the 3-(4,5-dimethylthiazol-2-yl)-5 (3-carboxymethoxyphenyl)-2-(4-sulfophenyl)-2H-tetrazolim (MTS) assay (CellTiter 96 Aqueous Non-Radioactive Cell Proliferation Assay; Promega, Wis., USA) to assess the cytotoxicity of Ixovex and the control viruses. Aiming for cells to be confluent on day 6, 1,000-4,000 cells/well (depending on the rate of growth) were seeded in a 96 well plate in 90 μl of medium and 5% FCS. Viruses (in 10 μl of medium and 5% FCS) were added 18 hours later at nine 1:10 serial dilutions starting at 10,000 viral particles (vp)/cell, together with a positive (just cells with no virus) and a negative control (no cells just medium).

Six days following infection, survival was determined using MTS assay. MTS was mixed with phenazinemethosulphate (PMS) at 20:1 ratio and added to the cells. Following three hours of incubation, absorbance was measured at 490 nm using the Opsys MR 96-well μplate reader and Revelation Quicklink 4.04 software (Dynex Technologies, Virginia, USA). The values were established for each dilution and compared to negative control (100% cell death), and positive control (0% cell death). $EC_{50}$ values (half maximum effective concentration to kill 50% of cells—$EC_{50}$) were calculated by non-linear regression (sigmoidal dose-response curve) using GraphPad Prism (GraphPad Software, California, USA), utilising the following formula:

$$Y = \text{bottom} + (\text{top} - \text{bottom})/1 + 10^{[log_{10} EC_{50} - X] \times Hill\ slope}$$

Y is the response and starts at 'bottom' and goes to the 'top' in a sigmoidal fashion.

All experiments were performed in triplicate.

Viral Replication Assay

Cells were seeded in 6-well plate in medium with 10% FCS 24 hours prior to infection. 100 vp/cell were used to infect 80% confluent cells in a 2% FCS medium. Two hours after infection, the medium was replaced with a 10% FCS medium (primary infection). At hours post-infection (specified in respective figure), medium and cells were harvested (by scraping), frozen and thawed three times in liquid nitrogen and 37° C., respectively and stored at −80° C. until used. JH293 cells were seeded at 10,000 cells per well in a 96-well plate in 200 μl medium with 5% FCS. In the first row of the TCID50 the initial dilution of the different samples was between undiluted to 1:1000 dependent on hpi and virus, these dilutions from the primary infection were used to infect JH293 cells. The last row was left uninfected as a negative control. Between day 9 and 11, plates were inspected for cytopathogenic effect (CPE). The 50% tissue culture infective dose ($TCID_{50}$) and number of pfu/cell (cell count on the day of infection) were calculated using Reed-Muench accumulative method. See example below:

Example of a 96-well plate(+ indicate well with evidence of CPE):

| Dilution | | | | | | | | | | | | | % with CPE |
|---|---|---|---|---|---|---|---|---|---|---|---|---|---|
| $10^{-3}$ | + | + | + | + | + | + | + | + | + | + | + | + | 100% |
| $10^{-4}$ | + | + | + | + | + | + | + | + | + | + | + | + | 100% |
| $10^{-5}$ | + | + | + | + | + | + | + | + | + | + | + | + | 100% |
| $10^{-6}$ | | | + | + | | | + | | + | | | | 42% |
| $10^{-7}$ | | | | | | | | | | | | | 0% |
| $10^{-8}$ | | | | | | | | | | | | | 0% |
| $10^{-9}$ | | | | | | | | | | | | | 0% |
| Negative controls | | | | | | | | | | | | | |

Calculate the proportionate distance: (% next above 50% − 50%)/(% next above 50% − % next below 50%) = (100% − 50%)/(100% − 42%) = 0.86
Calculate the 50% end point: $log_{10}$ (dilution in which position is next above 50%) = $log_{10}$ $10^{-5}$ = −5
Combine the values to obtain $log_{10}$ $TCID_{50}$ = −5 − 0.86 = −5.86
$TCID_{50}$ titre = $10^{-5.86}$ (or 1 in 7.24 × $10^5$ dilution of the amount added to the top row). As 22 μl (0.022 ml) was added to the top row, $TCID_{50}$/ml = 7.24 × $10^5$/0.022 = 3.29 × $10^7$
Multiple by a constant: 3.29 × $10^7$ × 0.69 = 2.27 × $10^7$ pfu/ml For pfu/cell, multiply the above with the volume of virus added to each well of the 6-well plate (2 ml) and divide by the cell count on the day of infection (e.g. 2.4×$10^5$): (2.27× $10^7$×2)/2.4×$10^5$=189 pfu/cell.

Western Blot

A549 cells or H1299 were infected with 5 pfu/cell, total protein was extracted at 48 h post infection using RIPA buffer. Protein concentration was determined using Bradford reagent. Twenty μg total protein from each sample were loaded onto a 10% PAGE gel. The proteins were transferred to a PVDF (BioRad) membrane by wet blotting. The membrane was blocked using 3% BSA TBS solution for 1 h. Primary antibodies used were: Ad capsid proteins (AbCam-6982), E1B-55k (2A6, Sarnow, Sullivan Levine 1982, dilution 1:500), E1A (Santa cruz, M73), actin (Santa Cruz, 1-19) and p53 (Cell Signalling, #9282). All antibodies were diluted as recommended in 1.5% BSA TBS. Membranes were incubated with the primary antibodies for 15-24 hours at 4° C. where after they were washed with 1×TBS 3% Tween-20 three times for 10 min. HRP-coupled secondary antibodies against respective primary antibody were diluted 1:5000 in 1.5% BSA TBS and applied to the membrane for 1 h. After removing the antibody dilution the membranes were washed with 1×TBS 3% Tween-20 three times for 10 min. Each membrane was exposed for 1 min with ECL Plus (GE, RPN2132). After having been wrapped in plastic foil the membranes were put in a Hypercassette together with Hyperfilm (GE) and the films were developed at selected time intervals. Alternatively, secondary antibodies labelled with IRDyes from LI-COR were used. Analysis was carried out using an Odyssey Imager.

RT-PCR

A549 cells were infected with 5 pfu/cell of respective virus, total RNA was extracted at 48 h post infection using Trizol (Invitrogen). The RNA was DNAse treated (NEB, DNase I), phenol/chloroform treated and ethanol precipitated. One μg total RNA was used to synthesise cDNA (Invitrogen, SuperScript® III) according to manufacturers' recommendations. cDNA was used as template in PCR (NEB Taq DNA Polymerase) reactions with a common sense oligonucleotide (55kSense, SEQ ID NO: 29—gcctgctactgt-tgtcttccg) and either of the following antisense nucleotides: 93Ras, SEQ ID NO: 30—caccccctcctgtacaac, 156Ras, SEQ ID NO: 31—gacatgctctcgggctgtacaac or 84Ras, SEQ ID NO: 32 caaacgagttggtgctcatg. The amplicon length of each was about 200 nucleotides. The PCR reaction was stopped after 20 cycles and an aliquot run on a 2% agarose gel.

Making the Adenoviral E1B-93R Splice Site Acceptor Mutant

The first 5000 nucleotides of the Ad5 wt genome (NCBI Reference Sequence: AC_000008.1) were PCR amplified (primers Ad5wt5000start: SEQ ID NO: 15 ccacctcgagttaat-taaCATCATCAATAATATACCTTATTTTG; Ad5wt5000as: SEQ ID NO: 16-gtgggtttaaacGGATTTGGTCA-GGGAAAACATG) and agarose gel purified. The purified product was digested with restriction enzymes NotI and PmeI (New England Biolabs) and cloned into the pShuttle plasmid (Stratagene), replacing the existing left arm for homologous recombination, producing pShuttle-LA, as by Agilent Technologies, AdEasy www.genomics.agilent.com/CollectionSubpage.aspx?PageType=Product&SubPage-Type=ProductData&PageID=592. This plasmid was recombined with the plasmid pTG3602, containing the complete Ad5 wt genome, as recommended by Agilent Technologies in their AdEasy system using BJ5183 recombination competent cells. After recombination the BJ5183 bacteria were plated onto agar plates containing kanamycin. Single colonies were picked, grown and DNA was prepared from large cultures. Each DNA preparation was screened for the correct recombination event. The digestion of the genomes was performed with PacI (New England Biolabs). After the correct clones had been grown on agar plates, the genomes were digested out and transfected into HEK293 cells using Transfectin Transfection Reagent (Bio-Rad) according to the manufacturers' instructions. Four days after transfection virus lysates were harvested [Cells were collected by scraping together with the media and collected in a 15 ml falcon tube. The sample was freeze/thawed three times and used to infect a T175 bottle about 90% confluent with Hek293 cells. Three days later the cells and media was harvested and freeze/thawed three times] and then used to infect viral production factories called CF-10s (Nunc). These have the approximate surface area of forty T175 bottles, i.e. 7000 cm2, and are used to grow large number of cells for the production of a large number of viruses. Briefly, the cells of four confluent T175 bottles were transferred in 1 L of 5% FCS DMEM media into a CF10. Twenty-five ml (1/40) of the cell-containing media was applied to a new T 175 as a growth control. On the day the T175 was 90% confluent the CF10 was at the same stage. Half of the cell lysate was then injected into the CF10 and the media was moved around for an even distribution. Three days later the CF10 was shaken to dislodge the cells that had not started floating around yet due to viral infection. The CF10 was emptied, the cells spun down, washed in PBS and finally suspended in 50 mM Tris-HCl, pH7.8. Purification was carried out by Caesium-chloride banding. Viruses were then purified and analysed for titre (particles) and activity (pfu). The vp:pfu unit ratio (vp:pfu units) for all viruses was between 10-20. Sequencing of one of the viral clones showed that it had a point mutation in the E1B-93R splice acceptor site.

Confirming the Existence of E1B-156R in Ad2, Ad4 and Ad11

Figure 14:
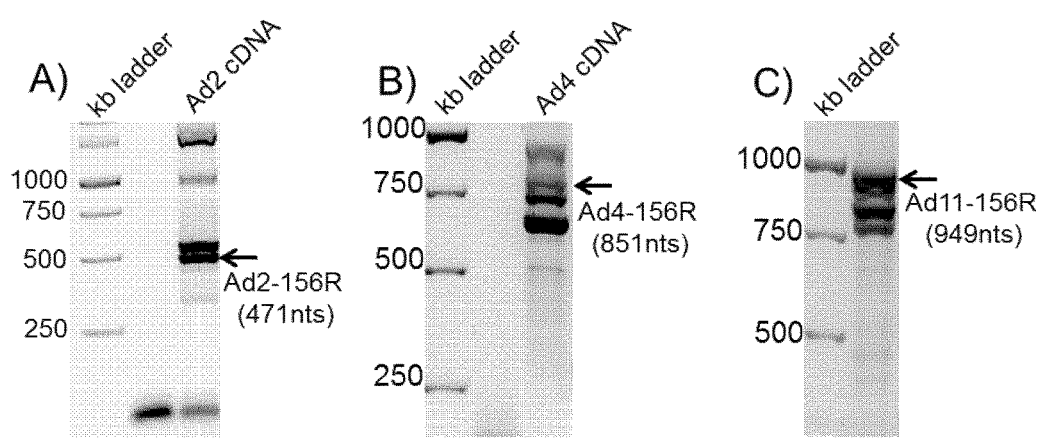
FIG. 14. DNA gels showing amplified cDNA bands corresponding to E1B-156R in Ad2, Ad4 and Ad11. All bands in the gels were cloned into the Topo-II PCR Blunt Vector (Invitrogen) and sequenced to confirm the indicated bands corresponded to the E1B-156R of each respective virus.

A549 cells were infected with 5 pfu/cell of each virus. At 48 hpi, total RNA was extracted and 1 μg was converted to cDNA using Superscript-II (Invitrogen) with random hexamers. One μl of the total 50 ml was used as template in a PCR with serotype-specific primers (Ad2sense, SEQ ID NO: 33—ctcgaggaattcgccaccatggagcgaagaaacccatc, Ad2antisense, SEQ ID NO. 34—cacttctagatcaatctgtatct-tcatcgctag, Ad4sense, SEQ ID NO. 35—ggagataggacggtct-tgg, Ad4antisense, SEQ ID NO. 36—ggatcccatcacattttgacg, Ad11sense, SEQ ID NO. 37—catccatggaggtttgggc, Ad11antisense, SEQ ID NO. 38—ccttaaaagaagcgtttccac). FIG. 14 shows a DNA gel showing the cDNA bands and highlights the bands corresponding to the E1B-156R cDNA. All bands on the gels were purified (NucleoSpin Gel and PCR Clean-up, Macherey-Nagel) and cloned into a Topo-II PCR Blunt Vector (Invitrogen). Clones were sent for sequencing. Ad2-156R and Ad5-156R were cloned into the p3×Flag-CMV-14 vector using EcoRI and XbaI.

Testing if the E1B-156R Protein Enhances Oncolytic Index

The cDNA for E1B-156R from Ad2 and Ad5 were PCR amplified using start and stop primers specific for each respective E1B-55k as discussed above. The primers included an EcoRI in the start primer and a XbaI site in the stop primer. The PCR fragments were digested with the two enzymes and ligated into p3×Flag-CMV-14 (Sigma-Aldrich). The constructs were sequenced for the correct insert.

Cancer cells (Hela and H460) and normal cells (NHBE) were transfected with 2 μg Ad2-156R or Ad5-156R expression plasmids (or a control plasmid) and co-infected with Ad5wt, ONYX-015 or Ad2wt. The transfection was performed using JetPRIME reagent (POLYPlus) according to manufacturers' instructions. Infection with the viruses was performed as discussed above. Briefly, each well in a 6-well plate was transfected with 2 μl JetPRIME reagent and 200 μl transfection buffer. Control wells were transfected with 2 μg inert plasmid, in the form of pUC19.

Figure 11A:
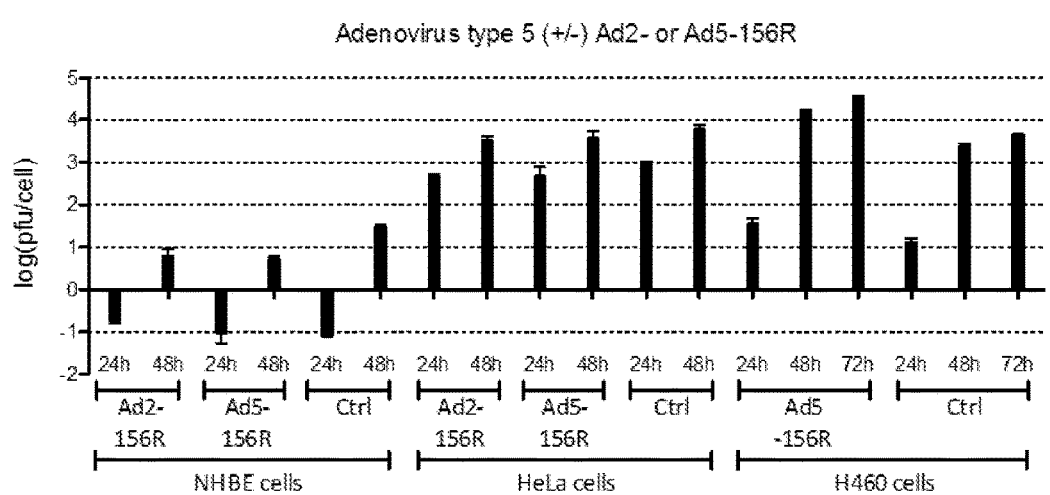
FIG. 11. Ad5- and Ad2-156R proteins enhanced the Oncolytic Index (OI) in cancer cells as compared to normal cells. A) Ad5- and Ad2-156R expression plasmids were transfected into Ad5wt-infected HeLa and NHBE cells. In parallel, an additional cancer cells line (H460, large cell lung carcinoma) was included in Ad5-156R complementation. B) Ad5-156R was transfected into ONYX-015 infected cells. C) Ad5-156R was transfected into Ad2wt-infected cells. The cells were infected with 2.5 pfu/cell and complemented or cross-complemented with expression plasmids for the respective E1B-156R. Samples were analysed with a Burst (viral replication) assay, at the indicated hpi.

Viral replication was measured at various time points post-infection using the assays described above. The data are shown in FIGS. 11A, B and C. Oncolytic index was calculated as shown in FIG. 12.

Results

E1B-55k Protein is Lost

Figure 3:
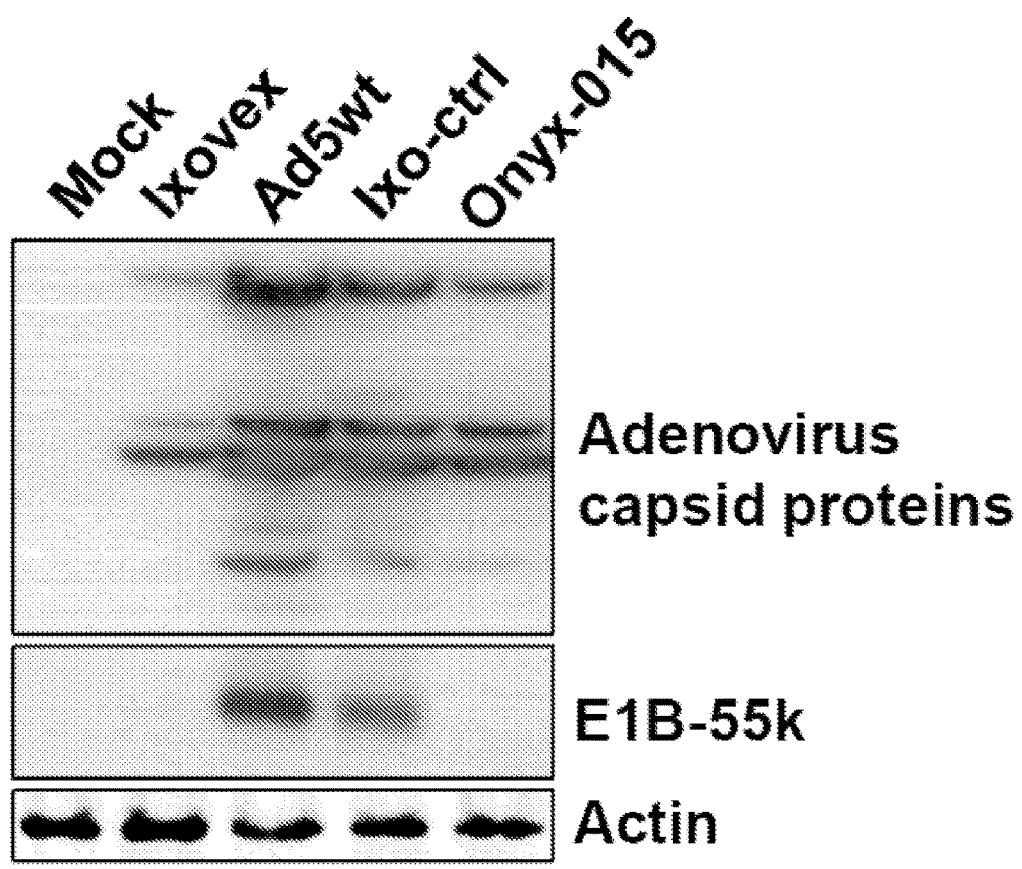
FIG. 3. An amino acid change in Ixovex in the E1B-55k protein inhibits its expression. A549 cells were infected with the respective virus at 5 pfu/cell and total cell lysate was collected 48 hours post infection (hpi). Shown is a western blot stained with polyclonal α-capsid protein Ab6982 antibody (top panel), monoclonal α-E1B-55k antibody 2A6 (middle panel) and monoclonal α-actin antibody I-19-SC as loading control (lowest panel).
Figure 6:
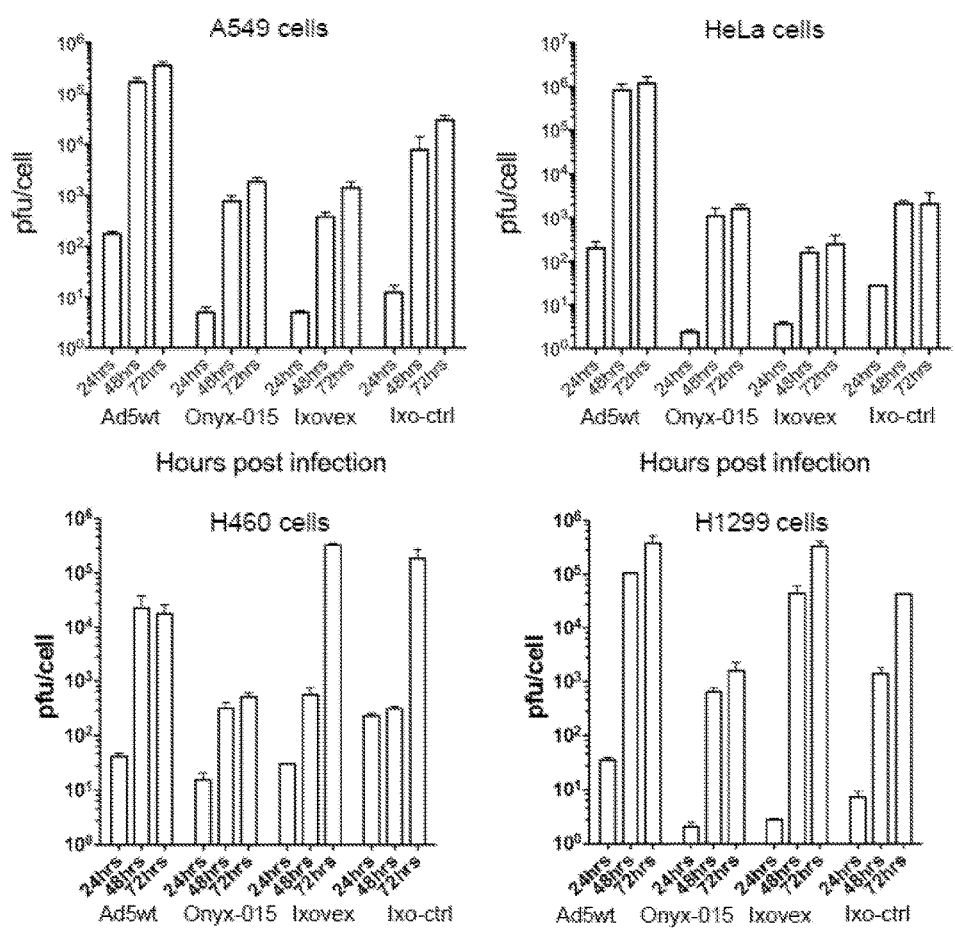
FIG. 6. Replication assay in cancer cell lines. Each cell line was infected with 5 pfu/cell of respective virus. Cells and media were harvested at 24, 48 and 72 hpi and analysed by a limited dilution assay. CPE was noted visually after 10 days and $TCID_{50}$ (pfu/cell) results were calculated, as described in materials and methods.

Total protein lysates from Ad5wt, Onyx-015, Ixovex and Ixo-ctrl infected A549 cells showed that at 48 hpi all viruses expressed late protein (FIG. 3, top panel), i.e. had reached the late phase of adenoviral replication. Both Ixovex and Onyx-015 viruses expressed less late proteins than the Ad5wt and Ixo-ctrl, mirroring the reduced replication efficiency seen in FIG. 6 for A549 cells. The Ixovex single nucleotide point mutation (SNP, genomic location 3216), which changes the amino acid at position 400 in the E1B-55k protein from an arginine to a glycine, induced its destabilisation (FIG. 3, middle panel). The reduced amount of E1B-55k in Ixo-ctrl compared to Ad5wt mirrors the slightly lower replication efficiency of Ixo-ctrl in the A549 cells (FIG. 6, A549 panel).

Dynamics in the Usage of the E1B Splice Acceptors

Figure 4:
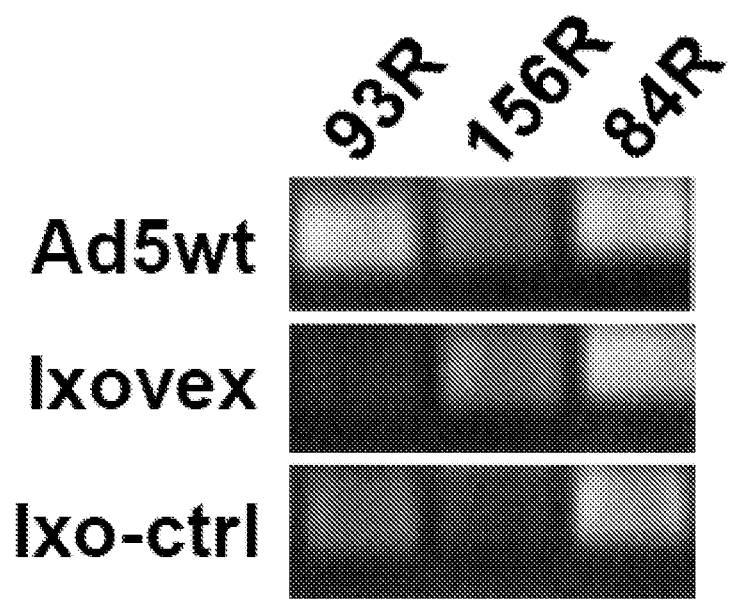
FIG. 4. The point mutation in the E1B55k open reading frame in Ixovex inhibits splicing to the 93R splice acceptor. A549 cells were infected with the respective virus at 5 pfu/cell and total RNA was collected at 48 hpi. cDNA was made using an oligo-dT primer. PCR was performed using a common sense primer upstream of the 55k splice donor and specific primers downstream of respective splice acceptor. The PCR reactions were run on a 2% agarose TBE gel stained with GelRed.

The SNP also inhibited use of the E1B-93R splice acceptor (FIG. 4, second panel) by changing the putative splice acceptor sequence from CAG:GA to CGG:GA. Interestingly, as a secondary effect to the inhibition of the 93R splice site, there is a compensatory switch to use of the E1B-156R splice acceptor (FIG. 4, middle panel). In the absence of the E1B-93R splice acceptor mutation, i.e. Ixo-ctrl, the relative use of the 93R splice site is restored (FIG. 4, lowest panel) as compared to the Ad5wt virus (FIG. 4, top panel). Onyx-015 could not be used in this experiment since this virus is deleted in the whole of the E1B-55k gene region.

Ixovex is Unable to Induce Degradation of p53

Figure 5:
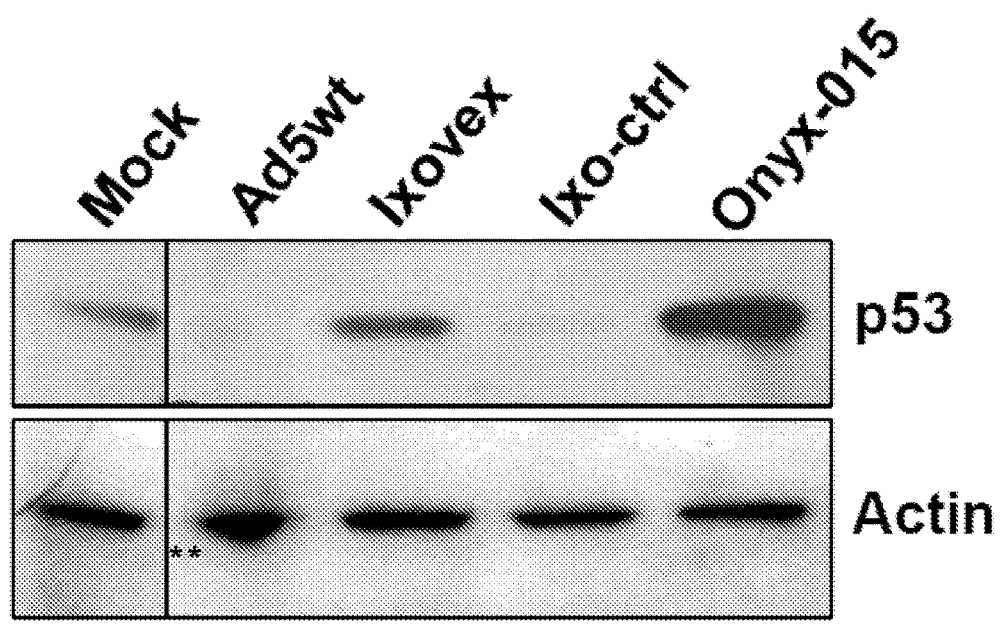
FIG. 5. Ixovex is inhibited in inducing degradation of p53. A549 cells were infected with the respective virus at 5 pfu/cell and cell lysate was collected 48 hpi. Shown is a western blot staining with a monoclonal α-p53 antibody #9282 CS (top panel) and the monoclonal α-actin antibody I-19-SC as loading control (lower panel).

Western blot analysis showed that the SNP in Ixovex inhibited the virus from inducing the degradation of p53 (FIG. 5). In the absence of the E1B-93R splice acceptor mutation (i.e. Ixo-ctrl), the virus's capacity to inhibit p53 was restored. Interestingly, there was a much higher expression of p53 in the Onyx-015 infected cells.

Replication Efficiency in Cancer Cells

A replication assay was performed using Ad5wt, Onyx-015, Ixovex and Ixo-ctrl viruses in A549, HeLa, H460, H1299 and FaDu cells. The replication efficiency of all the viruses was below the detection limit in FaDu cells. In A549 and HeLa cells all viruses showed replication efficiency up to two orders of magnitude lower than the Ad5wt virus (FIG. 6, top panels). The replication attenuation was not seen, or was much less pronounced, in H460 and H1299 cells (FIG. 6, lower panels). In the two more permissive cancer cell lines, 100- to 1000-fold more Ixovex virus was produced, compared to Onyx-015.

Cytotoxicity in Cancer Cells

Figure 7:
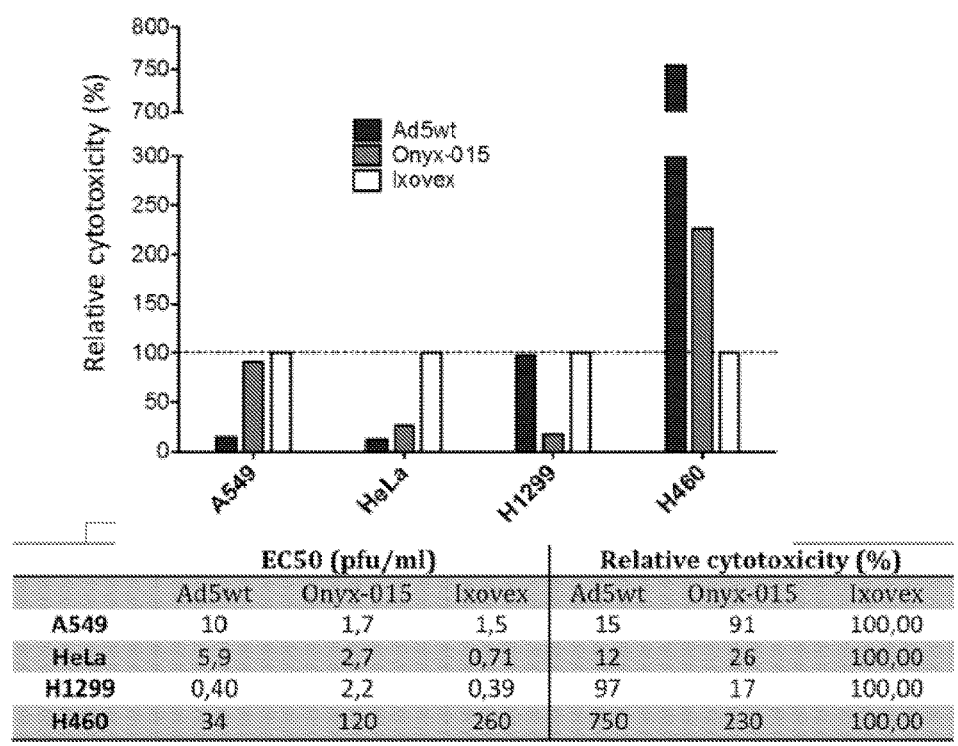
FIG. 7. The relative cytotoxicity of the Ixovex, Ad5wt and Onyx-015 viruses in cancer cells. The respective cell line was infected with the indicated viruses in a 5-fold dilution series. The cytotoxicity was measured 6 days post infection (dpi) using the MTS assay and $EC_{50}$ values were calculated.

FIG. 7 shows the cytotoxicity of the Onyx-015 and Ixovex viruses relative to the Ad5wt virus in cancer cells. In comparison to Onyx-015, Ixovex was more efficient in all the cells tested (apart from H460 cells, in which Onyx-015 was 2.5-fold more toxic). The cytotoxicity of the Ixovex virus was similar to (or much higher than) the Ad5wt virus in the A549, HeLa and H1299 cancer cells lines.

Toxicity Profile in Normal Cells

The cytotoxicity of the Ad5wt, Onyx-015, Ixovex and Ixo-ctrl viruses was measured in NHBE cells (Normal Human Bronchial Epithelial cells). As seen in FIG. 9, the Ad5wt, Onyx-015, and Ixo-ctrl viruses are relatively toxic in normal cells as compared to cancer cells. The Ixovex virus however, showed an $EC_{50}$ value of 23 pfu/cell, which was higher than its $EC_{50}$ in the A549, HeLa and H1299 cancer cell lines. Ad5wt and Ixo-ctrl virus had $EC_{50}$ values of 0.042 and 0.031 pfu/cell, respectively, while Onyx-015 had 0.63 pfu/cell. Thus, Ad5wt was greater than 500-fold, Ixo-ctrl greater than 700-fold and Onyx-015 was greater than 35-fold more toxic to normal cells than Ixovex.

Replication Efficiency in NHBE Cells

Figure 8:
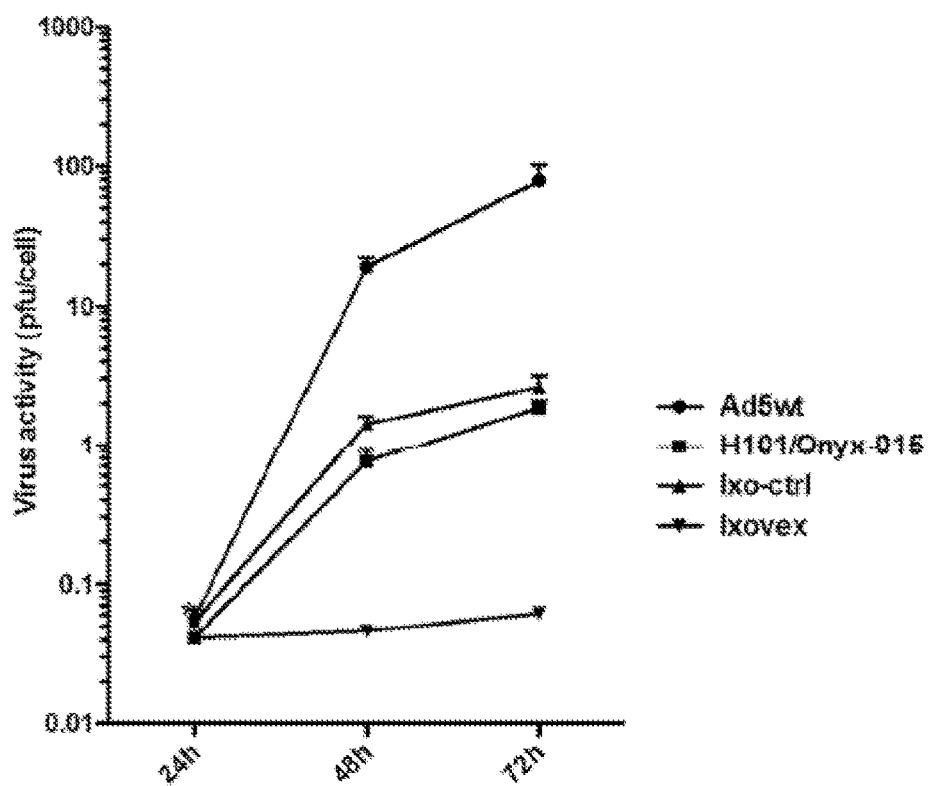
FIG. 8. Replication efficiency in Normal Human Bronchial Epithelial cells. Each cell line was infected with 5 pfu/cell of the respective virus. Cells and media were harvested at 24, 48 and 72 hpi and analysed by a limited dilution assay. CPE was noted visually after 10 days and $TCID_{50}$ (pfu/cell) results were calculated, as described herein.

At 48 hpi, virus activity was 30-fold higher in Ixo-ctrl and Onyx-015 and 500-fold higher in Ad5wt compared to Ixovex virus (FIG. 8). These differences were even more pronounced at 72 hpi, where virus activity was 50-fold higher in Ixo-ctrl and Onyx-015 and over 2000-fold higher in Ad5wt. In fact, these differences might even be more pronounced since Ixovex replication barely reached detection limit at all time points.

Ixovex Overexpressed the E1B-156R Protein

Figure 10:
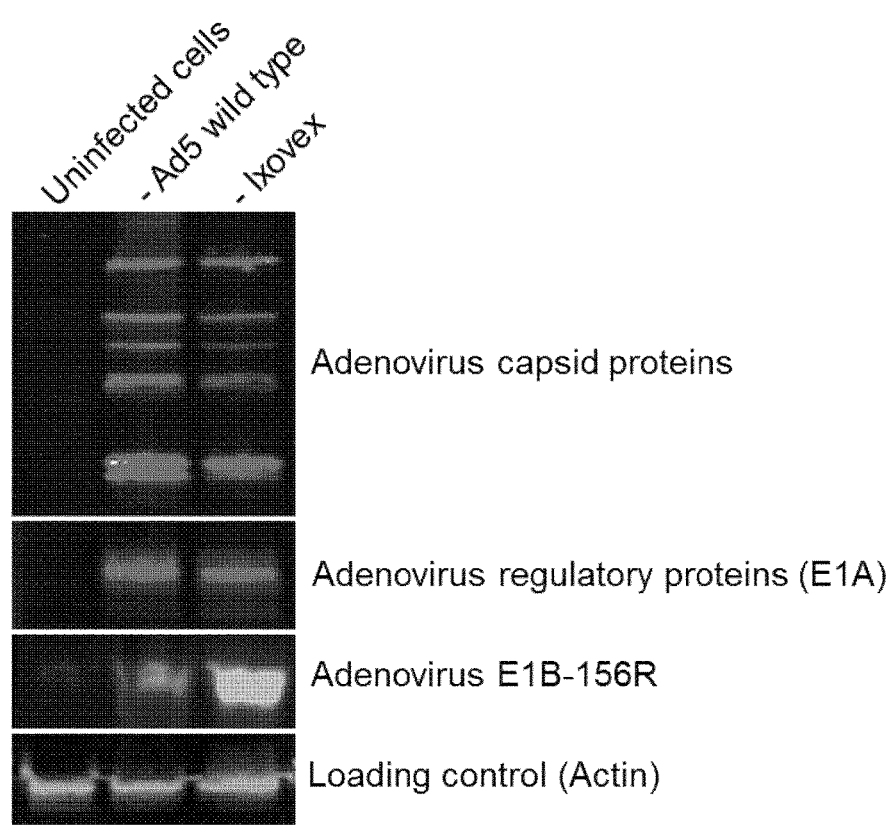
FIG. 10. The E1B-156R protein is overexpressed by Ixovex. Western blot was performed on total protein extracted at 48 hpi from H1299 cells infected with 10 pfu/cell of Ixovex or Ad5wt.

The protein levels of E1B-156R, adenovirus capsid proteins and E1A expressed by Ad5wt- and Ixovex-infected H1299 cells were analysed by western blot. FIG. 10 shows that Ixovex expressed similar amounts of all viral proteins except for the E1B-156R protein, the levels of which were increased by more than 20-fold, as compared to Ad5wt.

E1B-156R Protein Enhances Oncolytic Index

Figure 11B:
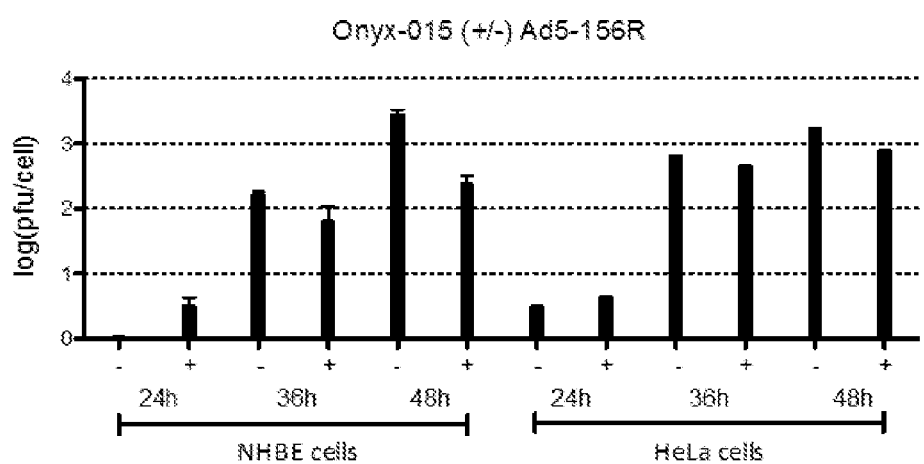
Figure 11C:
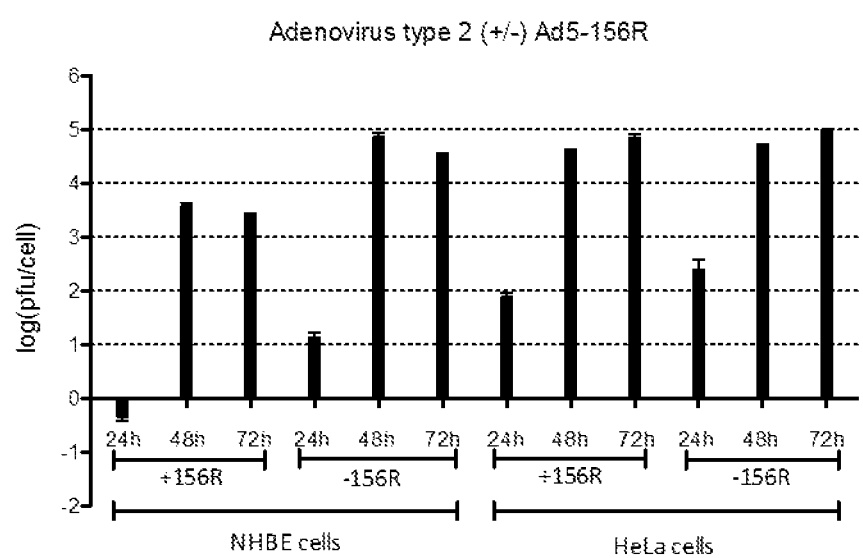
Figure 13:
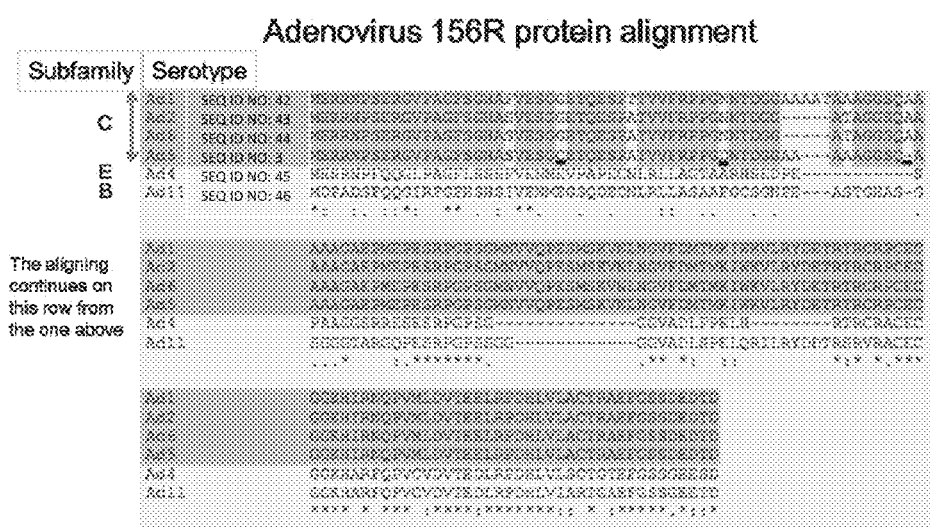
FIG. 13. The protein sequence of E1B-156R for the serotypes of adenovirus subfamily C aligned with the sequences for serotypes of the subfamilies B, D and E. Shaded field: The similarities within group C. Gaps indicates where they differ. Underlined on Ad5: The amino acids that would single out Ad5-156R from the other E1B-156R proteins in subfamily C. (Serotype Ad1 (SEQ ID NO: 42); Ad2 (SEQ ID NO: 43); Ad6 (SEQ ID NO: 44); Ad5 (SEQ ID NO: 3); Ad4 (SEQ ID NO: 45); and Ad11 (SEQ ID NO: 46)).

We hypothesised that adding the E1B-156R protein in trans would enhance the oncolytic index (OI) for Ad5wt if the E1B-156R protein was responsible for the oncolytic effect. Transfecting an Ad5-156R expression plasmid and co-infecting with Ad5wt increased the OI by 4-fold using Hela and NHBE cells (FIG. 11A and FIG. 12). An increase in oncolytic index was also observed when the same experiment was performed in an alternative cancer cell line, H460 (large cell lung carcinoma). Addition of Ad5-156R to Ad5wt-infected cells also had an enhancing effect on viral replication (FIG. 11A). Ad5-156R was transfected into cells co-infected with the ONYX-015 virus, which lacks the E1B-156R gene completely. The addition of Ad-156R increased the OI of the ONYX-015 more then 5-fold at the 48 hpi time point (FIG. 11B and FIG. 12). Similarly, addition of Ad5-156R to Ad2-infected cells increased OI 15-fold. Adenovirus serotypes from the same subfamily have a very small difference in protein sequence in comparison (FIG. 13). The closest adenovirus family member to Ad5 is Ad2. Addition of Ad2-156R to Ad5wt-infected cells increased OI almost 3-fold.

Discussion

It was early discovered that the RNA expressed from the adenovirus E1B gene region had a complex splicing pattern. The full-length 2.28 kb long RNA is polycistronic carrying two overlapping reading frames. The alternative usage of either an early weak or a strong down-stream translation start site produces E1B-19k and E1B-55k, respectively (Perricaudet, Akusjarvi et al. 1979; Bos, Polder et al. 1981). A common splice donor early in the 55k ORF is used to splice to three alternative splice acceptors, 93R SA, 156R SA and 84R SA (Anderson, Schmitt et al. 1984; Virtanen and Pettersson 1985; Anderson, Maude et al. 1987). The 93R AS splices out of frame with the 55k ORF adding a 15 amino acid C-terminus. The 156R AS splices in frame with E1B-55k removing the 340 middle amino acids. The 84R SA is a down-stream site adding 6 amino acids to the common N-terminus.

When making a large set of gene-modified viruses based on the wild type adenovirus serotype 5 strain pTG3602 one viral clone was mutated at a single nucleotide position (SNP) in the E1B-55k gene region. The mutation was made inside the splice acceptor sequence of E1B-93R, or more precisely, it changed the putative site from cag/ga to cGg/ga. Not only did the mutation change the splice site but it also changed E1B-55k amino acid 400 from an arginine to a glycine. This virus has been named Ixovex. We have characterised this virus when it comes to oncolytic potential, meaning, retaining replication capacity and cytotoxicity in cancer cells while being inhibited on both accounts in normal cells.

Our results show that the mutation leads to a lack of expressed E1B-55k protein in infected cells (FIG. 3). We believe this is because the amino acid change destabilises the E1B-55k protein. Others have introduced amino acid changes into E1B-55k and several of these made the protein level unstable. In addition, our mutation changes an important nucleotide in the E1B-55k splice acceptor site 93R, which negates splicing to that particular splice site (FIG. 4). To compensate, the splicing appears to be re-directed to the E1B-156R splice acceptor. With the lack of E1B-55k in the infection, Ixovex's ability to inhibit the expression of p53 is severely reduced (FIG. 5). The reduced level of induced p53 by Ixovex compared to Onyx-015 could have been because of the slightly lower replication efficiency of Ixovex in A549 cells, i.e. the cells are less affected, hence less p53 is expressed. Alternatively, and what we believe, the increased splicing to the 156R splice acceptor (FIG. 4) may also increase expression of the E1B-156R protein. The 156R splicing splices in-frame with the C-(carboxy)-terminal part of E1B-55k. This removes the middle 340 amino acids leaving the C-terminal 78 amino acids fused to the N-(amino)-terminal 79 amino acids. The Dobner lab has shown (Sieber and Dobner 2007) that the E1B-156R protein retains some ability to inhibit p53 through its C-terminus. It is also possible that E1B-156R retains other functions of the E1B-55k protein.

The E1B-55k and E1B-156R protein interacts with many similar factors (Sieber and Dobner 2007; Schreiner, Wimmer et al. 2010; Schreiner, Wimmer et al. 2011; Wimmer, Blanchette et al. 2012). E1B-55k has been assigned several functions besides mediating the degradation of p53. It is also connected to regulating the selective nuclear export of late viral RNA (Dobner and Kzhyshkowska 2001; Flint and Gonzalez 2003) and inhibiting translation of cellular RNA while promoting viral RNA translation (Blackford and Grand 2009). The main functions of E1B-55k are mediated when the protein is in complex with another viral protein, the E4orf6. Interestingly, the E1B-156R protein has been shown to interact with the E4orf6 protein (Sieber and Dobner 2007). The E1B-156R might compensate for some of these functions, which fit with the increased expression of E1B-156R by Ixovex.

In normal cells, the toxicity of each virus largely mirrored respective replication capacity. The lack of toxicity and the almost complete shutdown of replication in normal cells indicate an astounding safety profile of Ixovex. That the Onyx-015 virus replicated better in normal cells than Ixovex is intriguing considering that the deletion the Onyx-015 virus carries removes all possibilities to express E1B-55k, -93R and -156R protein (Barker and Berk 1987). This indicates that it is the imbalance of expression in the E1B region that had the extensive impact on the attenuation of Ixovex in normal cells in comparison to the other viruses. Interestingly, the difference in replication in normal cells between Onyx-015 and Ixo-ctrl on one hand and Ixovex on the other was not seen in the cancer cells. This indicates that the Ixovex infection in normal cells has become non-permissive, i.e. there is probably a major blockage early in infection giving the cells time to clear the virus, whereas the transformed state of cancer cells compensates for the lack of some E1B-55k function(s).

The effect of the imbalanced E1B expression in cancer cells was different depending on cancer cell line. The cytotoxicity of Ixovex in the two highly replication-permissive cell lines H1299 and H460 was low while the cytotoxicity was high in the replication-attenuated cell lines, A549 and HeLa. The reason for this is probably because of the toxicity, the cells died before producing high numbers of virus.

The adenovirus family is divided into 7 genera, named A-G, with a total of more than 65 different serotypes. Serotype 5 (Ad5) belongs to genera C. We believe that the splicing pattern seen in Ad5 is conserved among all adenovirus serotypes and that the imbalance through splice site mutation causing a very advantageous oncoselectivity for Ad5 would be mirrored in most if not all of the other serotypes. Our preliminary experiments show similar splicing patterns in representative viruses from each of the different genera (A-Ad12, B1-Ad3, B2-Ad11, C-Ad5, D-Ad37, E-Ad4 and F-Ad40).

The overall higher efficacy of the Ad5wt virus to all the other viruses is probably due to the wild type strain pTG3602 (Oberg, Yanover et al. 2010), used as genome backbone for Ixovex and Ixo-ctrl. This backbone carries a few point mutations scattered throughout the genome. Our Ixo-ctrl virus is actually pTG3602 in essence. The SNP in Ixovex was reverted back to wild type state producing the Ixo-ctrl virus. In the numerous experiments where pTG3602 has been employed a constant lower efficacy has been seen, as compared to the Ad5wt.

An additional advantage of Ixovex in comparison to patented adenovirus vectors of similar approach is that the Onyx-015 (Heise, Sampson-Johannes et al. 1997), -051 and -053 (Shen, Kitzes et al. 2001) all are missing the E3B gene region of the virus. This region was originally deleted to enhance the safety profile of Onyx-015. It was later found that the elimination of this region made the vector prematurely cleared from the tumour by the immune defence (Wang, Hallden et al. 2003).

Through the western blot analysis on infections in H1299 cells it was shown that Ixovex replicates and expresses viral proteins to the same level as Ad5wt. The only difference between the viruses was seen when using a specific antibody for the N-terminal region of E1B-55k (mouse-m2A6), a drastic increase in the E1B-156R spliceoform of the E1B-55k protein (FIG. 10). We decided to perform a number of complementation experiments to verify whether indeed an increase in E1B-156R could be responsible for the increase in Oncolytic Index (OI). In FIGS. 11A, B and C and FIG. 12, we show that adenovirus type 5 E1B-156R is a potent enhancer of the OI in the subfamily group C. The E1B-156R equivalent from Ad2wt was also shown to have a positive effect on the OI of Ad5wt. Interestingly, adding Ad5-156R to Ad5wt-infected H460 cells increased the replication of the virus, which was in line with the much higher replication level of Ixovex as compared to the ONYX-015 virus (lacking the E1B-156R gene) in H460 cells (see FIG. 6).

It is important to note that these experiments, where E1B-156R is supplemented to the virus-infected cells does not completely resemble infection with Ixovex or another engineered virus that expresses E1B-156R. For example, during viral infection with Ixovex Ad5-156R levels are increased when the virus replicates, i.e. the amount of expression template (viral DNA) increases. In contrast, in the complementation experiments the E1B-156R is provided at a constant template level, i.e. as the cells continue to divide during the early phase of the infection the plasmid harbouring the E1B-156R gene is diluted. Thus, when the virus starts replicating E1B-156R expression will not increase exponentially (as would be the case for a viral copy). However, these experiments clearly show that addition of E1B-156R has the effect of increasing oncolytic index and suggest that E1B-156R is responsible for this effect.

REFERENCES

Anderson, C. W., R. C. Schmitt, et al. (1984). "Early region 1B of adenovirus 2 encodes two coterminal proteins of 495 and 155 amino acid residues." *Journal of virology* 50(2): 387-396.

Anderson, R. E., M. B. Maude, et al. (1987). "Abnormal plasma levels of polyunsaturated fatty acid in autosomal dominant retinitis pigmentosa." *Experimental eye research* 44(1): 155-159.

Barker, D. D. and A. J. Berk (1987). "Adenovirus proteins from both E1B reading frames are required for transformation of rodent cells by viral infection and DNA transfection." *Virology* 156(1): 107-121.

Beatty, M. S. and D. T. Curiel (2012). "Adenovirus strategies for tissue-specific targeting." *Advances in cancer research* 115: 39-67.

Blackford, A. N. and R. J. Grand (2009). "Adenovirus E1B 55-kilodalton protein: multiple roles in viral infection and cell transformation." *Journal of virology* 83(9): 4000-4012.

Bos, J. L., L. J. Polder, et al. (1981). "The 2.2 kb E1b mRNA of human Ad12 and Ad5 codes for two tumor antigens starting at different AUG triplets." *Cell* 27(1 Pt 2): 121-131.

Bradshaw, A. C. and A. H. Baker (2012). "Gene therapy for cardiovascular disease: Perspectives and potential." *Vascular pharmacology*.

Bradshaw, A. C., L. Coughlan, et al. (2012). "Biodistribution and inflammatory profiles of novel penton and hexon double-mutant serotype 5 adenoviruses." *Journal of controlled release: official journal of the Controlled Release Society*.

Dobner, T. and J. Kzhyshkowska (2001). "Nuclear export of adenovirus RNA." *Current topics in microbiology and immunology* 259: 25-54.

Flint, S. J. and R. A. Gonzalez (2003). "Regulation of mRNA production by the adenoviral E1B 55-kDa and E4 Orf6 proteins." *Current topics in microbiology and immunology* 272: 287-330.

Heise, C., A. Sampson-Johannes, et al. (1997). "ONYX-015, an E1B gene-attenuated adenovirus, causes tumor-specific cytolysis and antitumoral efficacy that can be augmented by standard chemotherapeutic agents." *Nature medicine* 3(6): 639-645.

Nasz, I., E. Adam, et al. (2001). "Alternate adenovirus type-pairs for a possible circumvention of host immune response to recombinant adenovirus vectors." *Acta microbiologica et immunologica Hungarica* 48(2): 143-146.

Oberg, D., E. Yanover, et al. (2010). "Improved potency and selectivity of an oncolytic E1ACR2 and E1B19K deleted adenoviral mutant in prostate and pancreatic cancers." *Clinical cancer research: an official journal of the American Association for Cancer Research* 16(2): 541-553.

Perricaudet, M., G. Akusjarvi, et al. (1979). "Structure of two spliced mRNAs from the transforming region of human subgroup C adenoviruses." *Nature* 281(5733): 694-696.

Schreiner, S., P. Wimmer, et al. (2011). "Adenovirus type 5 early region 1B 55K oncoprotein-dependent degradation of cellular factor Daxx is required for efficient transformation of primary rodent cells." *Journal of virology* 85(17): 8752-8765.

Schreiner, S., P. Wimmer, et al. (2010). "Proteasome-dependent degradation of Daxx by the viral E1B-55K protein in human adenovirus-infected cells." *Journal of virology* 84(14): 7029-7038.

Shen, Y., G. Kitzes, et al. (2001). "Analyses of single-amino-acid substitution mutants of adenovirus type 5 E1B-55K protein." *Journal of virology* 75(9): 4297-4307.

Sieber, T. and T. Dobner (2007). "Adenovirus type 5 early region 1B 156R protein promotes cell transformation independently of repression of p53-stimulated transcription." *Journal of virology* 81(1): 95-105.

Virtanen, A. and U. Pettersson (1985). "Organization of early region 1B of human adenovirus type 2: identification of four differentially spliced mRNAs." *Journal of virology* 54(2): 383-391.

Wang, Y., G. Hallden, et al. (2003). "E3 gene manipulations affect oncolytic adenovirus activity in immunocompetent tumor models." *Nature biotechnology* 21(11): 1328-1335.

Wimmer, P., P. Blanchette, et al. (2012). "Cross-talk between phosphorylation and SUMOylation regulates transforming activities of an adenoviral oncoprotein." *Oncogene*.

The invention claimed is:

1. A recombinant adenovirus for which the proportion of the E1B-156R isoform is increased relative to wild-type levels, wherein the adenovirus has an oncolytic effect in a cancer cell, and wherein the recombinant adenovirus carries a mutation in the sequence of the E1B gene of the adenovirus and the mutation in the E1B gene is A3216G wherein the numbering is relative to the adenovirus Ad5 genome (accession number AC_000008.1) (SEQ ID NO: 41) (position 1503 in the E1B gene (SEQ ID NO: 1)) or a guanine point mutation at an equivalent position to 3216 in any other adenovirus serotype.

2. The recombinant adenovirus according to claim 1, where the adenovirus is adenovirus serotype Ad5, or adenovirus serotype Ad5 strain pTG3602.

3. The recombinant adenovirus according to claim 1, where the wild-type E1B gene has the polynucleotide sequence according to SEQ ID NO: 1.

4. The recombinant adenovirus according to claim 1, where:
(a) the proportion of the E1B-156R isoform is increased relative to an E1B-496R isoform;
(b) the proportion of an E1B-496R isoform is decreased relative to wild-type levels;
(c) the proportion of the E1B-156R isoform is increased relative to an E1B-93R isoform;
(d) the proportion of the E1B-156R isoform is increased relative to an E1B-84R isoform; and/or
(e) the proportion of an E1B-93R isoform is decreased relative to wild-type levels.

5. The recombinant adenovirus according to claim 1, where the proportion of the E1B-156R isoform is increased at least 2-fold, 4-fold, 10-fold, 100-fold, 1,000-fold or 10,000-fold, and/or the proportion of an E1B-496R isoform is decreased at least 2-fold, 4-fold, 10-fold, 100-fold, 1,000-fold or 10,000-fold.

6. The recombinant adenovirus according to claim 4, where the proportion of the E1B-156R, E1B-496R, E1B-93R, or E1B-84R isoforms refers to:
   a) the level of the isoform protein that is expressed; and/or
   b) the level of the isoform mRNA that is transcribed.

7. The recombinant adenovirus according to claim 4, where:
   (a) the E1B-156R isoform has a polynucleotide sequence that has at least 80% sequence identity to SEQ ID NO: 2;
   (b) the E1B-156R isoform has a polypeptide sequence that has at least 80% sequence identity to SEQ ID NO: 3;
   (c) the E1B-496R isoform has a polynucleotide sequence that has at least 80% sequence identity to SEQ ID NO: 4;
   (d) the E1B-496R isoform has a polypeptide sequence that has at least 80% sequence identity to SEQ ID NO: 5;
   (e) the E1B-93R isoform has a polynucleotide sequence that has at least 80% sequence identity to SEQ ID NO: 6;
   (f) the E1B-93R isoform has a polypeptide sequence that has at least 80% sequence identity to SEQ ID NO: 7;
   (g) the E1B-84R isoform has a polynucleotide sequence that has at least 80% sequence identity to SEQ ID NO: 8; and/or
   (h) the E1B-84R isoform has a polypeptide sequence that has at least 80% sequence identity to SEQ ID NO: 9.

8. The recombinant adenovirus according to claim 1, where the cancer cell is a neoplastic cell.

9. The recombinant adenovirus according to claim 1, where the oncolytic effect is determined by measuring:
   a) viral infection of cells;
   b) selective replication of the viral genome in cancer cells leading to preferential virus-mediated cell lysis in cancer cells, and the release of viral particles for further infection events.

10. A polynucleotide encoding the recombinant adenovirus according to claim 1, which is optionally a vector suitable for adenovirus production in a host cell.

11. An isolated host cell comprising a polynucleotide encoding the recombinant adenovirus according to claim 1.

12. A pharmaceutical composition comprising a recombinant adenovirus, wherein the recombinant adenovirus is characterised in that the proportion of the E1B-156R isoform is increased relative to wild-type levels, and wherein the adenovirus has an oncolytic effect in a cancer cell, and wherein the recombinant adenovirus carries a mutation in the sequence of the E1B gene of the adenovirus and the mutation in the E1B gene is A3216G wherein the numbering is relative to the adenovirus Ad5 genome (accession number AC_000008.1) (SEQ ID NO: 41) (position 1503 in the E1B gene (SEQ ID NO: 1) or a guanine point mutation at an equivalent position to 3216 in any other adenovirus serotype.

* * * * *